United States Patent
Takano et al.

(10) Patent No.: US 6,348,461 B1
(45) Date of Patent: Feb. 19, 2002

(54) 6,7-ASYMMETRICALLY DISUBSTITUTED QUINOXALINECARBOXYLIC ACID DERIVATIVES, ADDITION SALTS THEREOF, AND PROCESSES FOR THE PREPARATION OF BOTH

(75) Inventors: Yasuo Takano, Kazo; Futoshi Shiga, Oyama; Masanori Takadoi, Kuki; Hideharu Uchiki, Nogi-machi; Jun Asano, Sugito-machi; Tsuyoshi Anraku, Koga; Kazunori Fukuchi, Hanyu; Junichiro Uda, Okaya; Naoki Ando, Nogi-machi, all of (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/485,716

(22) PCT Filed: Aug. 28, 1998

(86) PCT No.: PCT/JP98/03832

§ 371 Date: Mar. 1, 2000

§ 102(e) Date: Mar. 1, 2000

(87) PCT Pub. No.: WO99/11632

PCT Pub. Date: Mar. 11, 1999

(30) Foreign Application Priority Data

Sep. 1, 1997 (JP) .............................. 9-251313
Jul. 6, 1998 (JP) ......................... 10-190108
Jul. 6, 1998 (JP) ......................... 10-190109

(51) Int. Cl.$^7$ ................. C07D 241/44; C07D 401/04; C07D 403/04; A61K 31/495; A61K 31/535

(52) U.S. Cl. ................. 514/232.5; 544/354; 544/333; 544/119; 514/249; 514/235.2

(58) Field of Search ................ 544/354, 119, 544/333; 514/249, 235.2, 232.5

(56) References Cited

FOREIGN PATENT DOCUMENTS

WO     92/11245     *  7/1992

OTHER PUBLICATIONS

Sanna et al. Synthesis of substituted 2–ethoxycarbonyl– and 2–carboxyquinoxalin–3–ones for evaluation of antimicrobial and anticancer activity, Farmaco 53: 455–61, Jul. 1998.*
CAS printout for Loriga et al, Jan. 1997.*
CAS printout for Dumaitre et al, Feb. 1995.*
CAS printout for Hays et al, Jul. 1998.*

* cited by examiner

*Primary Examiner*—Mukund J. Shah
*Assistant Examiner*—Henry Liu
(74) *Attorney, Agent, or Firm*—Oblon, Spivak, McClelland, Maier & Neustadt, P.C.

(57) ABSTRACT

The present invention provides 6,7-asymmetrically disubstituted quinoxalinecarboxylic acid compounds and their addition salts, and processes for preparing them, which have antagonism against excitatory amino acid receptors, in particular, an AMPA receptor. The 6,7-asymmetrically disubstituted quinoxalinecarboxylic acid compounds and their addition salts of the present invention are represented by formula (1)

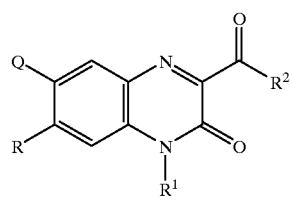

(1)

wherein Q, R, $R^1$ and $R^2$ are as described in the specification.

12 Claims, No Drawings

6,7-ASYMMETRICALLY DISUBSTITUTED QUINOXALINECARBOXYLIC ACID DERIVATIVES, ADDITION SALTS THEREOF, AND PROCESSES FOR THE PREPARATION OF BOTH

TECHNICAL FIELD

The present invention relates to 6,7-asymmetrically disubstituted quinoxalinecarboxylic acid derivatives and their addition salts effective for the therapy of disorder of cerebral nerve cells, as antagonists against excitatory amino acid receptor, in particular, selective antagonists against AMPA receptor in non-NMDA receptor, processes for preparing them, and medicinal compositions containing these compounds.

BACKGROUND TECHNOLOGIES

The glutamic acid being excitatory amino acid is a principal excitatory transmitter substance in the central nervous system of vertebrates, and is known as an amino acid that is contained most rich in brain. It is known, however, that, when released from the axon terminals of nerves exceeding physiological threshold, the overstimutation to the postsynaptic glutamic acid receptors causes the death of nerve cells. This is called excitotoxicity.

In recent years, it is being clarified that the excitotoxicity due to glutamic acid is concerned deeply in the various diseases of cerebral nerves such as cerebral hemorrhage, cephalic injury, epileptic intussusception, Huntington's chorea, Parkinson's disease, amyotrophic lateral sclerosis and Alzheimer's disease. If such excitotoxicity can be prevented effectively, it is considered that a potential for the therapy of these intractable diseases, for which currently there is no therapeutic means whatsoever would be opened.

Classifying roughly, the glutamic acid receptor is divided into ion channel type receptor and G protein-binding type receptor, and this ion channel type receptor is further divided into NMDA (N-methyl-D-aspartic acid) receptor and non-NMDA receptor. Moreover, the latter non-NMDA receptor is classified into AMPA (-amino-3-hydroxy-5-methyl-4-isoxazolepropionic acid) receptor and KA (kainic acid) receptor.

Studies on these excitatory amino acid receptors are being put forward and, above all, it is known that a drug with antagonism against AMPA receptor in non-NMDA receptor expresses no side effects (learning and memory disturbances, schizophrenia-like symptom, etc.) that are brought with a drug (MK-801 or the like) with antagonism against NMDA receptor. (Neurosci. Biobehav. Rev., 1992, 16, 13–24; J. Pharmacol. Exp. Ther., 1958, 245, 969–974), and that the protective effect on cerebral nerves can be expected even by administration after ischemia (Science, 1990, 247, 571–574).

Moreover, compounds with antagonism against AMPA receptor like NBQX having a quinoxalinedione structure have reportedly drawbacks of causing kidney disturbance, etc. that are considered to be based on the physicochemical properties (J. Cereb. Blood Flow Metab., 1994, 14, 251–261), therefore they cannot be said to be satisfactory compounds.

Now, as compounds with a structure similar to quinoxalinecarboxylic acid derivatives, compounds represented by a general formula (A)

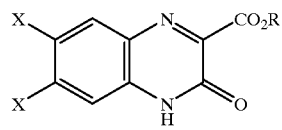

(wherein X independently denotes a chlorine or bromine atom, and R denotes a methyl or ethyl group), described in Japanese Unexamined Patent Publication No. Sho 56-5416 by Lilly Co. as compounds with antiviral function, compounds represented by a general formula (B)

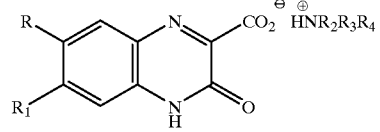

(wherein R and $R_1$ independently denote halogen atoms, $R_2$ denotes a hydrogen, methyl or ethyl group, $R_3$ denotes a hydrogen, methyl, ethyl, hydroxyethyl, benzyl or ethoxycarbonylmethyl group, and $R_4$ denotes a cyclooctyl, norbornyl group or the like), described in Japanese Unexamined Patent Publication No. Sho 56-81569 by Lilly Co. similarly as compounds with antiviral function, and the like are known. However, the 6 and 7 positions are symmetric in these compounds, it is not known that they have antagonism against AMPA receptor in excitatory amino acid receptor of the inventive compounds, and they have a structure different from, that of the inventive compounds.

In addition, compounds represented by a general formula

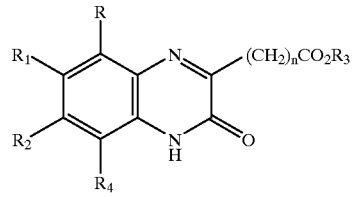

(wherein R and $R_4$ independently denote hydrogens, nitro or methoxy groups, $R_1$ and $R_2$ independently denote hydrogens, nitro or methoxy groups, or halogen atoms (one of R, $R_1$, $R_2$ and $R_4$ is a group other than hydrogen, in the case of $R_1$ and $R_2$ being not nitro groups or methoxy groups, $R_1$ and $R_2$ are independently halogen atoms together and R and $R_4$ are hydrogens, and, in the case of one of R, $R_1$, $R_2$ and $R_4$ being a nitro group, either one of $R_1$ and $R_2$ is a methoxy group), $R_3$ denotes a hydrogen, lower alkyl group which may be substituted with halogen, lower cycloalkyl group, lower alkenyl group or 2-chloroethyl group, and n denotes 0 or 2), described in Japanese Unexamined Patent Publication No. Sho 55-69514 by Lilly Co. similarly as compounds with antiviral function, are known, but the disclosed compounds have a structure different from that of the inventive compounds and it is not described that they have antagonism against AMPA receptor in excitatory amino acid receptor that the inventive compounds have.

Moreover, in WO92–11245 described by Warner-Lambert Co., compounds represented by a general formula (D)

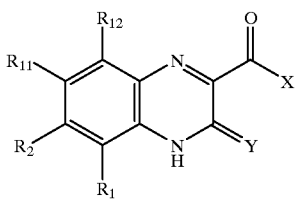

(D)

(wherein Y denotes an oxygen, sulfur or nitrogen atom, $R_1$, $R_2$, $R_{11}$ and $R_{12}$ denote hydrogens, lower alkyl groups which may be substituted with halogen, halogen atoms, trifluoromethyl groups, cyano groups, nitro groups, methylthio groups, lower alkenyl groups, lower alkynyl groups, sulfonamide groups or the like, or arbitrary two of $R_1$, $R_2$, $R_{11}$ and $R_{12}$ may form a ring (6-membered ring or heterocycle which may contain heteroatom), and X denotes a sulfonylamide group which may have substituent, or the like) are known as compounds with antagonism against excitatory amino acid receptors.

However, for these compounds, those having asymmetric substituents of 6 and 7 positions of quinoxaline as the inventive compounds are not disclosed, and, with disclosed compounds, no AMPA antagonism is shown and the disclosed glycine antagonism cannot be considered to be satisfactory as well.

The invention is to provide compounds with antagonism against receptor of glutamic acid that is considered to be an etiology bringing about memory disturbance or dementia due to said diseases and selective death of cells, in particular, with high affinity and selectivity against AMPA receptor in non-NMDA receptor, and with protective effect on the cerebral nerve cells.

DISCLOSURE OF THE INVENTION

As a result of diligent studies exploring an antagonistic drug against excitatory amino acid receptor effective for the therapy of disorder of cerebral nerve cells, in particular, selective antagonistic drug against AMPA receptor in non-NMDA receptor, aiming at the development of novel therapeutic drug for the disorder of cerebral nerve cells, the inventors have found that the inventive 6,7-asymmetrically disubstituted quinoxalinecarboxylic acid derivatives and their addition salts have excellent antagonism against AMPA receptor.

Namely, according to the invention, it has been found that 6,7-asymmetrically disubstituted quinoxalinecarboxylic acid derivatives represented by a general formula (1)

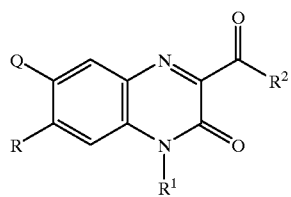

(1)

[wherein, Q denotes a halogen atom, lower alkyl group which may be substituted with halogen atom, general formula (2)

$$Ar-P- \qquad (2)$$

(wherein Ar denotes a phenyl group which may have one or more substituents or naphthyl group, and P denotes a lower alkylene, lower alkenylene, lower alkynylene, oxygen or sulfur atom), general formula (3)

$$L-A- \qquad (3)$$

(wherein L denotes a general formula (4)

(4)

(wherein V denotes a single bond, lower alkylene or lower alkenylene, T denotes a phenyl group, naphthyl group, 5- or 6-membered heterocycle and its condensed ring (these may have one or more substituents on aromatic ring or heterocycle), hydrogen atom, hydroxyl group, thiol group, amino group which may be substituted, lower alkoxycarbonyl group, carboxyl group, aldehyde group, general formula (4-a)

(4-a)

or general formula (4-b)

(4-b)

(wherein U denotes an oxygen atom or sulfur atom, X denotes an oxygen atom or sulfur atom, W denotes an aralkyl group, phenyl group, naphthyl group, 5- or 6-membered heterocycle and its condensed ring (these may have one or more substituents on aromatic ring or heterocycle), lower alkyl group which may be substituted with halogen atom or cycloalkyl group, and $R^3$ denotes an aralkyl group, phenyl group, naphthyl group, 5- or 6-membered heterocycle and its condensed ring (these may have one or more substituents on aromatic ring or heterocycle), hydrogen atom, lower alkyl group which may be substituted with halogen atom or cycloalkyl group), or general formula (4-c)

(4-c)

(wherein X denotes an oxygen atom or sulfur atom, W denotes an aralkyl group, phenyl group, naphthyl group, 5- or 6-membered heterocycle and its condensed ring (these may have one or more substituents on aromatic ring or heterocycle), lower alkyl group which may be substituted with halogen atom or cycloalkyl group, and $R^4$ and $R^5$ identically or differently denote aralkyl groups, phenyl groups, naphthyl groups, 5- or 6-membered heterocycles and their condensed rings (these may have one or more substituents on aromatic rings or heterocycles), hydrogen atoms, lower alkyl groups which may be substituted with halogen atom or cycloalkyl groups), ring B denotes a saturated or unsaturated heterocycle and its condensed ring (these may have one or more substituents on heterocycle or condensed ring) which may additionally contain one or two oxygen, nitrogen or sulfur atoms, and m denotes 0 or 1, A denotes a single bond, lower alkylene, lower alkenylene or lower alkynylene, or general formula (5)

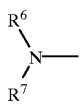

(5)

(wherein $R^6$ and $R^7$ identically or differently denote hydrogen atoms, lower alkyl groups which may be substituted with halogen atom, cycloalkyl groups, phenyl groups which may have one or more substituents or aralkyl groups which may have one or more substituents);

$R^1$ denotes an aralkyl group, phenyl group, naphthyl group, 5- or 6-membered heterocycle and its condensed ring (these may have one or more substituents on aromatic ring or heterocycle), hydrogen atom, lower alkyl group which may be substituted with halogen atom or cycloalkyl group, $R^2$ denotes a hydroxyl group, lower alkoxy group, or general formula (6)

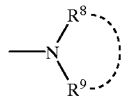

(6)

(wherein $R^8$ and $R^9$ identically or differently denote aralkyl groups, phenyl groups, 5- or 6-membered heterocycles and their condensed rings (these may have one or more substituents on aromatic rings or heterocycles), hydrogen atoms, lower alkyl groups which may be substituted with halogen atom or cycloalkyl groups, or $R^8$ and $R^9$ may form a ring (which may additionally contain one or two heteroatoms) together with nitrogen atom, or either of $R^8$ and $R^9$ denotes a hydrogen atom while the other denotes a phenyloxy group or aralkyloxy group (these may have one or more substituents on aromatic ring), hydroxyl group or lower alkoxy group), and R denotes a nitro group, trifluoromethyl group, amino group which may be substituted, or general formula (7)

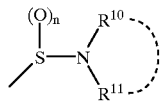

(7)

(wherein $R^{10}$ and $R^{11}$ identically or differently denote aralkyl groups, phenyl groups, 5- or 6-membered heterocycles and their condensed rings (these may have one or more substituents on aromatic rings or heterocycles), hydrogen atoms, lower alkyl groups which may be substituted with halogen atom or cycloalkyl groups, or $R^{10}$ and $R^{11}$ may form a ring (which may additionally contain one or two heteroatoms) together with nitrogen atom, and n denotes 1 to 2)], and their addition salts have excellent antagonism against AMPA receptor, leading to the completion of the invention.

Moreover, according to the invention, it has been found that 6,7-asymmetrically disubstituted quinoxalinecarboxylic acid derivatives represented by a general formula (1)

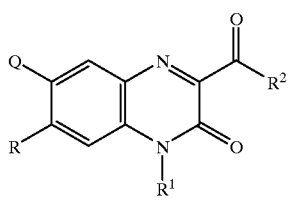

(1)

[wherein, Q denotes a halogen atom, lower alkyl group which may be substituted with halogen atom, general formula (2)

Ar—P—    (2)

(wherein Ar denotes a phenyl group which may have one or more substituents or naphthyl group, and P denotes a lower alkylene, lower alkenylene, lower alkynylene, oxygen or sulfur atom), or general formula (5)

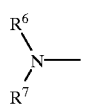

(5)

(wherein $R^6$ and $R^7$ identically or differently denote hydrogen atoms, lower alkyl groups which may be substituted with halogen atom or cycloalkyl groups, phenyl groups which may have one or more substituents or aralkyl groups which may have one or more substituents), R denotes a nitro group, trifluoromethyl group, amino group which may be substituted, or general formula (7)

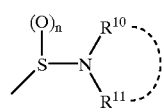

(7)

(wherein $R^{10}$ and $R^{11}$ identically or differently denote aralkyl groups, phenyl groups, 5- or 6-membered heterocycles and their condensed rings (these may have one or more substituents on aromatic rings or heterocycles), hydrogen atoms, lower alkyl groups which may be substituted with halogen atom or cycloalkyl groups, or $R^{10}$ and $R^{11}$ may form a ring (which may additionally,contain one or two heteroatoms) together with nitrogen atom), and n denotes 1 to 2), $R^1$ denotes an aralkyl group, phenyl group, naphthyl group, 5- or 6-membered heterocycle and its condensed ring (these may have one or more substituents on aromatic ring or heterocycle), hydrogen atom, lower alkyl group which may be substituted with halogen atom or cycloalkyl group, and $R^2$ denotes a hydroxyl group, lower alkoxy group, or general formula (6)

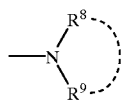
(6)

(wherein $R^8$ and $R^9$ identically or differently denote aralkyl groups, phenyl groups, 5- or 6-membered heterocycles and their condensed rings (these may have one or more substituents on aromatic rings or heterocycles), hydrogen atoms, lower alkyl groups which may be substituted with halogen atom or cycloalkyl groups, or $R^8$ and $R^9$ may form a ring (which may additionally contain one or two heteroatoms) together with nitrogen atom, or either of $R^8$ and $R^9$ denotes a hydrogen atom while the other denotes a phenyloxy group or aralkyloxy group (these may have one or more substituents on aromatic ring), hydroxyl group or lower alkoxy group)], and their addition salts have excellent antagonism against AMPA receptor.

Furthermore, according to the invention, it has been found that 6,7-asymmetrically disubstituted quinoxalinecarboxylic acid derivatives represented by a general formula (1-a)

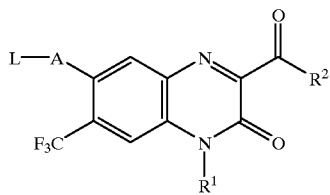
(1-a)

(wherein L denotes a general formula (4)

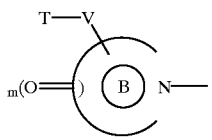
(4)

(wherein V denotes a single bond, lower alkylene or lower alkenylene, T denotes a phenyl group, naphthyl group, 5- or 6-membered heterocycle and its condensed ring (these may have one or more substituents on aromatic ring or heterocycle), hydroxyl group, thiol group, amino group which may be substituted, lower alkoxycarbonyl group, carboxyl group, aldehyde group, general formula (4-a)

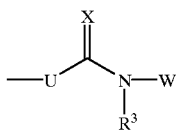
(4-a)

or general formula (4-b)

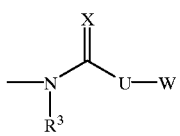
(4-b)

(wherein U denotes an oxygen atom or sulfur atom, X denotes an oxygen atom or sulfur atom, W denotes an aralkyl group, phenyl group, naphthyl group, 5- or 6-membered heterocycle and its condensed ring (these may have one or more substituents on aromatic ring or heterocycle), lower alkyl group which may be substituted with halogen atom or cycloalkyl group, and $R^3$ denotes an aralkyl group, phenyl group, naphthyl group, 5- or 6-membered heterocycle and its condensed ring (these may have one or more substituents on aromatic ring or heterocycle), hydrogen atom, lower alkyl group which may be substituted with halogen atom or cycloalkyl group), or general formula (4-c)

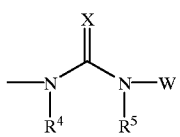
(4-c)

(wherein X denotes an oxygen atom or sulfur atom, W denotes an aralkyl group, phenyl group, naphthyl group, 5- or 6-membered heterocycle and its condensed ring (these may have one or more substituents on aromatic ring or heterocycle), lower alkyl group which may be substituted with halogen atom or cycloalkyl group, and $R^4$ and $R^5$ identically or differently denote aralkyl groups, phenyl groups, naphthyl groups, 5- or 6-membered heterocycles and their condensed rings (these may have one or more substituents on aromatic rings or heterocycles), hydrogen atoms, lower alkyl groups which may be substituted with halogen atom or cycloalkyl groups), ring B denotes a saturated or unsaturated heterocycle and its condensed ring (these may have one or more substituents on heterocycle or condensed ring) which may additionally contain one or two oxygen, nitrogen or sulfur atoms, and m denotes 0 or 1, A denotes a single bond, lower alkylene or lower alkenylene, $R^1$ denotes an aralkyl group, phenyl group, naphthyl group, 5- or 6-membered heterocycle and its condensed ring (these may have one or more substituents on aromatic ring or heterocycle), hydrogen atom, lower alkyl group which may be substituted with halogen atom or cycloalkyl group, and $R^2$ denotes a hydroxyl group, lower alkoxy group, or general formula (6)

(6)

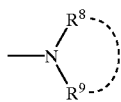

(wherein $R^8$ and $R^9$ identically or differently denote aralkyl groups, phenyl groups, 5- or 6-membered heterocycles and their condensed rings (these may have one or more substituents on aromatic rings or heterocycles), hydrogen atoms, lower alkyl groups which may be substituted with halogen atom or cycloalkyl groups, or $R^8$ and $R^9$ may form a ring (which may additionally contain one or two heteroatoms) together with nitrogen atom, or either of $R^8$ and $R^9$ denotes a hydrogen atom while the other denotes a phenyloxy group or aralkyloxy group (these may have one or more substituents on aromatic ring), hydroxyl group or lower alkoxy group)], and their addition salts have excellent antagonism against AMPA receptor.

Still more, according to the invention, it has been found that 6,7-asymmetrically disubstituted quinoxalinecarboxylic acid derivatives represented by a general formula (1-b)

(1-b)

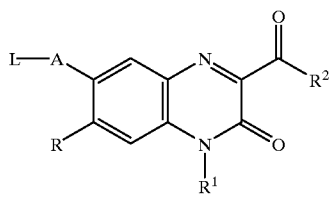

(wherein L denotes a general formula (4)

(4)

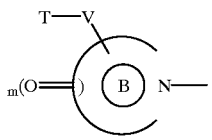

(wherein V denotes a single bond, lower alkylene or lower alkenylene, T denotes a phenyl group, naphthyl group, 5- or 6-membered heterocycle and its condensed ring (these may have one or more substituents on aromatic ring or heterocycle), hydroxyl group, thiol group, amino group which may be substituted, lower alkoxycarbonyl group, carboxyl group, aldehyde group, general formula (4-a)

(4-a)

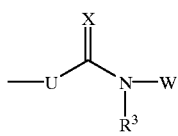

or general formula (4-b)

(4-b)

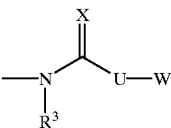

(wherein U denotes an oxygen atom or sulfur atom, X denotes an oxygen atom or sulfur atom, W denotes an aralkyl group, phenyl group, naphthyl group, 5- or 6-membered heterocycle and its condensed ring (these may have one or more substituents on aromatic ring or heterocycle), lower alkyl group which may be substituted with halogen atom or cycloalkyl group, and $R^3$ denotes an aralkyl group, phenyl group, naphthyl group, 5- or 6-membered heterocycle and its condensed ring (these may have one or more substituents on aromatic ring or heterocycle), hydrogen atom, lower alkyl group which may be substituted with halogen atom or cycloalkyl group), or general formula (4-c)

(4-c)

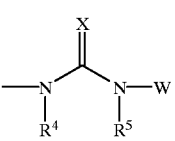

(wherein X denotes an oxygen atom or sulfur atom, W denotes an aralkyl group, phenyl group, naphthyl group, 5- or 6-membered heterocycle and its condensed ring (these may have one or more substituents on aromatic ring or heterocycle), lower alkyl group which may be substituted with halogen atom or cycloalkyl group, and $R^4$ and $R^5$ identically or differently denote aralkyl groups, phenyl groups, naphthyl groups, 5- or 6-membered heterocycles and their condensed rings (these may have one or more substituents on aromatic rings or heterocycles), hydrogen atoms, lower alkyl groups which may be substituted with halogen atom or cycloalkyl groups), ring B denotes a saturated or unsaturated heterocycle and its condensed ring (these may have one or more substituents on heterocycle or condensed ring) which may additionally contain one or two oxygen, nitrogen or sulfur atoms, and m denotes 0 or 1, A denotes a single bond, lower alkylene or lower alkenylene, R denotes a nitro group, amino group which may be substituted, or general formula (7)

(7)

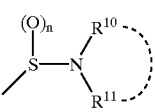

(wherein $R^{10}$ and $R^{11}$ identically or differently denote aralkyl groups, phenyl groups, 5- or 6-membered heterocycles and their condensed rings (these may have one or more substituents on aromatic rings or heterocycles), hydrogen atoms, lower alkyl groups which may be substituted with halogen atom or cycloalkyl groups, or $R^{10}$ and $R^{11}$ may form a ring (which may additionally contain one or two heteroatoms) together with nitrogen atom), and n denotes 1 to 2), $R^1$ denotes an aralkyl group, phenyl group, naphthyl group, 5- or 6-membered heterocycle and its condensed ring (these may have one or more substituents on aromatic ring or heterocycle), hydrogen atom, lower alkyl group which may be substituted with halogen atom or cycloalkyl group, and $R^2$ denotes a hydroxyl group, lower alkoxy group, or general formula (6)

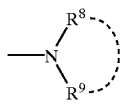

(6)

(wherein $R^8$ and $R^9$ identically or differently denote aralkyl groups, phenyl groups, 5- or 6-membered heterocycles and their condensed rings (these may have one or more substituents on aromatic rings or heterocycles), hydrogen atoms, lower alkyl groups which may be substituted with halogen atom or cycloalkyl groups, or $R^8$ and $R^9$ may form a ring (which may additionally contain one or two heteroatoms) together with nitrogen atom, or either of $R^8$ and $R^9$ denotes a hydrogen atom while the other denotes a phenyloxy group or aralkyloxy group (these may have one or more substituents on aromatic ring), hydroxyl group or lower alkoxy group)], and their addition salts have excellent antagonism against AMPA receptor, leading to the completion of the invention.

In the general formula (1-a) of the inventive compounds, preferably, compounds wherein $R^1$ is a hydrogen atom, $R^2$ is a hydroxyl group or lower alkoxy group, A is a single bond, and, in the general formula (4) for L, V is a lower alkylene and T is general formula (4-a) or general formula (4-c) can be mentioned.

As these preferable compounds, following compounds, namely,

Ethyl 3,4-dihydro-7-(4-(hydroxymethyl)imidazole-1-yl)-3-oxo-6-trifluoromethylquinoxaline-2-carboxylate, Ethyl 3,4-dihydro-7-(4-((N-(4-ethoxycarbonylphenyl)carbamoyloxy)methyl)imidazole-1-yl)-3-oxo-6-trifluoromethylquinoxaline-2-carboxylate, Ethyl 3,4-dihydro-7-(4-(((4-ethoxycarbonyl-2-fluorophenyl)carbamoyloxy)methyl)imidazole-1-yl)-3-oxo-6-trifluoromethylquinoxaline-2-carboxylate, 7-(4-((N-(4-Carboxyphenyl)carbamoyloxy)methyl)imidazole-1-yl)-3,4-dihydro-3-oxo-6-trifluoromethylquinoxaline-2-carboxylic acid, Ethyl 3,4-dihydro-7-(4-((N-(4-ethoxycarbonyl-2-fluorophenyl)carbamoyloxy)methyl)imidazole-1-yl)-3-oxo-6-trifluoromethylquinoxaline-2-carboxylate, 7-(4-((N-(4-Carboxy-2-fluorophenyl)carbamoyloxy)methyl)imidazole-1-yl)-3,4-dihydro-3-oxo-6-trifluoromethyl-quinoxaline-2-carboxylic acid, Ethyl 3,4-dihydro-7-(4-((N-(4-ethoxycarbonylmethylphenyl)carbamoyloxy)methyl)imidazole-1-yl)-3-oxo-6-trifluoromethylquinoxaline-2-carboxylate, 7-(4-((N-(4-Carboxymethylphenyl)carbamoyloxy)methyl)imidazole-1-yl)-3,4-dihydro-3-oxo-6-trifluoromethylquinoxaline-2-carboxylic acid, Ethyl 3,4-dihydro-7-(4-(((4-ethoxycarbonylphenyl)aminocarbonylamino)methyl)imidazole-1-yl)-3-oxo-6-trifluoromethylquinoxaline-2-carboxylate, 7-(4-(((4-Carboxyphenyl)aminocarbonylamino)methyl)imidazole-1-yl)-3,4-dihydro-3-oxo-6-trifluoromethylquinoxaline-2-carboxylic acid, Ethyl 7-(3-formylpyrrole-1-yl)-3-oxo-1,2,3,4-tetrahydro-6-trifluoromethylquinoxaline-2-carboxylate, Ethyl 7-(3-(aminomethyl)pyrrole-1-yl)-3-oxo-1,2,3,4-tetrahydro-6-trifluoromethylquinoxaline-2-carboxylate hydrochloride, Ethyl 7-(3-(((4-ethoxycarbonylphenyl)aminocarbonylamino)methyl)pyrrole-1-yl)-3-oxo-1,2,3,4-tetrahydro-6-trifluoromethylquinoxaline-2-carboxylate, Ethyl 7-(3-(((4-ethoxycarbonylphenyl-2-fluorophenyl)aminocarbonylamino)methyl)pyrrole-1-yl)-3-oxo-1,2,3,4-tetrahydro-6-trifluoromethylquinoxaline-2-carboxylate, Ethyl 3,4-dihydro-7-(3-(((4-ethoxycarbonylphenyl)aminocarbonylamino)methyl)pyrrole-1-yl)-3-oxo-6-trifluoromethylquinoxaline-2-carboxylate, 7-(3-(((4-Carboxyphenyl)aminocarbonylamino)methyl)pyrrole-1-yl)-3,4-dihydro-3-oxo-6-trifluoromethylquinoxaline-2-carboxylic acid, Ethyl 3,4-dihydro-7-(3-(((4-ethoxycarbonyl-2-fluorophenyl)aminocarbonylamino)methyl)pyrrole-1-yl)-3-oxo-6-trifluoromethylquinoxaline-2-carboxylate, 7-(3-(((4-Carboxy-2-fluorophenyl)aminocarbonylamino)methyl)pyrrole-1-yl)-3,4-dihydro-3-oxo-6-trifluoromethylquinoxaline-2-carboxylic acid, and the like can be mentioned.

In the general formula (1-b) of the inventive compounds, preferably, compounds wherein R is nitro group, $R^1$ is hydrogen atom, $R^2$ is hydroxyl group, A is single bond, and, in the general formula (4) for L, V is lower alkylene and T is general formula (4-a) or general formula (4-c) can be mentioned.

As these preferable compounds, following compounds, namely, 3,4-Dihydro-6-nitro-7-(4-((N-isopropylcarbamoyloxy)methyl)imidazolyl)-3-oxo-quinoxaline-2-carboxylic acid, 7-(4-((N-n-Butylcarbamoyloxy)methyl)imidazolyl)-3,4-dihydro-6-nitro-3-oxoquinoxaline-2-carboxylic acid, 7-(4-((N-t-Butylcarbamoyloxy)methyl)imidazolyl)-3,4-dihydro-6-nitro-3-oxoquinoxaline-2-carboxylic acid, 3,4-Dihydro-6-nitro-3-oxo-7-(4-((N-phenylcarbamoyloxy)methyl)imidazolyl)quinoxaline-2-carboxylic acid, 7-(4-((N-(4-Isopropylphenyl)carbamoyloxy)methyl)imidazolyl)-3,4-dihydro-6-nitro-3-oxoquinoxaline-2-carboxylic acid, 7-(4-((N-(2-Bromophenyl)carbamoyloxy)methyl)imidazolyl)-3,4-dihydro-6-nitro-3-oxoquinoxaline-2-carboxylic acid, 7-(4-((N-(3-Bromophenyl)carbamoyloxy)methyl)imidazolyl)-3,4-dihydro-6-nitro-3-oxoquinoxaline-2-carboxylic acid, 7-(4-((N-(4-Bromophenyl)carbamoyloxy)methylbimidazolyl)-3,4-dihydro-6-nitro-3-oxoquinoxaline-2-carboxylic acid, 7-(4-((N-(2-Chlorophenyl)carbamoyloxy)methyl)imidazolyl)-3,4-dihydro-6-nitro-3-oxoquinoxaline-2-carboxylic acid, 7-(4-((N-(3-Chlorophenyl)carbamoyloxy)methyl)imidazolyl)-3,4-dihydro-6-nitro-3-oxoquinoxaline-2-carboxylic acid, 7-(4-((N-(4-Chlorophenyl)carbamoyloxy)methyl)
  imidazolyl)-3,4-dihydro-6-nitro-3-oxoquinoxaline-2-
  carboxylic acid,
7-(4-((N-(2,3-Dichlorophenyl)carbamoyloxy)methyl)
  imidazolyl)- 3,4-dihydro-6-nitro-3-oxoquinoxaline-2-
  carboxylic acid,
7-(4-((N-(2,4-Dichlorophenyl)carbamoyloxy)methyl)
  imidazolyl)-3,4-dihydro-6-nitro-3-oxoquinoxaline-2-
  carboxylic acid,
7-(4-((N-(2,5-Dichlorophenyl)carbamoyloxy)methyl)
  imidazolyl)-3,4-dihydro-6-nitro-3-oxoquinoxaline-2-
  carboxylic acid,
7-(4-((N-(2,6-Dichlorophenyl)carbamoyloxy)methyl)
  imidazolyl)-3,4-dihydro-6-nitro-3-oxoquinoxaline-2-
  carboxylic acid,
7-(4-((N-(3,4-Dichlorophenyl)carbamoyloxy)methyl)
  imidazolyl)-3,4-dihydro-6-nitro-3-oxoquinoxaline-2-
  carboxylic acid,
7-(4-((N-(3,5-Dichlorophenyl)carbamnoyloxy)methyl)
  imidazolyl)-3,4-dihydro-6-nitro-3-oxoquinoxaline-2-
  carboxylic acid,
3,4-Dihydro-7-(4-((N-(4-methoxyphenyl)carbamoyloxy)
  methyl)imidazolyl)-6-nitro-3-oxoquinoxaline-2-
  carboxylic acid,
3,4-Dihydro-7-(4-((N-(2-fluorophenyl)carbamoyloxy)
  methyl)imidazolyl)-6-nitro-3-oxoquinoxaline-2-
  carboxylic acid,
3,4-Dihydro-7-4--((N-(3-fluorophenyl)carbamoyloxy)
  methyl)imidazolyl)-6-nitro-3-oxoquinoxaline-2-
  carboxyic acid,
3,4-Dihydro-7-(4-((N-(4-fluorophenyl)carbamoyloxy)
  methyl)imidazolyl)-6-nitro-3-oxoquinoxaline-2-
  carboxylic acid,
3,4-Dihydro-7-(4-((N-(2-methyiphenyl)carbamoyloxy)
  methyl)imidazolyl)-6-nitro-3-oxoquinoxaline-2-
  carboxylic acid,
3,4-Dihydro-7-(4-((N-(3-methylphenyl)carbamoyloxy)
  methyl)imidazolyl)- 6-nitro-3-oxoquinoxaline-2-
  carboxylic acid,
3,4-Dihydro-7-(4-((N-(4-methylphenyl)carbamoyloxy)
  methyl)imidazolyl)-6-nitro-3-oxoquinoxaline-2-
  carboxylic acid,
3,4-Dihydro-6-nitro-3-oxo-7-(4-((N-(2-
  trifluoromethylphenyl)carbamoyloxy)methyl)
  imidazolyl)-quinoxaline2-carboxylic acid,
3,4-Dihydro-6-nitro-3-oxo-7-(4-((N-(3-
  trifluoromethylphenyl)carbamoyloxy)methyl)
  imidazolyl)quinoxaline-2-carboxylic acid,
3,4-Dihydro-6-nitro-3-oxo-7-(4-((N-(4-
  trifluoromethylphenyl)carbamoyloxy)methyl)
  imidazolyl)quinoxaline-2-carboxylic acid,
3,4-Dihydro-6-nitro-3-oxo-7-(4-((N-(4-
  trifluoromethoxyphenyl)carbamoyloxy)methyl)
  imidazolyl)quinoxaline-2-carboxylic acid,
7-(4-((N-(3-Carboxyphenyl)carbamoyloxy)methyl)
  imidazolyl)-3,4-dihydro-6-nitro-3-oxoquinoxaline-2-
  carboxylic acid,
7-(4-((N-(4-Carboxyphenyl)carbamoyloxy)methyl)
  imidazolyl)-3,4-dihydro-6-nitro-3-oxoquinoxaline-2-
  carboxylic acid,
3,4-Dihydro-7-(4-(((2-fluorophenyl)
  aminocarbonylamino)methyl)imidazolyl)-6-nitro-3-
  oxoquinoxaline-2-carboxylic acid,
7-(4-(((4-Carboxyphenyl)aminocarbonylamino)methyl)
  imidazolyl)-3,4-dihydro-6-nitro-3-oxoquinoxaline-2-
  carboxylic acid,
Sodium 7-(4-((N-benzylcarbamoyloxy)methyl)
  imidazolyl)-3,4-dihydro-6-nitro-3-oxoquinoxaline-2-
  carboxylate,
3,4-Dihydro-6-nitro-3-oxo-7-(3-((N-
  phenylcarbamoyloxy)methyl)-4-pyridone-1-yl)
  quinoxaline-2-carboxylic acid,
7-(3-((N-(2-Bromophenyl)carbamoyloxy)methyl)-4-
  pyridone-1-yl)-3,4-dihydro-6-nitro-3-oxoquinoxaline-
  2-carboxylic acid,
7-(3-((N-(3-Bromophenyl)carbamoyloxy)methyl)-4-
  pyridone-1-yl)-3,4-dihydro-6-nitro-3-oxoquinoxaline-
  2-carboxylic acid,
7-(3-((N-(4-Bromophenyl)carbamoyloxy)methyl)-4-
  pyridone-1-yl)-3,4-dihydro-6-nitro-3-oxoquinoxaline-
  2-carboxylic acid,
7-(3-((N-(3-Carboxyphenyl)carbamoyloxy)methyl)-4-
  pyridone-1-yl)-3,4-dihydro-6-nitro-3-oxoquinoxaline-
  2-carboxylic acid,
3,4-Dihydro-6-nitro-3-oxo-7-(3-
  (phenylaminocarbonylamino)-4-pyridone-1-yl)
  quinoxaline-2-carboxylic acid,
7-(3-((2-Bromophenyl)aminocarbonylamino)-4-
  pyridone-1-yl)-3,4-dihydro-6-nitro-3-oxoquinoxaline-
  2-carboxylic acid,
7-(3-((3-Bromophenyl)aminocarbonylamino)-4-
  pyridone-1-yl)-3,4-dihydro-6-nitro-3-oxoquinoxaline-
  2-carboxylic acid,
7-(3-((4-Bromophenyl)aminocarbonylamino)-4-
  pyridone-1-yl)-3,4-dihydro-6-nitro-3-oxoquinoxaline-
  2-carboxylic acid,
3,4-Dihydro-7-(3-((4-fluorophenyl)
  aminocarbonylamino)-4-pyridone-1-yl)-6-nitro-3-
  oxoquinoxaline-2-carboxylic acid,
3,4-Dihydro-7-(3-((4-methylphenyl)
  aminocarbonylamino)-4-pyridone-1-yl)-6-nitro-3-
  oxoquinoxaline-2-carboxylic acid,
3,4-Dihydro-7-(3-((4-methoxyphenyl)
  aminocarbonylamino)-4-pyridone-1-yl)-6-nitro-3-
  oxoquinoxaline-2-carboxylic acid,
7-(3-(Benzylaminocarbonylamino)-4-pyridone-1-yl)-3,4-
  dihydro-6-nitro-3-oxoquinoxaline-2-carboxylic acid,
7-(3-((4-Bromobenzyl)carbonylamino)-4-pyridone-1-yl)-
  3,4-dihydro-6-nitro-3-oxoquinoxaline-2-carboxylic
  acid,
7-(3-((4-Bromophenyl)carbonylamino)-4-pyridone-1-yl)-
  3,4-dihydro-6-nitro-3-oxoquinoxaline-2-carboxylic
  acid,
Ethyl 3-ethoxy-7-(4-(hydroxymethyl)imidazolyl)-6-
  nitroquinoxaline-2-carboxylate,
Ethyl 7-(4-((N-(4-bromophenyl)carbamoyloxy)methyl)
  imidazolyl)-3-ethoxy-6-nitroquinoxaline-2-
  carboxylate,
Ethyl 3-ethoxy-6-nitro-7-(4-(trifluoroacetamidomethyl)
  imidazolyl)quinoxaline-2-carboxylate,
Ethyl 3-ethoxy-7-(3-(hydroxymethyl)-4-pyridone-1-yl)-
  6-nitroquinoxaline-2-carboxylate,
Ethyl 7-(3-amino-4-pyridone-1-yl)-3-ethoxy-6-
  nitroquinoxaline-2-carboxylate,
Ethyl 7-(3-((4-bromophenyl)aminocarbonylamino)-4-
  pyridone-1-yl)-3-ethoxy-6-nitroquinoxaline-2-
  carboxylate, and the like can be mentioned.

In the description of the general formula (1) of the invention, for the substituents in the phrases of "phenyl group, naphthyl group, 5- or 6-membered heterocycle and its condensed ring (these may have one or more substituents on aromatic ring or heterocycle)", "aralkyl group, phenyl group, naphthyl group, 5- or 6-membered heterocycle and its condensed ring (these may have one or more substituents on aromatic ring or heterocycle)", "ring B denotes a saturated or unsaturated heterocycle and its condensed ring (these may have one or more substituents on aromatic ring or heterocycle) which may additionally contain one or two oxygen, nitrogen or sulfur atoms", "aralkyl group, phenyl group, 5- or 6-membered heterocycle and its condensed ring (these may have one or more substituents on aromatic ring or heterocycle)", "phenyloxy group, aralkyloxy group (these may have one or more substituents on aromatic ring or heterocycle)", "phenyl group which may have one or more substituents or aralkyl group which may have one or more substituents", and "phenyl group which may have one or more substituents or naphthyl group", halogen atom, hydroxyl group, lower alkyl group which may be substituted with halogen atom, lower alkoxy group, lower alkylthio group, lower alkoxycarbonyl group, nitro group, amino group, cyano group, carboxyl group, aldehyde group, lower alkyl group with carboxyl group or the like are mentioned, for "lower alkyl groups", straight chain or branched ones with carbon atoms of 1 to 6 such as methyl, ethyl, n-propyl, iso-propyl or the like are mentioned, for "cycloalkyl groups", ones with carbon atoms of 3 to 7 such as cyclopropyl, cyclopentyl, cyclohexyl or the like are mentioned, for "halogen atoms", fluorine, chlorine, bromine and iodine are mentioned, for "lower alkoxy groups", straight chain or branched ones with carbon atoms of 1 to d 4 such as methoxy, ethoxy, propoxy or the like are mentioned, for "lower alkylthio groups", straight chain or branched ones with carbon atoms of 1 to 6 such as methylthio, ethylthio, propylthio or the like are mentioned, for "lower alkoxycarbonyl groups", straight chain or branched ones with carbon atoms of 1 to 4 such as methoxycarbonyl, ethoxycarbonyl or the like are mentioned, for "aralkyloxy groups", benzyloxy, phenylethyloxy, phenylpropyloxy or the like are mentioned, for "aralkylthio groups", benzylthio, phenylethylthio, phenylpropylthio or the like are mentioned, and, for "amino groups which may be substituted", amino groups which may be substituted with acyl group or arylsulfonyl group, for example, acetyl, methanesulfonyl, phenylsulfonyl or the like, or which may be substituted with lower alkyl group which may be substituted with one or two halogen atoms, phenyl group which may have one or two substituents and aralkyl group which may have one or two substituents are mentioned.

The substituents referring to so here indicate "substituents" as defined above.

Further, in the description, "heterocycles" in the phrases of "phenyl group, naphthyl group, 5- or 6-membered heterocycle and its condensed ring (these may have one or more substituents on aromatic ring or heterocycle)", "aralkyl group, phenyl group, naphthyl group, 5- or 6-membered heterocycle and its condensed ring (these may have one or more substituents on aromatic ring or heterocycle), and "aralkyl group, phenyl group, 5- or 6-membered heterocycle and its condensed ring (these may have one or more substituents on aromatic ring or heterocycle)", are saturated or unsaturated monocyclic or polycyclic heterocycle groups which may have one or more substituents and which can contain one or two oxygen, nitrogen or sulfur atoms, and, for example, pyrrolidyl, piperidyl, piperazyl, morpholyl, thiomorpholyl, furanyl, thienyl, pyrazolyl, imidazolyl, oxazolyl, thiazolyl, pyridyl, pyrimidyl, pyridazyl, pyrazyl or the like are mentioned, and "their condensed rings" represent condensed rings of said "heterocycles" with benzene and, for example, indolyl, tetrahydroquinolyl, benzoxazolidinyl, benzothiazolidinyl, benzofuranyl, benzothienyl, benzimidazolyl, quinolyl, isoquinolyl, quinazolyl, quinoxalyl, cinnolyl or the like are mentioned. Moreover, for "ring B denotes a saturated or unsaturated heterocycle and its condensed ring which may additionally contain one or two oxygen, nitrogen or sulfur atoms", said "heterocycles" and "their condensed rings" are mentioned, further they represent saturated or unsaturated heterocycles or their condensed rings which may be substituted with carbonyl group, in which carbonyl group may be substituted onto said "heterocycles" and "their condensed rings", and for example, 2-pyrrolidone, 3-pyrrolidone, 2-imidazolidinone, 2-thiazolidinone, 4-thiazolidinone, 2-oxazolidinone, 4-oxazolidinone, 2-pyridone, 4-pyridone, 2-pyrimidinone, 4-pyrimidinone, 2,4-pyrimidinedione, 2-quinolone, 4-quinolone, etc. are mentioned. Moreover, "rings (which may additionally contain one or two heteroatoms) may be formed together with nitrogen atom" are saturated monocyclic or polycyclic heterocycle groups which may additionally contain one or two nitrogen, oxygen or sulfur atoms, and, for example, pyrrolidyl, piperidyl, piperazyl, morpholyl, thiomorpholyl, indolyl, tetrahydroquinolyl, etc. are mentioned.

The compounds of the invention can be prepared through, for example, processes shown below.

Compounds, $R^1$ being hydrogen atom, among the compounds represented by the general formula (1) can be synthesized by reacting compounds represented by a general formula (10)

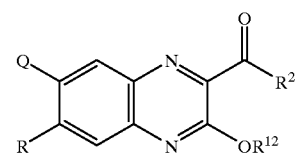

(10)

(wherein Q, R and $R^2$ are as described above, and $R^{12}$ denotes a lower alkyl group which may be substituted with halogen atom or aralkyl group which may have one or more substituents), for 0.5 to 72 hours at 20 to 120° C. without solvent or in a suitable solvent, for example, water, acetic acid, methanol or the like, using a suitable acid, for example, hydrochloric acid, sulfuric acid, hydrobromic acid, trifluoroacetic acid or the like.

Moreover, compounds, $R^1$ being hydrogen atom, among the compounds represented by the general formula (1) can also be synthesized, in the case of $R^2$ being lower alkoxy group among the compounds represented by the general formula (10)

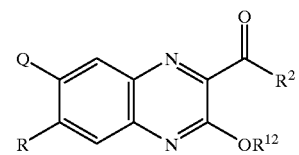

(10)

(wherein Q, R, $R^2$ and $R^{12}$ are as described above), by reacting those compounds for 0.5 to 10 hours at 20 to 100° C. in a suitable solvent of water, methanol, ethanol or the like, using a suitable alkali, for example, potassium hydroxide, lithium hydroxide or the like to convert to carboxylic acid, and then by reacting for 0.5 to 72 hours at 20 to 120° C. without solvent or in a suitable solvent, for example, water, acetic acid, methanol or the like using a suitable acid, for example, hydrochloric acid, sulfuric acid, hydrobromic acid, trifluoroacetic acid or the like.

Moreover, compounds, $R^1$ being hydrogen atom, among the compounds represented by the general formula (1) can also be synthesized, in the case of $R^2$ being lower alkoxy group among the compounds represented by the general formula (10)

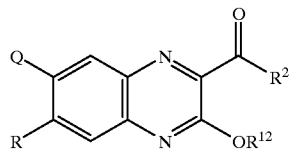
(10)

(wherein Q, R, $R^2$ and $R^{12}$ are as described above), by reacting those compounds for 3 to 72 hours at 20 to 120° C. without solvent or in a suitable solvent, for example, water, acetic acid, methanol or the like, using a suitable acid, for example, hydrochloric acid, sulfuric acid, hydrobromic acid, trifluoroacetic acid or the like to convert to amide-ester form, and then by reacting for 0.5 to 10 hours at 20 to 100° C. in a solvent of water, methanol, ethanol or the like, using a suitable alkali, for example, potassium hydroxide, sodium hydroxide or the like.

Moreover, when converting compounds, $R^2$ being lower alkoxy group, to compounds, $R^2$ being hydroxyl group, among the compounds represented by the general formula (1), the latter compounds can also be synthesized by reacting the former compounds for 0.5 to 10 hours at 20 to 100° C. in a suitable solvent of water, methanol, ethanol or the like, using a suitable alkali, for example, potassium hydroxide, lithium hydroxide or the like.

Moreover, compounds, $R^1$ being hydrogen atom, among the compounds represented by the general formula (1) can also be converted to compounds, $R^1$ being substituted with lower alkyl group, aralkyl group (which may have one or more substituents) or cyclic alkyl group, by reacting with alkyl halide, for example, methyl iodide or the like, aralkyl halide, for example, benzyl chloride, 4-methoxybenzyl chloride or the like or cyclic alkyl halide, for example, cyclopentyl bromide, cyclohexyl bromide or the like for 2 to 10 hours at 20 to 120° C. in a suitable solvent, for example, tetrahydrofuran, dioxane, N,N-dimethylformamide, N,N-dimethylacetamide or the like, using a suitable base, for example, sodium hydride, sodium carbonate, potassium carbonate or the like.

Moreover, compounds represented by the general formula (1) can be synthesized by reacting compounds represented by a general formula (11)

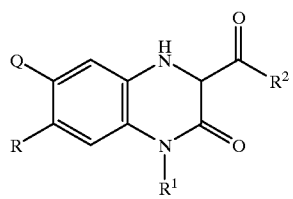
(11)

(wherein Q, R, $R^1$ and $R^2$ are as described above), for 1 to 24 hours at 20 to 120° C. in a suitable solvent, for example, tetrahydrofuran, dioxane, N,N-dimethylformamide, N,N-dimethylacetamide, N-methylpyrrolidone, acetonitrile, benzene, toluene or the like, using an oxidizing agent, for example, DDQ (dichlorodicyanoquinone).

Moreover, compounds represented by the general formula (1) can also be synthesized by reacting compounds represented by the general formula (11) for 1 to 72 hours at 20 to 120° C. in a suitable solvent, for example, tetrahydrofuran, dioxane, N,N-dimethylformamide, N,N-dimethylacetamide, N-methylpyrrolidone, acetonitrile, ethanol, toluene or the like, using a suitable base, for example, triethylamine, diisopropylethylamine, sodium carbonate, potassium carbonate or the like.

Moreover, compounds, L being general formula (4) and, for T, W in the general formula (4-a) and general formula (4-c) being aralkyl group, phenyl group, naphthyl group, 5- or 6-membered heterocycle or its condensed ring (these may have one or more substituents on aromatic ring or heterocycle), among the compounds, Q in the general formula (1) being represented by the general formula (3), can also be synthesized by reacting compounds represented by a general formula (12)

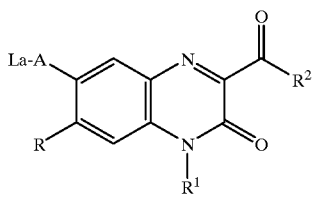
(12)

(wherein La is general formula (13)

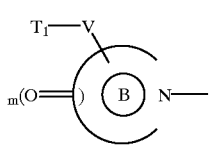
(13)

(wherein $T_1$ denotes a hydroxyl group, thiol group or amino group which may be substituted, and A, R, $R^1$, $R^2$, ring B, V and m are as described above), with compounds represented by a general formula (14)

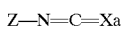
(14)

(wherein Z denotes an aralkyl group, phenyl group, naphthyl group, 5- or 6-membered heterocycle and its condensed ring (these may have one or more substituents on aromatic ring or heterocycle), lower alkyl group which may be substituted with halogen atom or cyclic alkyl group, and Xa denotes an oxygen or sulfur atom), for 0.5 to 15 hours at 20 to 120° C. in a suitable solvent, for example, methylene chloride, tetrahydrofuran, dioxane, N,N-dimethylformamide, N,N-dimethylacetamide, N-methylpyrrolidone, acetonitrile, benzene, toluene or the like, without base or using a suitable organic base, for example, triethylamine or the like.

Also, they can be synthesized by converting compounds represented by a general formula (15)

(15)

(wherein Z denotes an aralkyl group, phenyl group, naphthyl group, 5- or 6-membered heterocycle and its condensed ring (these may have one or more substituents on aromatic ring or heterocycle), lower alkyl group which may be substituted with halogen atom or cyclic alkyl group, $A_1$ denotes a single bond, lower alkylene, lower alkenylene or lower alkynylene, and D denotes an amino group, carboxyl group, amide group or lower alkoxycarbonyl group), in place of general formula (14), to isocyanic (isothiocyanic) ester or carbamoyl chloride through known process, and by reacting with general formula (12) similarly to general formula (14).

For example, in the case of D being amino group, they can be converted to carbamoyl chloride or isocyanic (isothiocyanic) ester by reacting with phosgene (thiophosgene), phosgene dimer (2,2,2-trichloromethyl chloroformate) or its homolog (4-nitrophenyl chloroformate or the like) for 1 to 5 hours at −10 to 50° C. in a suitable solvent, for example, tetrahydrofuran, dioxane, benzene, toluene or the like, without base or using a suitable organic base, for example, triethylamine or the like.

Further, they can be converted to isocyanic ester by changing carboxyl group to acid azide and then using Crutius rearrangement or Schmidt rearrangement in the case of D being carboxyl group, and using Hofmann rearrangement in the case of D being amide group. Moreover, in the case of D being carboxyl group, they can also be converted to isocyanic ester in one pot, using DPPA (diphenylphosphoryl azide).

Moreover, compounds, L being general formula (4), among the compounds, Q in the general formula (1) being represented by the general formula (3), can also be synthesized by reacting compounds represented by a general formula (16)

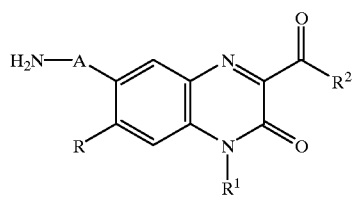

(16)

(wherein A, R, $R^1$ and $R^2$ are as described above), with compounds represented by a general formula (17)

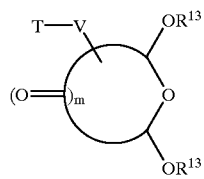

(17)

(wherein T, V, and m are as described above, and $R^{13}$ denotes a lower alkyl group which may be substituted with halogen atom or aralkyl group which may have one or more substituents), for 0.5 to 5 hours at 20 to 120° C. without solvent or in a suitable solvent, for example, tetrahydrofuran, benzene, toluene, acetic acid or the like, using a suitable inorganic or organic acid, for example, hydrochloric acid, sulfuric acid, p-toluenesulfonic acid or the like.

Moreover, compounds, L being general formula (4), among the compounds, Q in the general formula (1) being represented by the general formula (3), can also be synthesized by reacting compounds represented by a general formula (20)

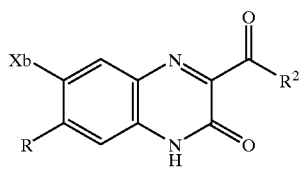

(20)

(wherein R and $R^2$ are as described above, and Xb denotes a halogen atom), or compounds represented by a general formula (20-a)

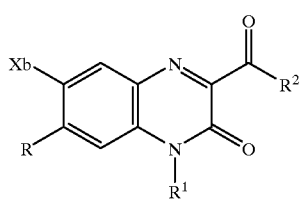

(20-a)

(wherein R, $R^2$ and Xb are as described above, and $R^1$ denotes a lower alkyl group or aralkyl group which may have one or more substituents), which are obtained by reacting that general formula (20) with alkyl halide, for example, methyl iodide or the like, or aralkyl halide, for example, 4-methoxybenzyl chloride or the like for 2 to 10 hours at 20 to 120° C. in a suitable solvent, for example, tetrahydrofuran, dioxane, N,N-dimethylformamide, N,N-dimethylacetamide or the like, using a suitable base, for example, sodium hydride, sodium carbonate, potassium carbonate or the like, with compounds represented by a general formula (19)

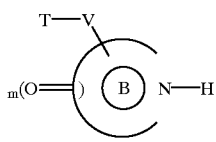

(19)

(wherein T, V, ring B and m are as described above) for 0.5 to 24 hours at 20 to 160° C. without solvent or in a suitable solvent, for example, tetrahydrofuran, dioxane, N,N-dimethylformamide, N,N-dimethylacetamide, N-methylpyrrolidone, acetonitrile, benzene, toluene or the like, without base or using a suitable inorganic or organic base, for example, sodium hydride, sodium carbonate, potassium carbonate, triethylamine or the like.

Moreover, compounds, Q in the general formula (1) being general formula (2) or general formula (5), can also be synthesized by reacting compounds represented by the general formula (20)

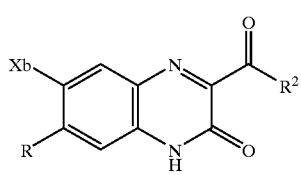

(20)

(wherein R, $R^2$ and Xb are as described above), or compounds represented by the general formula (20-a)

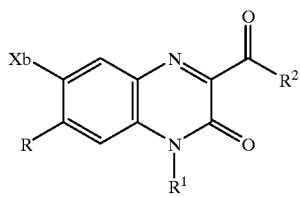

(20-a)

(wherein R, $R^1$, $R^2$ and Xb are as described above), which are obtained by reacting that general formula (20) with alkyl halide, for example, methyl iodide or the like, or aralkyl halide, for example, 4-methoxybenzyl chloride or the like for 2 to 10 hours at 20 to 120° C. in a suitable solvent, for example, tetrahydrofuran, dioxane, N,N-dimethylformamide, N,N-dimethylacetamide or the like, using a suitable base, for example, sodium hydride, sodium carbonate, potassium carbonate or the like, with compounds represented by a general formula (13-a)

(13-a)

(wherein Ar and P are as described above), or a general formula (13-b)

(13-b)

(wherein $R^6$ and $R^7$ are as described above), for 0.5 to 24 hours at 20 to 160° C. without solvent or in a suitable solvent, for example, tetrahydrofuran, dioxane, N,N-dimethylformamide, N,N-dimethylacetamide, N-methylpyrrolidone, acetonitrile, benzene, toluene or the like, without base or using a suitable inorganic or organic base, for example, sodium hydride, sodium carbonate, potassium carbonate, triethylamine or the like.

Moreover, compounds, L being general formula (4) and A being lower alkylene, among the compounds, Q in the general formula (1) being represented by the general formula (3), can also be synthesized by reacting compounds represented by a general formula (18)

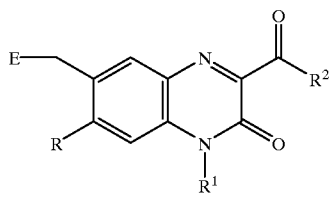

(18)

(wherein R, $R^1$ and $R^2$ are as described above, and E denotes a halogen atom), with compounds represented by a general formula (19)

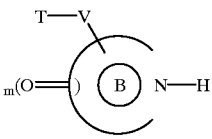

(19)

(wherein T, V, ring B and m are as described above), for 0.5 to 48 hours at 20 to 160° C. in a suitable solvent, for example, tetrahydrofuran, dioxane, N,N-dimethylformamide, N,N-dimethylacetamide, N-methylpyrrolidone, acetonitrile, benzene, toluene or the like, without base or using a suitable inorganic or organic base, for example, sodium hydride, sodium carbonate, potassium carbonate, triethylamine or the like.

Moreover, compounds, A being lower alkylene, among the compounds, Q in the general formula (1) being represented by the general formula (2) or general formula (5), can also be synthesized by reacting compounds represented by a general formula (18)

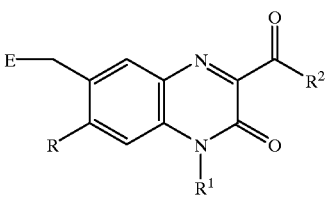

(18)

(wherein R, $R^1$, $R^2$ and E are as described above), with compounds represented by he general formula (13-a)

Ar—P—H         (13-a)

(wherein Ar and P are as described above), or the general formula (13-b)

(13-b)

(wherein $R^6$ and $R^7$ are as described above), for 1 to 24 hours at 25 to 120° C. in a suitable solvent, for example, tetrahydrofuran, N,N-dimethylformamide, benzene, toluene or the like, using a suitable inorganic or organic base, for example, sodium hydride, sodium carbonate, potassium carbonate, triethylamine or the like.

Moreover, compounds represented by the general formula (1) or general formula (12) can also be synthesized by reacting compounds represented by a general formula (21)

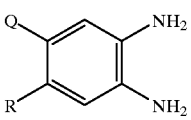

(21)

(wherein Q and R are as described above), with ketomalonic acid diester represented by a general formula (22)

(22)

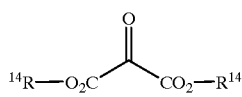

(wherein $R^{14}$ denotes a lower alkyl group), for 2 to 12 hours at 25 to 100° C. in a suitable solvent, for example, ethanol, methanol, tetrahydrofuran or the like.

Moreover, compounds, L being general formula (4) and, for T. W in the general formula (4-a) and general formula (4-c) being aralkyl group, phenyl group, naphthyl group, 5- or 6-membered heterocycle or its condensed ring (these may have one or more substituents on aromatic ring or heterocycle), among the compounds, Q in the general formula (10) being represented by the general formula (3), can also be synthesized by reacting compounds represented by a general formula (23)

(23)

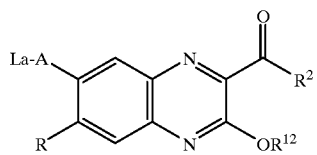

(wherein La, A, R, $R^2$ and $R^{12}$ are as described above), with compounds represented by the general formula (14)

$$Z—N=C=Xa \qquad (14)$$

(wherein Z and Xa are as described above), for 1 to 15 hours at 20 to 120° C. in a suitable solvent, for example, methylene chloride, tetrahydrofuran, dioxane, N,N-dimethylformamide, N,N-dimethylacetamide, N-methylpyrrolidone, acetonitrile, benzene, toluene or the like, without base or using a suitable organic base, for example, triethylamine, pyridine or the like.

Also, they can be synthesized by converting compounds represented by the general formula (15)

$$Z—A_1—D \qquad (15)$$

(wherein Z, $A_1$, and D are as described above), in place of general formula (14), to isocyanic (isothiocyanic) ester or carbamoyl chloride through known process, and by reacting with general formula (23) similarly to general formula (14).

For example, in the case of D being amino group, they can be converted to carbamoyl chloride or isocyanic (isothiocyanic) ester by reacting with phosgene (thiophosgene), phosgene dimer (2,2,2-trichloromethyl chloroformate) or its homolog (4-nitrophenyl chloroformate or the like) for 1 to 5 hours at –10 to 50° C. in a suitable solvent, for example, tetrahydrofuran, dioxane, benzene, toluene or the like, without base or using a suitable organic base, for example, triethylamine or the like.

Further, they can be converted to isocyanic ester by changing carboxyl group to acid azide and then using Crutius rearrangement or Schmidt rearrangement in the case of D being carboxyl group, and using Hofmann rearrangement in the case of D being amide group. Moreover, in the case of D being carboxyl group, they can also be converted to isocyanic ester in one pot, using DPPA (diphenylphosphoryl azide).

Moreover, compounds, L being general formula (4), among the compounds, Q in the general formula (10) being represented by the general formula (3), can be synthesized by reacting compounds represented by a general formula (24)

(24)

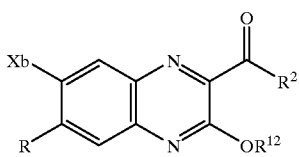

(wherein R, $R^2$, $R^{12}$ and Xb are as described above), with compounds represented by the general formula (19)

(19)

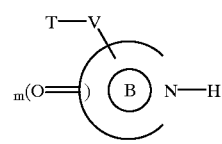

(wherein T, V ring B and m are as described above), for 0.5 to 24 hours at 20 to 160° C. without solvent or in a suitable solvent, for example, tetrahydrofuran, dioxane, N,N-dimethylformamide, N,N-dimethylacetamide, N-methylpyrrolidone, acetonitrile, benzene, toluene or the like, without base or using a suitable inorganic or organic base, for example, sodium hydride, sodium carbonate, potassium carbonate, triethylamine or the like.

Moreover, compounds, Q in the general formula (10) being represented by the general formula (2) or general formula (5), can also be synthesized by reacting compounds represented by the general formula (24)

(24)

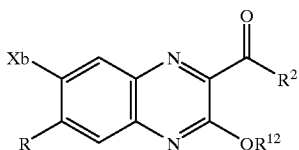

(wherein R, $R^2$, $R^{12}$ and Xb are as described above), with compounds represented by the general formula (13-a)

$$Ar—P—H \qquad (13\text{-}a)$$

(wherein Ar and P are as described above), or the general formula (13-b)

(13-b)

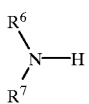

(wherein $R^6$ and $R^7$ are as described above), for 0.5 to 24 hours at 20 to 160° C. without solvent or in a suitable solvent, for example, tetrahydrofuran, dioxane, N,N-dimethylformamide, N,N-dimethylacetamide, N-methylpyrrolidone, acetonitrile, benzene, toluene or the like, without base or using a suitable inorganic or organic base, for example, sodium hydride, sodium carbonate, potassium carbonate, triethylamine or the like.

Moreover, compounds, L being general formula (4) and A being lower alkylene, among the compounds, Q in the general formula (10) being represented by the general formula (3), can also be synthesized by reacting compounds represented by a general formula (25)

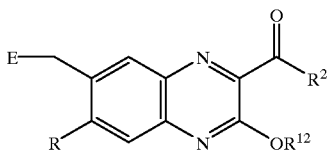
(25)

(wherein R, R², R¹² and E are as described above), with compounds represented by the general formula (19)

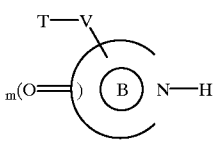
(19)

(wherein T, V, ring B and m are as described above), for 0.5 to 48 hours at 20 to 160° C. in a suitable solvent, for example, tetrahydrofuran, dioxane, N,N-dimethylformamide, N,N-dimethylacetamide, N-methylpyrrolidone, acetonitrile, benzene, toluene or the like, without base or using a suitable inorganic or organic base, for example, sodium hydride, sodium carbonate, potassium carbonate, triethylamine or the like.

Moreover, compounds, A being lower alkylene, among the compounds, Q in the general formula (10) being represented by the general formula (2) or general formula (5), can also be synthesized by reacting compounds represented by a general formula (25)

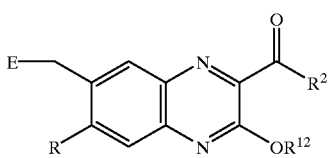
(25)

(wherein R, R², R¹² and E are as described above), with compounds represented by the general formula (13-a)

Ar—P—H  (13-a)

(wherein Ar and P are as described above), or the general formula (13-b)

(13-b)

(wherein R⁶ and R⁷ are as described above), for 1 to 24 hours at 25 to 120° C. in a suitable solvent, for example, tetrahydrofuran, N,N-dimethylformamide, benzene, toluene or the like, using a suitable inorganic or organic base, for example, sodium hydride, sodium carbonate, potassium carbonate, triethylamine or the like.

Moreover, compounds, represented by the general formula (24) can be synthesized by reacting compounds represented by the general formula (20)

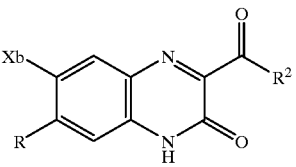
(20)

(wherein R, R² and Xb are as described above), with alkyl halide, for example, methyl iodide or the like, or aralkyl halide, for example, 4-methoxybenzyl chloride or the like for 2 to 24 hours at 20 to 120° C. in a suitable solvent for example, benzene, toluene, chloroform, methylene chloride, tetrahydrofuran or the like, using a suitable silver catalyst, for example, silver oxide, silver carbonate or the like.

Also, they can be synthesized by reacting compounds represented by the general formula (20) for 2 to 6 hours at 0 to 120° C. in a suitable solvent, for example, benzene, toluene, chloroform, methylene chloride, tetrahydrofuran or the like, using a borate, for example, tetramethyloxonium borate or the like.

Moreover, compounds R being nitro group, among the compounds represented by the general formula (20) can be synthesized by selective nitration, that is, reacting compounds represented by a general formula (26)

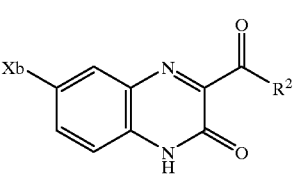
(26)

(wherein Xb and R² are as described above), for 0.5 to 5 hours at −10 to 80° C. in an acetic acid solvent, using a suitable nitrating agent, for example, concentrated nitric acid, fuming nitric acid, potassium nitrate or the like.

Moreover, compounds represented by the general formula (20) can also be synthesized by reacting compounds represented by a general formula (27)

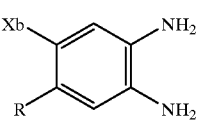
(27)

(wherein Xb and R are as described above), with ketomalonic acid diester represented by the general formula (22)

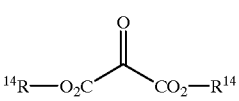
(22)

(wherein R¹⁴ is as described above), for 2 to 12 hours at 25 to 100° C. in a suitable solvent, for example, ethanol, methanol, tetrahydrofuran or the like.

Part of these compounds represented by the general formula (27) is known, and can be synthesized according to usual process.

Moreover, compounds represented by the general formula (20) can also be synthesized according to WO92-11245, Japanese Unexamined Patent Publication No. Sho 56-81569 or the like which shows following scheme.

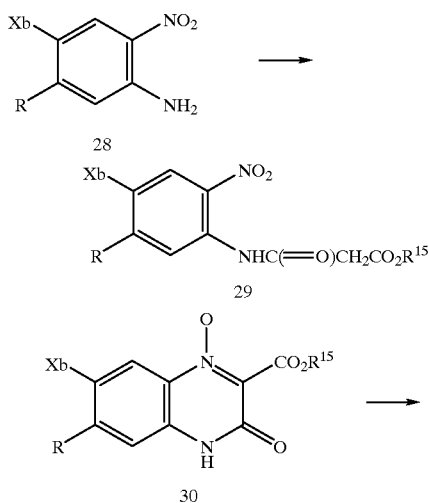

(wherein Xb and R are as described above, and $R^{15}$ denotes a lower alkyl group).

Moreover, compounds, represented by the general formula (26) can also be synthesized by reacting compounds represented by a general formula (31)

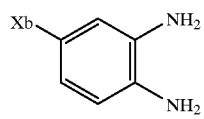

(wherein Xb is as described above), with ketomalonic acid diester represented by the general formula (22)

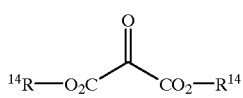

(wherein $R^{14}$ is as described above), for 2 to 12 hours at 25 to 100° C. in a suitable solvent, for example, ethanol, methanol, tetrahydrofuran or the like.

Also, part of the compounds represented by the general formula (26) is known, and can also be synthesized according to WO92-11245, Japanese Unexamined Patent Publication No. Sho 56-81569 or the like which shows following scheme.

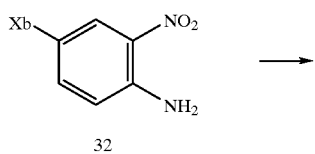

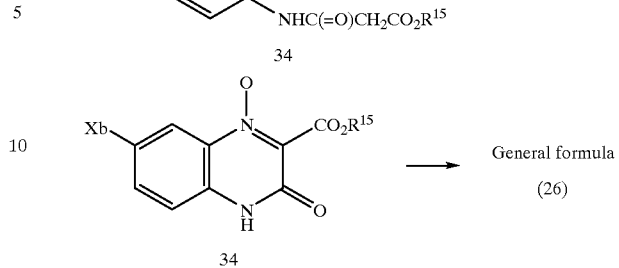

(wherein Xb and $R^{15}$ are as described above).

Moreover, compounds, L being general formula (4), among the compounds, Q in the general formula (11) being represented by the general formula (3), can also be synthesized by reacting compounds represented by a general formula (35)

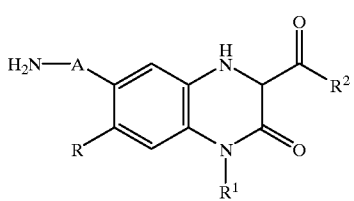

(wherein A, $R^1$ and $R^2$ are as described above), with compounds represented by the general formula (17)

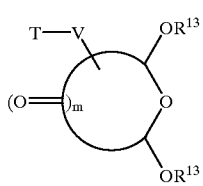

(wherein T, V, $R^{13}$ and m are as described above), for 5 to 48 hours at 20 to 80° C. without solvent or in a suitable solvent, for example, tetrahydrofuran, benzene, toluene, acetic acid or the like (to which suitable inorganic or organic acid, for example, hydrochloric acid, sulfuric acid, p-toluenesulfonic acid or the like may be added).

Moreover, compounds, L being general formula (4) and, for T, W in the general formula (4-a) and general formula (4-c) being aralkyl group, phenyl group, naphthyl group, 5- or 6-membered heterocycle or its condensed ring (these may have one or more substituents on aromatic ring or heterocycle), among the compounds, Q in the general formula (11) being represented by the general formula (3), can also be synthesized by reacting compounds represented by a general formula (36)

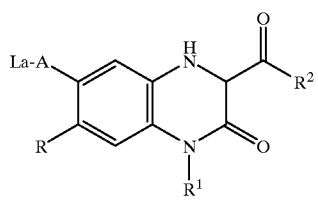

(36)

(wherein La, A, R, $R^1$ and $R^2$ are as described above), with compounds represented by the general formula (14)

$$Z\text{—}N\text{=}C\text{=}Xa \qquad (14')$$

(wherein Z and Xa are as described above), for 1 to 15 hours at 20 to 120° C. in a suitable solvent, for example, methylene chloride, tetrahydrofuran, dioxane, N,N-dimethylformamide, N,N-dimethylacetamide, N-methylpyrrolidone, acetonitrile, benzene, toluene or the like, without base or using a suitable organic base, for example, triethylamine or the like.

Also, they can be synthesized by converting compounds represented by the general formula (15)

$$Z\text{—}A_1\text{—}D \qquad (15)$$

(wherein Z, $A_1$ and D are as described above), in place of general formula (14), to isocyanic (isothiocyanic) ester or carbamyl chloride through known process, and by reacting with general formula (36) similarly to general formula (14).

For example, in the case of D being amino group, they can be converted to carbamoyl chloride or isocyanic (isothiocyanic) ester by reacting with phosgene (thiophosgene), phosgene dimer (2,2,2-trichloromethyl chloroformate) or its homolog (4-nitrophenyl chloroformate or the like) for 1 to 5 hours at −10 to 50° C. in a suitable solvent, for example, tetrahydrofuran, dioxane, benzene, toluene or the like, without base or using a suitable organic base, for example, triethylamine or the like.

Further, they can be converted to isocyanic ester by changing carboxyl group to acid azide and then using Crutius rearrangement or Schmidt rearrangement in the case of D being carboxyl group, and using Hofmann rearrangement in the case of D being amide group. Moreover, in the case of D being carboxyl group, they can also be converted to isocyanic ester in one pot, using DPPA (diphenylphosphoryl azide).

Moreover, compounds, R being trifluoromethyl group, among the compounds represented by the general formula (11) can be synthesized by reducing compounds represented by the general formula (1) through catalytic hydrogenation, that is, by hydrogenating at 20 to 80° C. and ambient pressure to 5 atm in a suitable solvent, for example, ethanol, methanol, acetic acid or the like in the presence of a suitable catalyst, for example, palladium carbon, platinum oxide, rhodium-alumina or the like.

Moreover, compounds, $R^1$ being hydrogen atom, among the compounds represented by the general formula (16) can be synthesized by reacting compounds represented by a general formula (37)

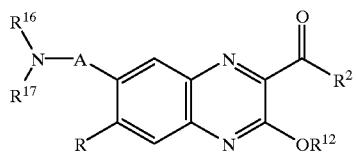

(37)

(wherein R, $R^2$, $R^{12}$ and A are as described above, and $R^{16}$ and $R^{17}$ identically or differently denote hydrogen atoms, protective groups of amino group), for 3 to 72 hours at 20 to 120° C. without solvent or in a suitable solvent, for example, water, acetic acid, methanol or the like, using a suitable acid, for example, hydrochloric acid, sulfuric acid, hydrobromic acid, trifluoroacetic acid or the like.

Moreover, compounds, $R^2$ being hydroxyl group, among the compounds represented by the general formula (16) can also be synthesized by reacting compounds represented by a general formula (38)

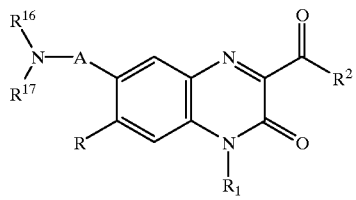

(38)

(wherein R, $R^1$, $R^2$, A, $R^{16}$ and $R^{17}$ are as described above), for 0.5 to 10 hours at 20 to 100° C. in a suitable solvent, for example, water, methanol, ethanol or the like, using a suitable alkali, for example, potassium hydroxide, sodium hydroxide or the like to convert to carboxylic acid, and then by reacting for 3 to 72 hours at 20 to 120° C. without solvent or in a suitable solvent, for example, water, acetic acid, methanol or the like, using a suitable acid, for example, hydrochloric acid, sulfuric acid, hydrobromic acid, trifluoroacetic acid or the like.

Here, compounds, A being single bond or lower alkylene, among the compounds represented by the general formula (37) can be synthesized by reacting compounds represented by the general formula (24)

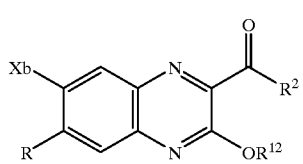

(24)

(wherein R, $R^2$, $R^{12}$ and Xb are as described above), or compounds represented by the general formula (25)

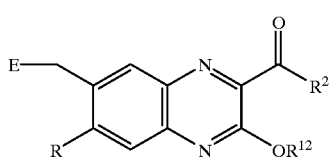

(25)

(wherein R, $R^2$, $R^{12}$ and E are as described above), with compounds represented by a general formula (39)

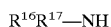 (39)

(wherein $R^{16}$ and $R^{17}$ are as described above), for 0.5 to 48 hours at 20 to 160° C. in a suitable solvent, for example, tetrahydrofuran, dioxane, N,N-dimethylformamide, N,N-dimethylacetamide, N-methylpyrrolidone, acetonitrile, benzene, toluene or the like, without base or using a suitable inorganic or organic base, for example, sodium hydride, sodium carbonate, potassium carbonate, triethylamine or the like.

Moreover, compounds represented by the general formula (25) can be synthesized by reacting compounds represented by a general formula (40)

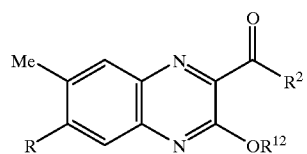 (40)

(wherein R, $R^2$ and $R^{12}$ are as described above), for 1 to 12 hours at 20 to 100° C. in a suitable solvent, for example, carbon tetrachloride, chloroform, acetic acid or the like, using a halogenating agent, for example, N-bromosuccinimide (NBS), N-chlorosuccinimide (NCS), bromine or the like.

Moreover, compounds, A being lower alkylene, among the compounds represented by the general formula (38) can be synthesized by reacting compounds represented by the general formula (18)

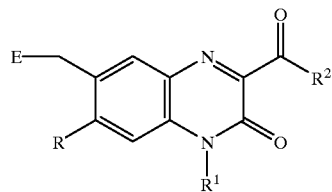 (18)

(wherein R, $R^1$, $R^2$ and E are as described above), with compounds represented by the general formula (39)

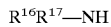 (39)

(wherein $R^{16}$ and $R^{17}$ are as described above), for 5 to 48 hours at 20 to 160° C. in a suitable solvent, for example, tetrahydrofuran, dioxane, N,N-dimethylformamide, N,N-dimethylacetamide, N-methylpyrrolidone, acetonitrile, benzene, toluene or the like, without base or using a suitable inorganic or organic base, for example, sodium hydride, sodium carbonate, potassium carbonate, triethylamine or the like.

Moreover, compounds represented by the general formula (18) can be synthesized by reacting compounds represented by a general formula (41)

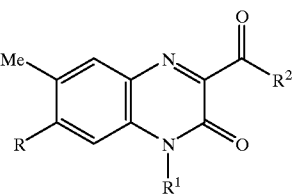 (41)

(wherein R, $R^1$ and $R^2$ are as described above), for 1 to 12 hours at 20 to 100° C. in a suitable solvent, for example, carbon tetrachloride, chloroform, acetic acid or the like, using a halogenating agent, for example, N-bromosuccinimide (NBS), N-chlorosuccinimide (NCS), bromine or the like.

Moreover, compound (42), R being trifluoromethyl group, $R^1$ being hydrogen atom and A being single bond, among the compounds represented by the general formula (35) can be synthesized through a process shown in following scheme.

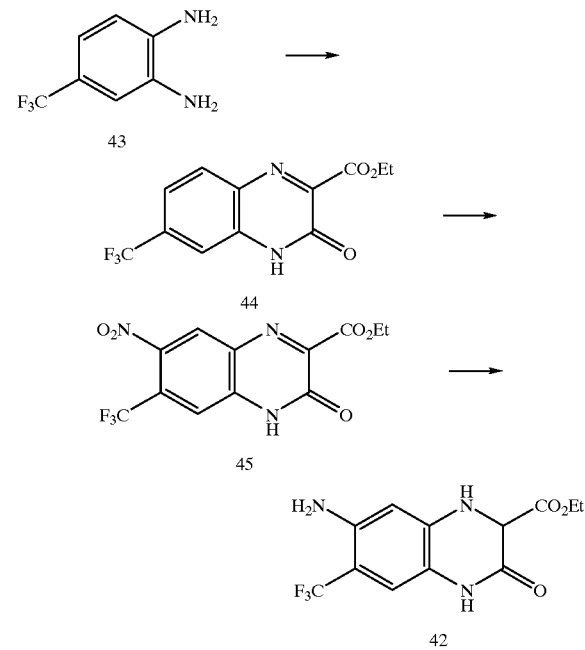

It can be synthesized by reacting compound (43) synthesizable through known process with ketomalonic acid diester (22) for 1 to 6 hours at 20 to 120° C. in a suitable solvent, for example, ethanol, methanol, tetrahydrofuran or the like to convert to compound (44), then nitrating this compound, that is, reacting for 0.5 to 6 hours at −10 to 80° C. without solvent or in a suitable solvent, for example, concentrated sulfuric acid, carbon disulfide or acetic acid, using a suitable nitrating agent, for example, concentrated nitric acid, fuming nitric acid, potassium nitrate or the like to convert to compound represented by compound (45), and reducing this through catalytic hydrogenation, that is, hydrogenating at 20 to 80° C. under atmospheric pressure to 5 atm in a suitable solvent, for example, ethanol, methanol, acetic acid, dilute hydrochloric acid or mixed solvent thereof in the presence of a suitable catalyst, for example, palladium on carbon, platinum oxide, rhodium-alumina or the like.

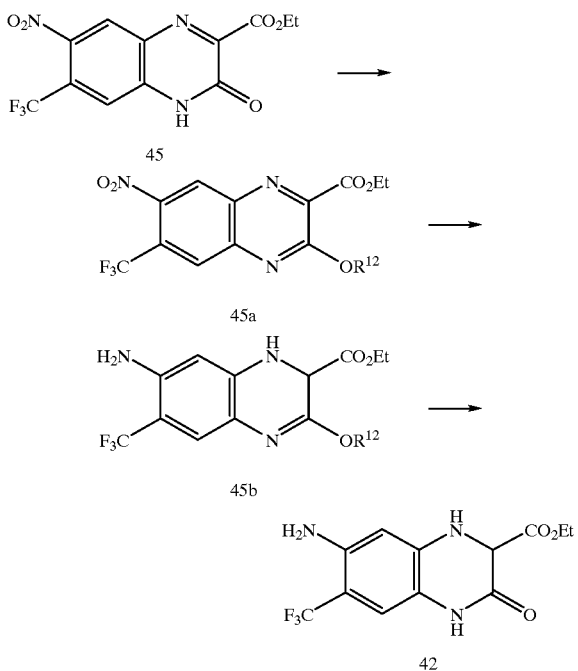

(wherein $R^{12}$ is as described above).

Also, compound (42) can be synthesized via compound (45a) and compound (45b), after nitration.

Namely, it can be synthesized also by reacting compound (45) with alkyl halide, for example, methyl iodide or the like, or aralkyl halide, for example, 4-methoxybenzyl chloride for 2 to 24 hours at 20 to 120° C. in a suitable solvent, for example, benzene, toluene, chloroform, methylene chloride, tetrahydrofuran or the like, using a suitable silver catalyst, for example, silver oxide, silver carbonate or the like to convert to compound (45a), then reducing this through catalytic hydrogenation, that is, hydrogenating at 20 to 80° C. under atmospheric pressure to 5 atm in a suitable solvent, for example, ethanol, methanol, acetic acid, dilute hydrochloric acid or mixed solvent thereof in the presence of a suitable catalyst, for example, palladium on carbon, platinum oxide, rhodium-alumina or the like to convert to compound (45b), and further reacting this (45b) for 0.5 to 72 hours at 20 to 120° C. without solvent or in a suitable solvent, for example, water, acetic acid, methanol or the like, using a suitable acid, for example, hydrochloric acid, sulfuric acid, hydrobromic acid, trifluoroacetic acid or the like.

Also, compounds represented by the general formula (45a) can be synthesized by reacting compounds represented by the general formula (45) for 2 to 6 hours at 0 to 120° C. in a suitable solvent, for example, benzene, toluene, chloroform, methylene chloride, tetrahydrofuran or the like, using a borate, for example, tetramethyloxonium borate or the like.

Moreover, compounds represented by the general formula (21) can be synthesized by reacting, for example, compounds represented by a general formula (46)

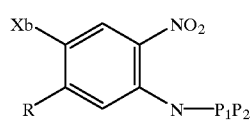

(wherein Xb and R are as described above, and $P_1$ and $P_2$ denote hydrogen atoms or protective groups of amino group), with compounds represented by the general formula (19)

(wherein T, V, ring B and m are as described above), to convert to compounds represented by a general formula (47), deprotecting these (general formula 48), and then reducing nitro group, leading to phenylenediamine (general formula 21).

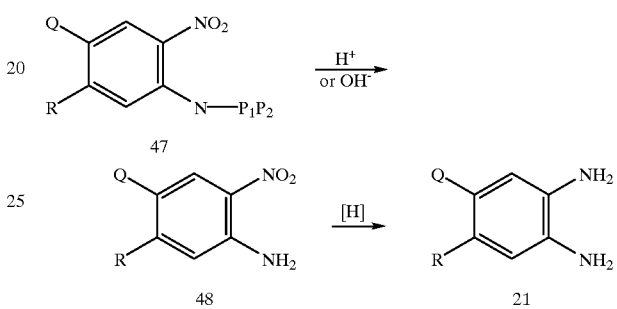

(wherein Q, R, $P_1$ and $P_2$ are as described above).

The reaction of general formula (46) and general formula (19) can be achieved by reacting for 5 to 48 hours at 20 to 160° C. in a suitable solvent, for example, tetrahydrofuran, dioxane, N,N-dimethylformamide, N,N-dimethylacetamide, N-methylpyrrolidone, acetonitrile, benzene, toluene or the like, without base or using a suitable inorganic or organic base, for example, sodium hydride, sodium carbonate, potassium carbonate, triethylamine or the like.

The deprotection of the general formula (47) can be conducted by reacting for 3 to 72 hours at 20 to 120° C. without solvent or in a suitable solvent, for example, water, methanol, ethanol, anisole or the like, using a suitable acid, for example, hydrochloric acid, sulfuric acid, hydrobromic acid, trifluoroacetic acid or the like, or for 0.5 to 10 hours at 20 to 100° C., using a suitable alkali, for example, potassium hydroxide, sodium hydroxide, or the like.

The reduction of nitro group of the general formula (48) can be conducted by reacting at 20 to 60° C. in water-alcohol, for example, water-ethanol, water-methanol or the like in the presence of sodium sulfide and ammonium chloride in the case of R being nitro group. Further, in the case of R being other than nitro group, it can also be conducted by reducing through catalytic hydrogenation, that is, hydrogenating at 25 to 80° C. under atmospheric pressure to 5 atm in a suitable solvent, for example, ethanol, methanol, acetic acid or the like in the presence of a suitable catalyst, for example, palladium carbon, platinum oxide, rhodium-alumina or the like. Furthermore, it can also be conducted by reacting at 25 to 100° C. in a suitable solvent, for example, ethanol, dilute hydrochloric acid, acetic acid or mixed solvent thereof in the presence of tin chloride, zinc, iron, sodium hydrosulfite or the like.

Moreover, compounds, R being trifluoromethyl group, among the compounds represented by the general formula (46) can be synthesized by nitrating general formula (50) synthesizable through known process, that is,

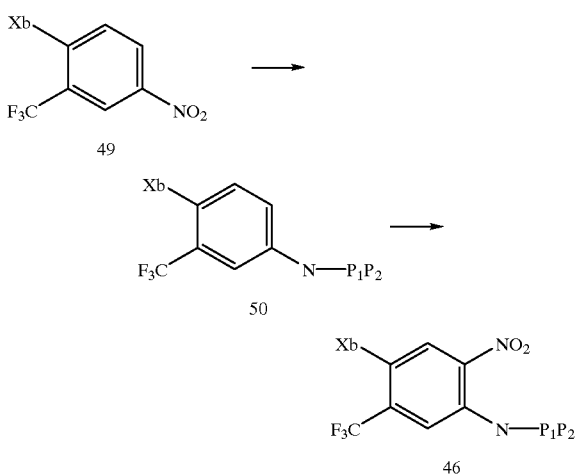

(wherein Xb, $P_1$ and $P_2$ are as described above), by reacting for 0.5 to 2 hours at −10 to 80° C. without solvent or in a suitable solvent, for example, concentrated sulfuric acid, carbon disulfide or acetic acid, using a suitable nitrating agent, for example, concentrated nitric acid, fuming nitric acid, potassium nitrate or the like.

Moreover, compounds represented by the general formula (48) can also be converted to general formula (1) according to WO92-11245. Namely, nitroaniline represented by the general formula (48) can be reacted with malonyl chloride to convert to general formula (51), and then intramolecularly cyclizing to convert to general formula (52), which is deoxidated to convert to general formula (1).

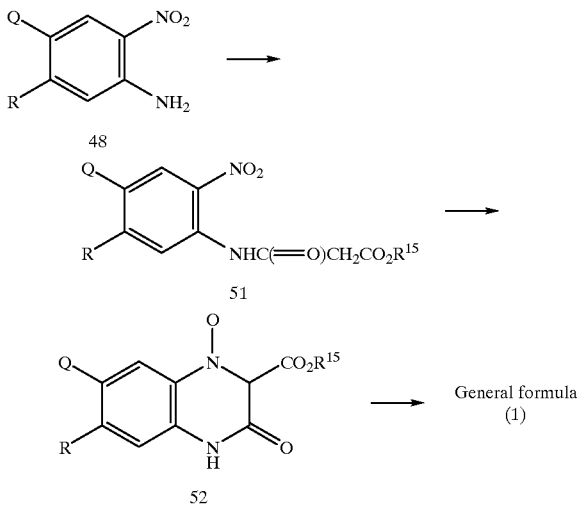

(wherein Q, R and $R^{15}$ are as described above). Best embodiment to put the invention into practice Examples of the invention will be described to illustrate the invention in more detail.

EXAMPLE 1

Methyl 7-chloro-3,4-dihydro-6-nitro-3-oxoquinoxaline- 2-carboxylate

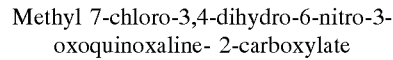
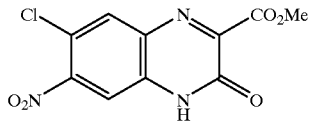

To a solution of methyl 7-chloro-3,4-dihydro-3-oxoquinoxaline-2-carboxylate (106 mg, 444 μmol) in acetic acid (1 ml) was added a solution of fuming nitric acid (39.5 μl, 888 μmol) in acetic acid (0.2 ml), and the mixture was stirred for 1 hour at 60° C. Water (10 ml) was added to the reaction mixture. The precidpitate was collected by filtration, washed with water, and then air-dried to obtain 66.6 mg of the title compound as yellow powder. Yield 53%.

$^1$H-NMR(DMSO-$d_6$,δ):3.93(3H,s),7.91(1H,s),8.29(1H,s), 13.26(1H,brs).

EXAMPLE 2

Ethyl 3,4-dihydro-7-fluoro-6-nitro-3-oxoquinoxaline-2-carboxylate

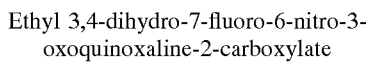
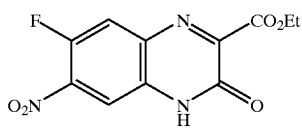

Using ethyl 3,4-dihydro-7-fluoro-3-oxoquinoxaline-2-carboxylate (558 mg, 2.36 mmol) and following the same process as in Example 1, 297 mg of the title compound were obtained as yellow powder. Yield 45%.

$^1$H-NMR(CDCl$_3$,δ):1.49(3H,t,J=7.0 Hz),4.58(2H,q,J=7.0 Hz), 7.89(1H,d,J=10.6 Hz),8.16(1H,d,J=6.2 Hz).

EXAMPLE 3

Ethyl 7-bromo-3,4-dihydro-6-nitro-3-oxoquinoxaline-2-carboxylate

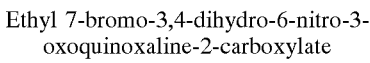
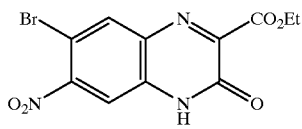

To a solution of ethyl 7-bromo-3,4-dihydro-3-oxoquinoxaline-2-carboxylate (2.60 g, 8.75 mmol) in acetic acid (35 ml) was added dropwise fuming nitric acid (1.40 ml, 31.5 mmol) at 60° C., and the mixture was stirred for 2 hours at the same temperature. The reaction mixture was poured into water (300 ml). The precipitate was collected by filtration, washed with water, and then air-dried to obtain 2.79 g of the title compound as yellow powder. Yield 93%.

$^1$H-NMR(DMSO-$d_6$,δ):1.33(3H,t,J=7.3 Hz),4.40(2H,q,J=7.3 Hz), 7.86(1H,s),8.40(1H,s),13.24(1H,brs).

EXAMPLE 4

Ethyl 3,4-dihydro-7-methyl-6-nitro-3-oxoquinoxaline-2-carboxylate

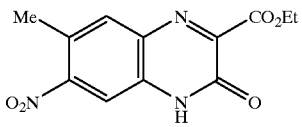

To a solution of ethyl-3,4-dihydro-7-methyl-3-oxoquinoxaline-2-carboxylate (1.65 g, 7.10 mmol) in acetic acid (15 ml) was added dropwise fuming nitric acid (1.36 ml, 14.2 mmol), and the mixture was stirred for 1 hour at 60° C. The reaction mixture was poured into ice water and, after stirring for 25 minutes, the precipitate was collected by filtration. These were air-dried and then dissolved into ethyl acetate. Moreover, the filtrate was extracted with ethyl acetate, which was combined with foregoing organic layer. After dried over anhydrous sodium sulfate, solvent was distilled off. The residue obtained was purified by means of silica gel column chromatography [n-hexane:ethyl acetate=1:1] to obtain 887 mg of the title compound as pale yellow powder. Yield 45%.

$^1$H-NMR(CDCl$_3$,δ):1.48(3H,t,J=7.3 Hz),2.65(3H,s),4.55 (2H,q,J=7.3 Hz), 7.91(1H,s),8.02(1H,s),12.42(1H,brs).

EXAMPLE 5

7-Chloro-3,4-dihydro-6-nitro-3-oxoquinoxaline-2-carboxylic Acid

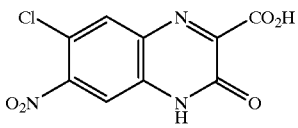

To a solution of the compound in Example 1 (64.6 mg, 228 μmol) in methanol (2 ml) was added dropwise 1N aqueous solution of potassium hydroxide (683 μl, 683 μmol), and the mixture was refluxed for 30 minutes. After cooling, water (5 ml) was added and the pH value was brought to 4 using acetic acid, then solvent was distilled off. Water was added to the residue obtained and the crystals were collected by filtration. After washing with water, these were air-dried to obtain 35.0 mg of the title compound as yellow powder. Yield 57%.

mp 227–229° C. (decomposition).

HR-MS:268.9824(−1.5 mmu).

EXAMPLE 6

3,4-Dihydro-7-fluoro-6-nitro-3-oxoquinoxaline-2-carboxylic Acid

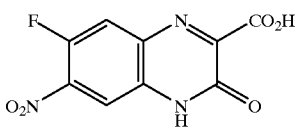

To a solution of the compound in Example 2 (100 mg, 356 μmol) in ethanol (3.5 ml) was added dropwise 1N aqueous solution of potassium hydroxide (711 μl, 711 μmol), and the mixture was refluxed for 2 hours. After cooling, water (10 ml) was added and the pH value was brought to 4 using acetic acid, then solvent was distilled off. After purified the residue obtained with synthetic adsorbing agent HP-20P [water water:acetonitrile=20:1], this was freeze-dried to obtain 69.0 mg of the title compound as yellow powder. Yield 77%.

mp 213–215° C. (decomposition).

HR-MS:253.0162 (+2.7 mmu).

EXAMPLE 7

7-Bromo-3,4-dihydro-6-nitro-3-oxoquinoxaline-2-carboxylic Acid

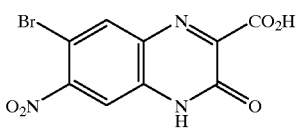

Using the compound in Example 3 (181 mg, 529 μmol) and following the same process as in Example 6, 107 mg of the title compound were obtained as yellow powder. Yield 64%.

mp 218–220° C. (decomposition).

HR-MS:312.9358 (+2.4 mmu).

EXAMPLE 8

3,4-Dihydro-7-methyl-6-nitro-3-oxoquinoxaline-2-carboxylic Acid

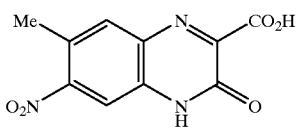

To a suspension of the compound in Example 4 (231 mg, 833 μmol) in methanol (15 ml) was added an aqueous (5 ml) solution of potassium hydroxide (93.5 mg, 1.67 mmol) at room temperature, and the mixture was stirred for 4 hours at room temperature and further for 30 minutes at 80° C. After cooling, the reaction mixture was distilled off under reduced pressure. The residue obtained was dissolved into water and the pH value was brought to under 1 using concentrated hydrochloric acid under ice-cooling, which was stirred for 30 minutes. The precipitate was collected by filtration, washed with water and with cold ethanol in sequence, and air-dried to obtain 126 mg of the title compound as pale yellow powder. Yield 60%.

mp 239–242° C.

Anal.Calcd. for $C_{10}H_7N_3O_5 \cdot 1/10H_2O$: C,47.86;H,2,89;N, 16.74. Found:C,47.90;H,2.92;N,16.61.

EXAMPLE 9

Ethyl 7-fluoro-3-methoxy-6-nitroquinoxaline-2-carboxylate

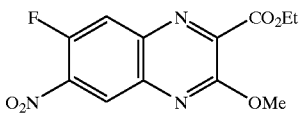

A suspension of the compound in Example 2 (1.00 g, 3.56 mmol), methyl iodide (440 μl, 7.07 mmol) and silver oxide (990 mg, 4.31 mmol) in toluene (100 ml) was stirred for 2 hours at 100° C. After cooling, the reaction mixture was filtered using celite, and solvent was distilled off. The residue obtained was purified by means of silica gel column chromatography [dichloromethane:ethyl acetate=4:1] to obtain 580 mg of the title compound as yellow powder. Yield 55%.

$^1$H-NMR(CDCl$_3$,δ):1.47(3H,t,J=7.3 Hz),4.18(3H,s),4.55 (2H,q,J=7.3 Hz), 7.95(1H,d,J=10.8 Hz),8.57(1H,d,J=7.3 Hz).

EXAMPLE 10

Ethyl 3-methoxy-7-methyl-6-nitroquinoxaline-2-carboxylate

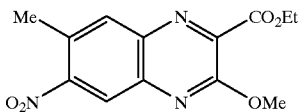

To a solution of the compound in Example 4 (1.42 g, 5.12 mmol) in anhydrous dichloromethane (80 ml) was added trimethyloxonium tetrafluoroborate (3.41 g, 23.1 mmol) at room temperature under stirring, and the mixture was stirred for 4.5 hours at room temperature and refluxed further for 1.5 hours. The reaction mixture was poured into saturated aqueous solution of sodium hydrogencarbonate and the organic layer was separated. The aqueous layer was further extracted with dichloromethane. The organic layers were combined and, after dried over anhydrous sodium sulfate, solvent was distilled off. The residue obtained was purified by means of silica gel column chromatography [n-hexane:ethyl acetate=10:1] to obtain 762 mg of the title compound as pale yellow powder. Yield 51%.

$^1$H-NMR(CDCl$_3$,δ):1.47(3H,t,J=7.3 Hz),2.72(3H,s),4.17 (3H,s),4.54 (2H,q,J=7.3 Hz),8.03(1H,s),8.43(1H,s).

EXAMPLE 11

Ethyl 7-(imidazole-1-yl)-3-methoxy-6-nitroquinoxaline-2-carboxylate

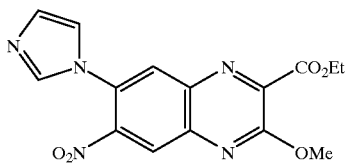

A solution of the compound in Example 9 (1.41 g, 4.78 mmol) and imidazole (1.63 g, 23.9 mmol) in acetonitrile (10 ml) was stirred for 9 hours at 50° C. After diluting with dichloromethane, the reaction mixture was washed with brine.

The aqueous layer was extracted with dichloromethane, which was combined with foregoing organic layer. After dried over anhydrous sodium sulfate, solvent was distilled off. The residue obtained was purified by means of silica gel column chromatography [n-hexane:ethyl acetate= 1:1→ethyl aetate] to obtain 423 mg of the title compound as an orange liquid. Yield 26%.

$^1$H-NMR(CDCl$_3$,δ):1.47(3H,t,J=7.3 Hz),4.23(3H,s),4.56 (2H,q,J=7.3 Hz),7.15(1H,t,J=1.5 Hz),7.27(1H,s),7.72(1H,s), 8.18(1H,s), 8.46(1H,s).

EXAMPLE 12

Ethyl 3-methoxy-6-nitro-7-(4-pyridone-1-yl)quinoxaline-2-carboxylate

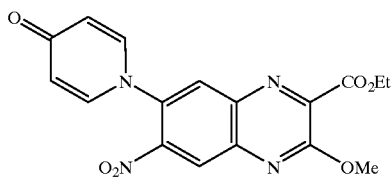

To a solution of the compound in Example 9 (180 mg, 610 μmol) in tetrahydrofuran (20 ml) was added 4-pyridone (290 mg, 3.05 mmol), followed by tube sealing, and the mixture was stirred for 4 hours at 100° C. and for 18 hours at 90° C. After cooling, the reaction mixture was concentrated under reduced pressure and the residue obtained was purified by means of silica gel column chromatography [chloroform:ethanol=40:1→20:1] to obtain 70.0 mg of the title compound as a pale yellow liquid. Yield 31%.

$^1$H-NMR(CDCl$_3$,δ):1.47(3H,t,J=7.2 Hz),4.24(3H,s),4.56 (2H,q,J=7.2 Hz),6.52(2H,d,J=7.8 Hz),7.38(2H,d,J=7.8 Hz), 8.22(1H,s), 8.60(1H,s).

EXAMPLES 13 THROUGH 21

Through the same process as in Example 12, compounds listed in following Table 1 were obtained.

TABLE 1

[Structure: quinoxaline core with R at 6-position, O₂N at 7-position, CO₂Et at 2-position, OMe at 3-position]

| Example | R | Example | R | Example | R |
|---|---|---|---|---|---|
| 13 | N-methylpiperidinyl | 16 | 4-(2-methoxyphenyl)piperazin-1-yl | 19 | 4-(4-chlorophenyl)piperazin-1-yl |
| 14 | —NMe₂ | 17 | 4-(3-methoxyphenyl)piperazin-1-yl | 20 | 4-phenylpiperazin-1-yl |
| 15 | 4-(4-fluorophenyl)piperazin-1-yl | 18 | 4-(4-nitrophenyl)piperazin-1-yl | 21 | 4-benzylpiperazin-1-yl |

EXAMPLE 13

¹H-NMR(CDCl₃,δ):1.46(3H,t,J=7.2 Hz),1.58–1.64(2H, m),1.71–1.77(4H,m),3.05(4H,brt,J=4.8 Hz),4.13(3H,s),4.53 (2H,q,J=7.2 Hz), 7.69(1H,s),8.13(1H,s).

EXAMPLE 14

¹H-NMR(DMSO-d₆,δ):1.35(3H,t,J=7.3 Hz),2.86(6H,s), 4.05(3H,s), 4.43(2H,q,J=7.3 Hz),7.66(1H,s),8.29(1H,s).

EXAMPLE 15

¹H-NMR(CDCl₃,δ):1.47(3H,t,J=7.3 Hz),3.27(8H,s),4.15 (3H,s), 4.55(2H,q,J=7.3 Hz),6.94(2H,dd,J=8.8,4.4 Hz), 7.00 (2H,t,J=8.8 Hz),7.80(1H,s),8.18(1H,s).

EXAMPLE 16

¹H-NMR(CDCl₃,δ):1.47(3H,t,J=7.3 Hz),3.23–4.27(4H, m), 3.28–3.33(4H,m),3.90(3H,s),4.15(3H,s),4.55(2H,q,J= 7.3 Hz), 6.90(1H,d,J=7.8 Hz),6.95–7.05(3H,m),7.80(1H,s), 8.17(1H,s).

EXAMPLE 17

¹H-NMR(CDCl₃,δ):1.47(3H,t,J=7.3 Hz),3.24–3.28(4H, m), 3.34–3.38(4H,m),3.81(3H,s),4.15(3H,s),4.55(2H,q,J= 7.3 Hz), 6.47(1H,dd,J=2.0,7.8 Hz),6.52(1H,t,J=2.0 Hz), 6.60(1H,dd,J=7.8,2.0 Hz),7.21(1H,t,J=7.8 Hz),7.79(1H,s), 8.18(1H,s).

EXAMPLE 18

¹H-NMR(CDCl₃,δ):1.47(3H,t,J=7.3 Hz),3.26–3.32(4H, m), 3.58–3.62(4H,m),4.16(3H,s),4.55(2H,q,J=7.3 Hz), 6.90 (2H,d,J=7.3 Hz),7.81(1H,s),8.17(2H,d,J=7.3 Hz),8.22(1H, s).

EXAMPLE 19

¹H-NMR(CDCl₃,δ):1.47(3H,t,J=7.3 Hz),3.24–3.28(4H, m),3.30–3.32(4H,m),4.15(3H,s),4.55(2H,q,J=7.3 Hz), 6.90 (2H,d,J=8.8 Hz),7.24(2H,d,J=8.8 Hz),7.80(1H,s),8.19 (1H,s).

EXAMPLE 20

¹H-NMR(CDCl₃,δ):1.47(3H,t,J=7.3 Hz),3.25–3.29(4H, m), 3.35–3.39(4H,m),4.15(3H,s),4.55(2H,q,J=7.3 Hz), 6.91 (1H,t,J=7.3 Hz),6.99(2H,d,J=8.8 Hz),7.30(2H,dd,J=8.8,7.3 Hz), 7.80(1H,s),8.18(1H,s).

EXAMPLE 21

¹H-NMR(CDCl₃,δ):1.46(3H,t,J=7.3 Hz),2.62–2.65(4H, m), 3.11–3.14(4H,m),3.53(2H,s),4.13(3H,s),4.53(2H,q,J= 7.3 Hz), 7.34–7.35(5H,m),7.71(1H,s),8.13(1H,s).

EXAMPLE 22

Ethyl 3-methoxy-7-(4-(4-methoxyphenyl) piperazine-1-yl)-6-nitroquinoxaline-2-carboxylate

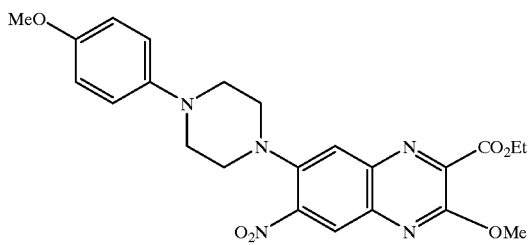

To a solution of the compound in Example 9 (300 mg, 1.02 mmol) in triethylamine (15 ml) was added 4-(methoxyphenyl)piperazine dihydrochloride (1.35 g, 5.10 mmol), followed by tube sealing, and the mixture was stirred for 8 hours at 100° C. After cooling, the reaction mixture was concentrated under reduced pressure and the residue obtained was purified by means of silica gel column chromatography [n-hexane:ethyl acetate=5:1→4:1] to obtain 145 mg of the title compound as red powder. Yield 30%.

¹H-NMR(CDCl₃,δ):1:47(3H,t,J=7.3 Hz),3.22–3.29(8H, m), 3.79(3H,s),4.15(3H,s),4.55(2H,q,J=7.3 Hz),6.87(2H,d, J=9.3 Hz), 6.96(2H,d,J=9.3 Hz),7.80(1H,s),8.18(1H,s).

EXAMPLES 23 THROUGH 28

Through the same process as in Example 22, compounds listed in following Table 2 were obtained.

TABLE 2

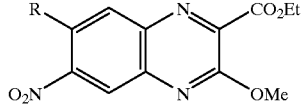

| Example | R | Example | R | Example | R |
|---|---|---|---|---|---|
| 23 | 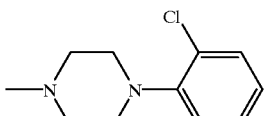 | 25 | 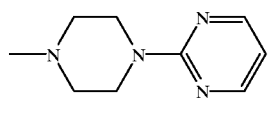 | 27 | 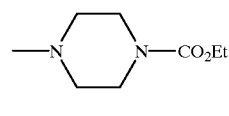 |
| 24 | 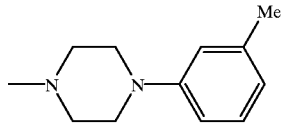 | 26 |  | 28 |  |

EXAMPLE 23

$^1$H-NMR(CDCl$_3$,δ):1.47(3H,t,J=7.3 Hz),3.22–3.26($_4$H,m), 3.28–3.33(4H,m),4.15(3H,s),4.55(2H,q,J=7.3 Hz), 7.02 (1H,dt,J=1.5,7.8 Hz),7.11(1H,dd,J=7.8,1.5 Hz), 7.26(1H,dt, J=1.5,7.8 Hz),7.39(1H,dd,J=7.8,1.5 Hz), 7.81(1H,s),8.18 (1H,s).

EXAMPLE 24

$^1$H-NMR(CDCl$_3$,δ):1.47(3H,t,J=7.3 Hz),2.34(3H,s), 3.24–3.29(4H,m),3.34–3.37(4H,m),4.15(3H,s),4.54(2H,q, J=7.3 Hz), 6.74(1H,d,J=7.8 Hz),6.79(1H,d,J=7.8 Hz),6.81 (1H,s), 7.19(1H,t,J=7.8 Hz),7.79(1H,s),8.18(1H,s).

EXAMPLE 25

$^1$H-NMR(CDCl$_3$,δ):1.46(3H,t,J=7.3 Hz),3.15–3.20(4H,m), 3.39–4.04(4H,m),4.15(3H,s),4.54(2H,q,J=7.3 Hz), 6.54 (1H,t,J=5.4 Hz),7.77(1H,s),8.19(1H,s),8.35(2H,d,J=5.4 Hz).

EXAMPLE 26

$^1$H-NMR(CDCl$_3$,δ):1.47(3H,t,J=7.3 Hz),2.15(3H,s), 3.063.13(4H,m), 3.62–3.67(2H,m),3.77–3.83(2H,m),4.15 (3H,s),4.54(2H,q,J=7.3 Hz), 7.76(1H,s),8.20(1H,s).

EXAMPLE 27

$^1$H-NMR(CDCl$_3$,δ):1.29(3H,t,J=6.8 Hz),1.47(3H,t,J=7.3 Hz), 3.043.09(4H,m),3.633.68(4H,m)4.15(3H,s),4.18(2H,q, J=6.8 Hz), 4.54(2H,q,J=7.3 Hz),7.75(1H,s),8.18(1H,s).

EXAMPLE 28

$^1$H-NMR(CDCl$_3$,δ):1.46(3H,t,J=7.3 Hz),1.72–1.82(2H, s), 2.00–2.09(2H,m),2.91–2.99(2H,m),3.28–3.38(2H,m), 3.88–3.97(1H,m),4.14(3H,s),4.54(2H,q,J=7.3 Hz),7.13(1H, s), 8.15(1H,s).

EXAMPLE 29

3-Methoxy-6-nitro-7-phenoxyquinoxaline-2-carboxylic Acid

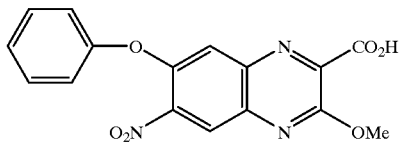

A suspension of the compound in Example 9 (590 mg, 2.00 mmol), phenol (941 mg, 10.0 mmol) and potassium carbonate (1.38 g, 10.0 mmol) in acetonitrile (20 ml) was stirred for 12 hours at 80° C. in sealed tube. After cooling, small quantity of water was added to dissolve inorganic salt and then solvent was distilled off. The residue obtained was dissolved into saturated aqueous solution of sodium hydrogencarbonate, which was then washed with ether. The aqueous layer was made to be pH 3 using concentrated hydrochloric acid, which was extracted with chloroform, dried over anhydrous sodium sulfate and then solvent was distilled off to obtain 407 mg of the title compound as yellow amorphous material. Yield 60%.

$^1$H-NMR(CDCl$_3$,δ):4.24(3H,s),7.18(2H,d,J=7.8 Hz), 7.31(1H,t,J=7.3 Hz),7.48(2H,t,J=7.8 Hz),7.51(1H,s),8.39 (1H,s).

EXAMPLE 30

3-Methoxy-6-nitro-7-(3-nitrophenoxy)quinoxaline-2-carboxylic Acid

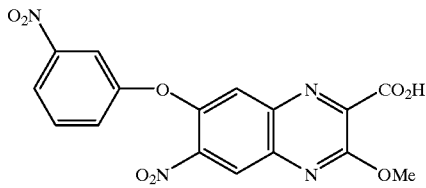

Through the same process as in Example 29, the title compound was obtained as a yellow solid.

$^1$H-NMR(CDCl$_3$,δ):4.26(3H,s),7.51(1H,dd,J=8.3,2.4 Hz), 7.64(1H,t,J=8.3 Hz),7.71(1H,s),7.95(1H,t,J=2.4 Hz), 8.14(1H,dd,J=8.3,2.0 Hz),8.50(1H,s).

EXAMPLE 31

Ethyl 3-methoxy-6-nitro-7-(3-nitrobenzylamino)quinoxaline-2-carboxylate

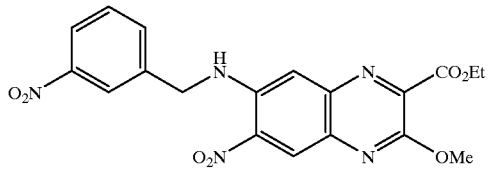

A solution of the compound in Example 9 (200 mg, 677 μmol) and 3-nitrobenzylamine hydrochloride (383 mg, 2.03 mmol) in N,N-dimethylformamide (2 ml) was stirred for 6 hours at 100° C. After cooling, water was added, and the solution was extracted with chloroform. After dried over anhydrous sodium sulfate, solvent was distilled off. The residue obtained was purified by means of silica gel column chromatography [n-hexane:ethyl acetate=4:1] to obtain 38.8 mg of the title compound as red powder. Yield 13%.

$^1$H-NMR(CDCl$_3$,δ):1.43(3H,t,J=7.3 Hz),4.11(3H,s), 4.50 (2H,q,J=7.3 Hz),4,73(2H,d,J=5.4 Hz),7.21(1H,s), 7.57(1H, t,J=7.8 Hz),7.73(1H,d,J=7.8 Hz),7.95(1H,t,J=5.4 Hz), 8.18 (1H,d,J=8.3 Hz),8.25(1H,s),8.79(1H,s).

EXAMPLE 32

Ethyl 3-methoxy-6-nitro-7-phthaloylquinoxaline-2-carboxylate

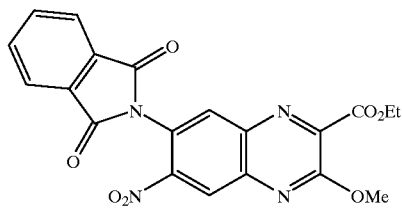

A solution of the compound in Example 9 (600 mg, 2.03 mmol) and potassium phthalimide (1.88 g, 10.2 mmol) in acetonitrile (20 ml) was stirred for 24 hours at 110° C. in sealed tube. After cooling, ethyl acetate was added, washed with brine, and, after dried over anhydrous sodium sulfate, solvent was distilled off. The residue obtained was purified by means of silica gel column chromatography [n-hexane:ethyl acetate=5:1→3:1] to obtain 70.0 mg of the title compound as pale yellow powder. Yield 8%.

$^1$H-NMR(DMSO-d$_6$,δ):1.37(3H,t,J=6.8 Hz),4.17(3H,s), 4.48(2H,q,J=6.8 Hz),8.01(2H,dd,J=5.4,2.9 Hz), 8.10(2H,dd, J=5.9,2.9 Hz),8.49(1H,s),8.71(1H,s).

EXAMPLE 33

Ethyl 7-(imidazole-1-yl)methyl-3-methoxy-6-nitroquinoxaline-2-carboxylate

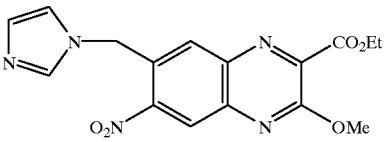

To a solution of the compound in Example 10 (121 mg, 415 μmol) in carbon tetrachloride (30 ml) was added N-bromosuccinimide (222 mg, 1.25 mmol) at room temperature, and the temperature was raised to 80° C. After added 2,2'-azobisisobutyronitrile (20.5 mg, 125 μmol), the reaction Frieze was stirred for 5.5 hours. The insolubles were filtered off and the solvent was distilled off, thus to obtain light brown powder. This was dissolved into acetonitrile (50 ml) and, after added imidazole (113 mg, 1.66 mmol), the mixture was stirred for 5.5 hours at room temperature. The reaction mixture was concentrated under reduced pressure and the residue obtained was purified by means of silica gel column chromatography [n-hexane:ethyl acetate=1:50] to obtain 102 mg of the title compound as light brown powder. Yield 69%.

$^1$H-NMR(CDCl$_3$,δ):1.45(3H,t,J=7.3 Hz),4.19(3H,s), 4.52 (2H,q,J=7.3 Hz),5.67(2H,s),6.98(1H,s),7.19(1H,s), 7.59 (1H,s),7.63(1H,s),8.65(1H,s).

EXAMPLE 34

Ethyl 7-dimethylaminomethyl-3-methoxy-6-nitroquinoxaline-2-carboxylate

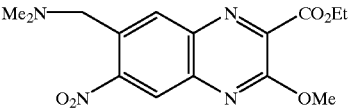

Through the same process as in Example 33, the title compound was obtained as brown oil.

$^1$H-NMR(CDCl$_3$,δ):1.47(3H,t,J=7.3 Hz),2.23(6H,s),3.82 (2H,s), 4.17(3H,s),4.54(2H,q,J=7.3 Hz),8.19(1H,s),8.28 (1H,s).

EXAMPLE 35

3,4-Dihydro-7-morpholino-6-nitro-3-oxoquinoxaline-2-carboxylic Acid

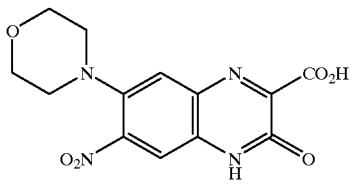

A solution of the compound in Example 9 (506 mg, 1.71 mmol) and morpholine (749 µl, 8.56 mmol) in acetonitrile (2 ml) was stirred for 6 hours at 80° C. After cooling, the reaction mixture was concentrated under reduced pressure. The residue obtained was purified by means of silica gel column chromatography [n-hexane:ethyl acetate=2:1] to obtain red liquid. This was dissolved into methanol (2 ml) and then 5% aqueous solution of potassium hydroxide (5 ml) was added, which was stirred for 24 hours at room temperature. The reaction mixture was made to be pH 3 using 3N hydrochloric acid, which was extracted with dichloromethane. After dried over anhydrous sodium sulfate, solvent was distilled off. 3N hydrochloric acid (5 ml) was added thereto and the mixture was stirred for 65 hours. The crystals deposited were collected by filtration, washed with water and then air-dried to obtain 275 mg of the title compound as red powder. Yield 48%.

mp 213.5–214.5° C.

Anal.Calcd. for $C_{13}H_{12}N_4O_6 \cdot 9/10H_2O$: C,46.41;H,4.13;N,16.65. Found:C,46.66;H,4.00;N,16.32.

EXAMPLE 36

3,4-Dihydro-7-(imidazole-1-yl)-6-nitro-3-oxoquinoxaline-2-carboxylic Acid

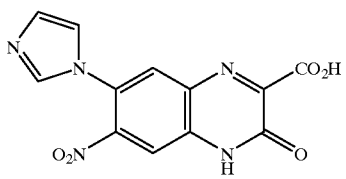

To the compound in Example 11 (423 mg, 1.23 mmol) was added 3N hydrochloric acid (20 ml), and the mixture was stirred for 6 hours at 80° C. Concentrated hydrochloric acid (2 ml) was added to the reaction mixture, which was further stirred for 10 hours. The precipitate was collected by filtration using water and methanol and air-dried to obtain 166 mg of the title compound as brown powder. Yield 44%.

mp >300° C.

Anal.Calcd. for $C_{12}H_7N_5O_5 \cdot 1/2H_2O$: C,46.46;H,2.60;N,22.58. Found:C,46.17;H,2.44;N,22.61.

EXAMPLE 37

3,4-Dihydro-6-nitro-3-oxo-7-(4-pyridone-1-yl)quinoxaline-2-carboxylic Acid

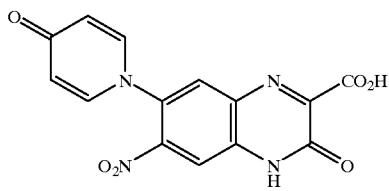

To a solution of the compound in Example 12 (1.34 g, 3.62 mmol) in ethanol (40 ml) were added water (10 ml) and 1N aqueous solution of potassium hydroxide (10.9 ml), and the mixture was refluxed for 4 hours. After cooling, cation-exchange resin Dowex XFS43279.00 was added to neutralize. After filtered off the resin, the filtrate was concentrated under reduced pressure. The residue obtained was dissolved into 3N hydrochloric acid (70 ml) and the solution was stirred for 4 hours at room temperature. After concentrating under reduced pressure, the residue obtained was washed with water and air-dried to obtain 1.00 g of the title compound as yellow powder. Yield 81%.

mp 283–285° C.

Anal.Calcd. for $C_{14}H_9N_4O_6 \cdot 4/5H_2O$: C,49.07;H,2.82;N,16.35. Found:C,48.84;H,2.62;N,16.05.

EXAMPLE 38

3,4-Dihydro-6-nitro-3-oxo-7-(piperidine-1-yl)quinoxaline-2-carboxylic Acid

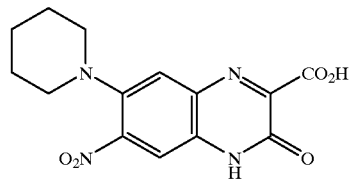

Using the compound in Example 13 (70.0 mg, 194 µmol) and following the same process as in Example 37, 31.0 mg of the title compound were obtained as purple powder. Yield 50%.

mp >300° C.

HR-MS:318.0977 (+1.3 mmu).

EXAMPLE 39

3,4-Dihydro-7-dimethylamino-6-nitro-3-oxoquinoxaline-2-carboxylic Acid

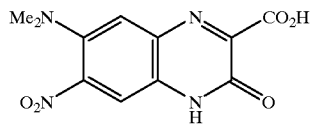

Using the compound in Example 14 (40.0 mg, 125 µmol) and following the same process as in Example 37, 5.00 mg of the title compound were obtained as dark brown powder. Yield 15%.

mp 194.5–196.5° C.

HR-MS:278.0641 (−1.0 mmu).

EXAMPLE 40

7-(4-(4-Fluorophenyl)piperazine-1-yl)-3-methoxy-6-nitro-quinoxaline-2-carboxylic Acid

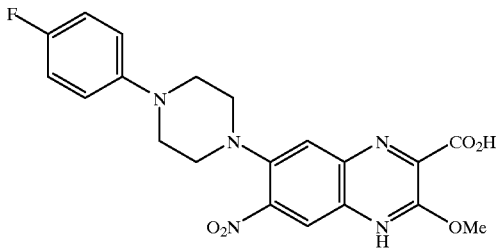

To a solution of the compound in Example 15 (357 mg, 784 μmol) in ethanol (4 ml) were added water (1 ml) and 1N aqueous solution of potassium hydroxide (1.57 ml, 1.57 mmol), and the mixture was refluxed for 4 hours. After cooling, 1N hydrochloric acid was added to adjust the pH value to 4 and brine was added. This was extracted with chloroform, dried over anhydrous magnesium sulfate and then solvent was distilled off to obtain 316 mg of the title compound as red powder. Yield 94%.

$^1$H-NMR(DMSO-$d_6$,δ):3.21(8H,s),4.04(3H,s), 7.02(2H, dd,J=9.3,4.9 Hz),7.08(2H,t,J=9.3 Hz),7.84(1H,s), 8.31(1H, s).

EXAMPLES 41 THROUGH 53

Through the same process as in Example 40, compounds listed in following Table 3 were obtained.

TABLE 3

| Example | R | Example | R | Example | R |
|---|---|---|---|---|---|
| 41 | 2-MeO-C$_6$H$_4$-piperazinyl | 46 | 4-Cl-C$_6$H$_4$-piperazinyl | 51 | Ac-piperazinyl |
| 42 | 3-MeO-C$_6$H$_4$-piperazinyl | 47 | 3-Me-C$_6$H$_4$-piperazinyl | 52 | CO$_2$Et-piperazinyl |
| 43 | 4-MeO-C$_6$H$_4$-piperazinyl | 48 | Ph-piperazinyl | 53 | 4-OH-piperidinyl |
| 44 | 4-NO$_2$-C$_6$H$_4$-piperazinyl | 49 | Bn-piperazinyl | | |
| 45 | 2-Cl-C$_6$H$_4$-piperazinyl | 50 | 2-pyrimidinyl-piperazinyl | | |

EXAMPLE 41

$^1$H-NMR(DMSO-$d_6$,δ):3.08–3.13(4H,m),3.17–3.23(4H, m), 3.80(3H,s),4.02(3H,s),6.90–6.99(4H,m),7.80(1H,s), 8.27(1H,s).

EXAMPLE 42

$^1$H-NMR(DMSO-$d_6$,δ):3.15–3.20(4H,m),3.25–3.30(4H, m), 3.73(3H,s),3.98(3H,s),6.40(1H,dd,J=8.3,2.0 Hz), 6.52 (1H,t,J=2.0 Hz),6.59(1H,dd,J=8.3,2.0 Hz),7.14(1H,t,J=8.3 Hz), 7.72(1H,s),8.21(1H,s).

EXAMPLE 43

$^1$H-NMR(DMSO-d$_6$,δ):3.13–3.18(4H,m),3.19–3.24(4H,m), 3.70(3H,s),4.08(3H,s),6.85(2H,d,J=8.8 Hz),6.96(2H,d,J=8.8 Hz), 7.89(1H,s),8.36(1H,s).

EXAMPLE 44

$^1$H-NMR(DMSO-d$_6$,δ):3.18–3.23(4H,m),3.58–3.65(4H,m),3.98(3H,s), 7.10(2H,d,J=9.3 Hz),7.71(1H,s),8.09(2H,d,J=9.3 Hz),8.23(1H,s).

EXAMPLE 45

$^1$H-NMR(DMSO-d$_6$,δ):3.10–3.16(4H,m),3.20–3.25(4H,m),4.04(3H,s), 7.08(1H,dt,J=7.8,1.5 Hz),7.25(1H,dd,J=7.8,1.5 Hz), 7.33(1H,dt,J=7.8,1.5 Hz),7.44(1H,dd,J=7.8,1.5 Hz),7.85(1H,s), 8.30(1H,s).

EXAMPLE 46

$^1$H-NMR(DMSO-d$_6$,δ):3.183.23(4H,m),3.25–3.29(4H,m),4.07(3H,s), 7.02(2H,d,J=8.8 Hz),7.27(2H,d,J=8.8 Hz), 7.90(1H,s),8.36(1H,s).

EXAMPLE 47

$^1$H-NMR(DMSO-d$_6$,δ):2.27(3H,s),3.20–3.21(4H,m), 3.24–3.26(4H,m), 4.05(3H,s),6.04(1H,d,J=7.8 Hz),6.79(1H,d,J=7.8 Hz),6.83(1H,s), 7.12(1H,t,J=7.8 Hz),7.85(1H,s), 8.33(1H,s).

EXAMPLE 48

$^1$H-NMR(DMSO-d$_6$,δ):3.19–3.20(4H,m),3.27–3.29(4H,m),3.98(3H,s), 6.82(1H,t,J=7.3 Hz),7.00(2H,d,J=7.8 Hz), 7.24(2H,dd,J=7.8,7.3 Hz), 7.72(1H,s),8.21(1H,s).

EXAMPLE 49

$^1$H-NMR(DMSO-d$_6$,δ):2.73–2.83(4H,m),3.12–3.18(4H,m),3.84(2H,s), 4.05(3H,s),7.34–7.44(5H,m),7.81(1H,s),8.31(1H,s).

EXAMPLE 50

$^1$H-NMR(DMSO-d$_6$,δ):3.07–3.14(4H,m),3.85–3.92(4H,m),3.98(3H,s), 6.67(1H,t,J=4.9 Hz),7.73(1H,s),8.23(1H,s),8.40(2H,d,J=4.9 Hz).

EXAMPLE 51

$^1$H-NMR(DMSO-d$_6$,δ):2.04(3H,s),3.00–3.04(2H,m), 3.05–3.09(2H,m), 3.54–3.59(4H,m),4.08(3H,s),7.87(1H,s), 8.37(1H,s).

EXAMPLE 52

$^1$H-NMR(DMSO-d$_6$,δ):1.21(3H,t,J=6.8 Hz),3.01–3.0$_7$(4H,m), 3.46–3.54(4H,m),4.07(2H,q,J=6.8 Hz),4.08(3H,s), 7.90(1H,s), 8.36(1H,s).

EXAMPLE 53

$^1$H-NMR(DMSO-d$_6$,δ):1.47–1.58(2H,m),1.79–1.89(2H,m), 2.85–2.94(2H,s),3.15–3.24(2H,m),3.61–3.70(1H,m), 4.07(3H,s), 7.76(1H,s),8.30(1H,s).

EXAMPLE 54

3,4-Dihydro-7-(4-(4-fluorophenyl)piperazine-1-yl)-6-nitro-3-oxoquinoxaline-2-carboxylic Acid

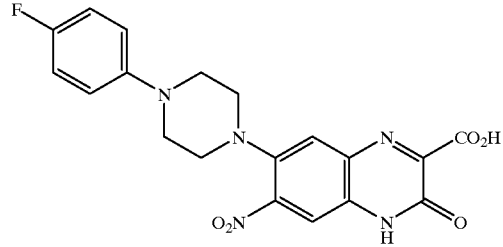

To a solution of the compound in Example 40 (25.0 mg, 58.5 μmol) in acetic acid (5 ml) was added 47% hydrobromic acid (1 ml), and the mixture was stirred for 2 hours at room temperature. The reaction mixture was concentrated under reduced pressure and the residue obtained was washed with water, then air-dried to obtain 14.0 mg of the title compound as pale yellow powder. Yield 56%.

mp 235.5–237.5° C.

Anal.Calcd. for $C_{19}H_{16}FN_5O_5 \cdot 7/10H_2O$: C,53.57;H, 4.12;N,16.44. Found:C,53.74;H,3.77;N,16.15.

HR-FAB+:414.1188 (−2.6 mmu).

EXAMPLE 55 THROUGH 58

Through the same process as in Example 54, compounds listed in following Table 4 were obtained.

TABLE 4

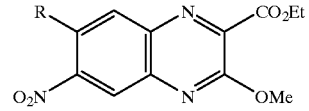

| Example | R | Example | R |
|---|---|---|---|
| 55 | —N(piperazinyl)N—C$_6$H$_4$—NO$_2$ | 57 | —N(piperazinyl)N—Ac |
| 56 | —N(piperazinyl)N—(2-pyrimidinyl) | 58 | —N(piperazinyl)N—CO$_2$Et |

EXAMPLE 55 mp 222–224° C.
HR-FAB+:441.1165 (+0.6 mmu).

EXAMPLE 56 mp 197–199° C.
HR-FAB+:398.1215 (+0.2 mmu).

EXAMPLE 57 mp 212–214° C.
HR-FAB+:362.1153 (+5.2 mmu).

EXAMPLE 58 mp 213.5–215.5° C.
HR-FAB+:391.1126 (−0.2 mmu).

EXAMPLE 59

3,4-Dihydro-7-(4-(2-methoxyphenyl)piperazine-1-yl)-6-nitro-3-oxoquinoxaline-2-carboxylic Acid

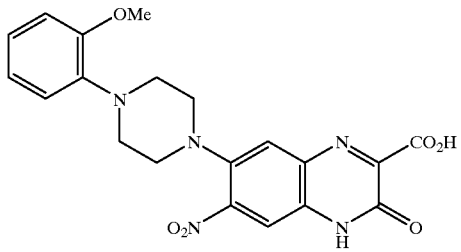

To the compound in Example 41 (314 mg, 715 μmol) was added 3N hydrochloric acid (10 ml), and the mixture was refluxed for 4 hours. The reaction mixture was cooled with ice and the insolubles were collected by filtration. These were washed with water and acetone in sequence and air-dried to obtain 247 mg of the title compound as brown powder. Yield 75%.

mp 204–206° C.

Anal.Calcd. for $C_{20}H_{19}N_5O_6 \cdot 2.1H_2O$: C,51.86;H,5.05;N, 15.12, Found:C,51.96;H,4.75;N,14.86.

HR-FAB+:426.1411 (−2.0 mmu).

EXAMPLE 60

7-(4-Benzylpiperazine-1-yl)-3,4-dihydro-6-nitro-3-oxoquinoxaline-2-carboxylic Acid

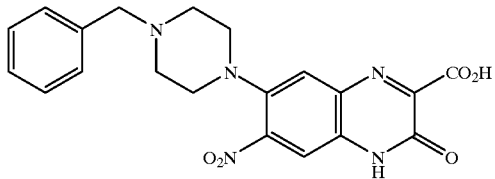

To a solution of the compound in Example 49 (30.0 mg, 70.8 μmol) in methanol (5 ml) was added 47% hydrobromic acid (1 ml), and the mixture was stirred for 16 hours at 70° C. After cooling, the reaction mixture was concentrated under reduced pressure and the residue obtained was recrystallized from water to obtain 18.0 mg of the title compound as pale yellow powder. Yield 60%.

mp 278–280° C.

Anal.Calcd. for $C_{20}H_{19}N_5O_5 \cdot 4/5H_2O$: C,56.68;H,4.90;N, 16.52. Found:C,56.79;H,4.65; N,16.23.

HR-FAB+:410.1451 (−1.4 mmu).

EXAMPLE 61

3,4-Dihydro-7-(4-hydroxypiperidine-1-yl)-6-nitro-3-oxoqinoxaline-2-carboxylic Acid

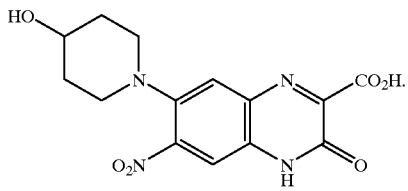

To the compound in Example 53 (30.0 mg, 86.1 μmol) was added 3N hydrochloric acid (5 ml), and the mixture was stirred for 2 hours at room temperature. The reaction mixture was concentrated and recrystallized from water to obtain 13.0 mg of the title compound as brown powder. Yield 44%.

mp 253–255° C.

Anal.Calcd. for $C_{14}H_{14}N_4O_6 \cdot 3/10H_2O$: C,49.50;H, 4.33;N,16.49. Found:C,49.76;H,4.19;N,16.32.

HR-FAB+:334.0894 (−1.9 mmu).

EXAMPLE 62

3,4-Dihydro-6-nitro-3-oxo-7-phenoxyquinoxaline-2-carboxylic Acid

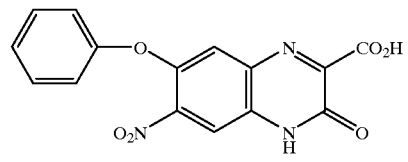

To a solution of the compound in Example 29 (400 mg, 1.17 mmol) in acetic acid (10 ml) was added concentrated hydrochloric acid (2 ml), and the mixture was allowed to stand overnight at room temperature. Water was added to the reaction mixture and the precipitate was collected by filtration. These were washed with water and chloroform in sequence and air-dried to obtain 79.5 mg of the title compound as brown powder. Yield 20%.

mp 154–156° C. (decomposition).

Anal.Calcd. for $C_{15}H_9N_3O_6 \cdot 3/4H_2O$: C,52.87;H,3.11;N, 12.33. Found:C,52.75;H,3.12;N,12.20.

HR-MS:327.0495 (+0.3 mmu).

EXAMPLE 63

3,4-Dihydro-6-nitro-7-(3-nitrophenoxy)-3-oxoquinoxaline-2-carboxylic Acid

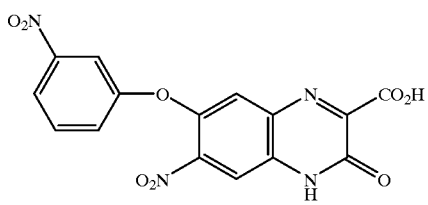

To a solution of the compound in Example 30 (277 mg, 717 μmol) in acetic acid (5 ml) was added concentrated hydrochloric acid (1 ml) at 60° C., and the mixture was stirred for 3 hours at the same temperature. Water was added to the reaction mixture and the precipitate was collected by filtration. These were washed with water and chloroform in sequence and air-dried to obtain 163 mg of the title compound as yellowish brown powder. Yield 58%.

mp 198–200° C. (decompositon).

Anal.Calcd. for $C_{15}H_8N_4O_8.H_2O$: C,46.16;H,2.58;N,14.36. Found:C,46.46;H,2.56;N,14.26.

HR-FAB+:373.0424(+0.4 mmu).

EXAMPLE 64

3,4-Dihydro-6-nitro-7-(3-nitrobenzylamino)-3-oxoquinoxaline-2-carboxylic Acid

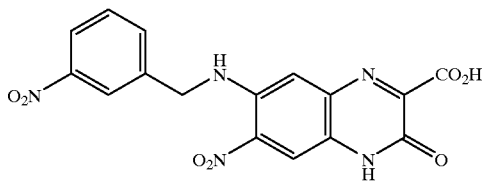

To a solution of the compound in Example 31 (38.8 mg, 90.8 μmol) in methanol (1 ml) was added 1N aqueous solution of potassium hydroxide (182 μl, 182 μmol), and the mixture was refluxed for 1 hour. After cooling, acetic acid was added to bring to pH 4 and solvent was distilled off. Water was added to the residue, which was extracted with chloroform. After dried over anhydrous sodium sulfate, solvent was distilled off. The residue obtained was dissolved into acetic acid (1 ml) and then concentrated hydrochloric acid (0.2 ml) was added, which was allowed to stand overnight at room temperature. Water was added to the reaction mixture and the precipitate was collected by filtration. These were washed with water and chloroform in sequence and then air-dried to obtain 27.2 mg of the title compound as dark purple powder. Yield 78%.

mp 239–241° C.

HR-FAB+:386.0716(−2.0 mmu).

EXAMPLE 65

3,4-Dihydro-6-nitro-3-oxo-7-phthaloylquinoxaline-2-carboxylic Acid

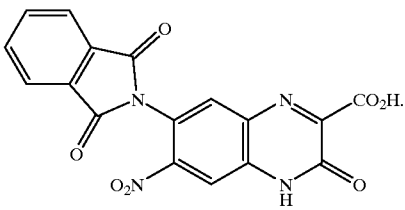

Using the compound in Example 32 (50.0 mg, 118 μmol) and following the same process as in Example 63, 5.70 mg of the title compound were obtained as yellow powder. Yield 13%.

mp 297–299° C.

HR-FAB−:379.0289(−2.5 mmu).

EXAMPLE 66

3,4-Dihydro-7-(imidazole-1-yl)methyl-6-nitro-3-oxoquinoxaline-2-carboxylic Acid Hydrochloride

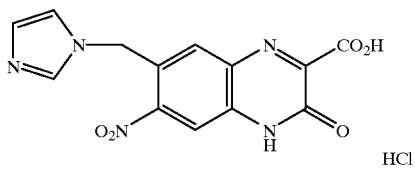

To the compound in Example 33 (102 mg, 285 μmol) was added 4N hydrochloric acid (15 ml), and the mixture was stirred for 2 hours at room temperature. Concentrated hydrochloric acid (1 ml) was added additionally to the reaction mixture to react further for 1.5 hours at 80° C. and solvent was distilled off under reduced pressure. The residue obtained was dissolved into water and, after treated with active carbon, solvent was distilled off. Small quantity of water and ethanol were added to the residue obtained and, after allowed to stand under ice-cooling while stirring, the precipitate was collected by filtration. These were washed with mixed solution of water-ethanol and ethyl acetate in sequence and then air-dried to obtain 39.7 mg of the title compound as pale yellow powder. Yield 39%.

mp >300° C.

Anal.Calcd. for $C_{13}H_9N_5O_5.HCl.1/2H_2O$: C,43.29;H,3.07;N,19.41. Found:C,43.38;H,3.06;N,19.48.

EXAMPLE 67

3,4-Dihydro-7-dimethylaminomethyl-6-nitro-3-oxoquinoxaline-2-carboxylic Acid

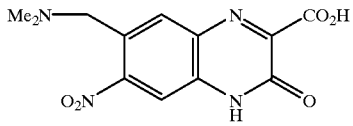

To a solution of the compound in Example 34 (161 mg, 482 μmol) in 4N hydrochloric acid (15 ml) was added concentrated hydrochloric acid (1 ml) at room temperature, and the mixture was stirred for 1 hour at room temperature and for 1 hour at 70° C. Solvent was distilled off, acetonitrile was added to the residue obtained and the precipitate was collected by filtration. These were purified with synthetic adsorbent SP-850 [water] to obtain 82.0 mg of the title compound as yellow powder. Yield 57%.

mp >300° C.

Anal.Calcd. for $C_{12}H_{12}N_4O_5 \cdot 3/10H_2O$: C,48.42;H, 4.27;N,18.82. Found:C,48.35;H,4.00;N,18.77.

EXAMPLE 68

7-Fluoro-3-methoxy-6-nitroquinoxaline-2-carboxamide

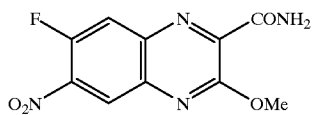

To a suspension of the compound in Example 9 (542 mg, 1.84 mmol) in methanol (20 ml) was added 28% aqueous ammonia (1.5 ml), and the mixture was refluxed for 3 hours. Water was added to the residue obtained by distilling off solvent under reduced pressure and the precipitate was collected by filtration. After air-drying, these were dissolved into ethyl acetate, which was dried over anhydrous sodium sulfate. Solvent was distilled off, the residue was decanted with isopropyl ether and air-dried to obtain 369 mg of the title compound as reddish brown powder. Yield 76%.

$^1$H-NMR(DMSO-d$_6$,δ):4.18(3H,s),7.97(1H,d,J=10.7 Hz), 8.56(1H,d,J=7.3 Hz).

EXAMPLE 69

3,4-Dihydro-7-fluoro-6-nitro-3-oxoquinoxaline-2-carboxamide

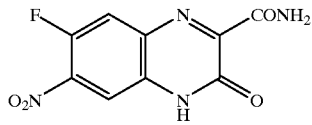

To a solution of the compound in Example 68 (108 mg, 406 mmol) in acetic acid (3 ml) was added 48% hydrobromic acid (0.6 ml) at 0° C., and the mixture was stirred for 1 hour at room temperature and for 1.5 hours at 60° C. The reaction mixture was poured into ice water, which was stirred for 20 minutes. The precipitate was collected by filtration and air-dried to obtain 69.7 mg of the title compound as yellowish brown powder. Yield 68%.

mp >300° C.

Anal.Calcd. for $C_9H_5FN_4O_4$: C,42.87;H,2.00;N,22.22. Found:C,42.89;H, 2.03;N,21.96.

EXAMPLE 70

3,4-Dihydro-6-nitro-3-oxo-7-(4-pyridone-1-yl)quinoxaline-2-carboxamide

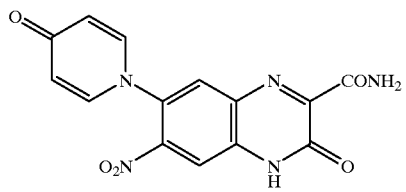

To a solution of the compound in Example 68 (190 mg, 714 mmol) in tetrahydrofuran (10 ml) was added 4-pyridone (339 mg, 3.57 mmol), and the mixture was stirred for 24 hours at 110° C. in sealed tube. After cooling, solvent was distilled off and ethanol was added. The precipitate was collected by filtration, washed with ethanol, water, ethanol and chloroform in sequence and then air-dried to obtain brown powder. 3N hydrochloric acid (5 ml) was added thereto and the mixture was stirred for 1 hour at room temperature. The reaction mixture was distilled off under reduced pressure, the residue obtained was washed with water and air-dried to obtain 21.0 mg of the title compound as yellowish brown powder. Yield 8%.

mp >300° C.

Anal.Calcd for $C_{14}H_9N_5O_5 \cdot 9/5H_2O$: C,46.75;H,3.53;N, 19.47. Found:C,47.15;H,3.13;N,19.14.

EXAMPLE 71

Ethyl 6-amino-7-fluoro-3-methoxyquinoxaline-2-carboxylate

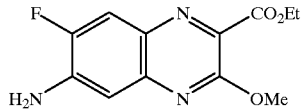

The compound in Example 9 (300 mg, 1.02 mmol) was dissolved into ethanol (50 ml), and, after added 10% palladium on carbon (60 mg), the mixture was stirred for 2 hours under hydrogen atmosphere (1 atm). The reaction mixture was filtered and the filtrate was concentrated under reduced pressure to obtain 260 mg of the title compound as yellow needles. Yield 96%.

$^1$H-NMR(CDCl$_3$,δ):1.45(3H,t,J=7.3 Hz),4.10(3H,s),4.45 (2H,brs). 4.50(2H,q,J=7.3 Hz),7.03(1H,d,J=8.8 Hz),7.65 (1H,d,J=11.2 Hz).

EXAMPLE 72

6-Amino-3,4-dihydro-7-fluoro-3-oxoquinoxaline-2-carboxylic Acid

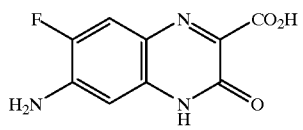

To a solution of the compound in Example 71 (50.0 mg, 189 μmol) in methanol (1 ml) was added 1N aqueous solution of sodium hydroxide (500 μl), and the mixture was stirred for 1 hour at room temperature. After concentrated under reduced pressure, the reaction mixture was dissolved into acetic acid (3 ml) and 47% hydrobromic acid (1 ml) was added, which was allowed to stand overnight. The reaction mixture was concentrated under reduced pressure, the residue obtained was dissolved into aqueous solution of sodium hydroxide, and then eluted through synthetic adsorbent SP-850 [water]. After concentrated under reduced pressure, the eluate was made acidic with 1N hydrochloric acid. The precipitate was collected by filtration, washed with water, and then air-dried to obtain 10.2 mg of the title compound as reddish brown powder. Yield 23%.

mp >300° C.

Anal.Calcd. for $C_9H_6FN_3O_3 \cdot 3/5H_2O$: C,46.20; H,3.10;N, 17.96. Found:C,46.32;H,3.02;N,17.77.

EXAMPLE 73

Ethyl 7-(3-formylpyrrole-1-yl)-3-oxo-1,2,3,4-tetrahydro-6-trifluoromethylquinoxaline-2-carboxylate

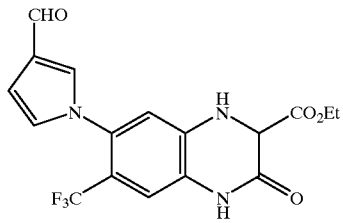

To a solution of ethyl 7-amino-3-oxo-1,2,3,4-tetrahydro-6-trifluoromethylquinoxaline-2-carboxylate (3.60 g, 11.9 mmol) in acetic acid (60 ml) was added dropwise 2,5-dimethoxytetrahydrofuran- 3-aldehyde (2.01 ml, 14.2 mmol) at 50° C., and the mixture was stirred for 1.5 hours at the same temperature. The reaction mixture was poured into water (300 ml), which was extracted with ethyl acetate. After dried over anhydrous sodium sulfate, solvent was distilled off. Methylene chloride was added to the residue obtained and the crystals were collected by filtration. These were washed with methylene chloride and then air-dried to obtain 2.57 g of the title compound as yellow powder. The filtrate and the washings were combined, concentrated under reduced pressure, and purified by means of silica gel column chromatography [ethyl acetate-hexane=2:1] to obtain further 973 mg. Total yield by weight 3.54 g. Yield 78%.

$^1$H-NMR(DMSO-d$_6$,δ):1.18(3H,t,J=7.3 Hz),4.12–4.17 (2H,m), 4.84(1H,d,J=2.0 Hz),6.60(1H,q,J=1.5 Hz),6.82(1H, s),7.04(1H,s), 7.16(1H,s),7.61(1H,d,J=1.5 Hz),7.79(1H,s), 9.74(1H,s), 11.02(1H,s).

EXAMPLE 74

Ethyl 7-(3-(aminomethyl)pyrrole-1-yl)-3-oxo-1,2,3,4-tetrahydro-6-trifluoromethylquinoxaline-2-carboxylate Hydrochloride

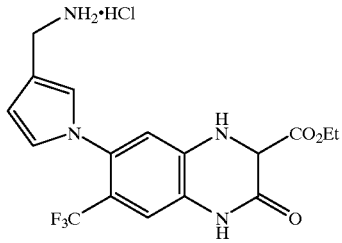

To a solution of the compound in Example 73 (1.98 g, 5.19 mmol) in ethanol (56 ml) were added hydroxylamine hydrochloride (778 mg, 11.2 mmol) and successively sodium acetate (919 mg, 11.2 mmol), and the mixture was refluxed for 2 hours. After cooling, water (300 ml) was added to the reaction mixture, which was extracted with ethyl acetate. After dried over anhydrous sodium sulfate, solvent was distilled off. The residue obtained was dissolved into ethanol (80 ml) and, after added palladium black (500 mg) and successively concentrated hydrochloric acid (4 ml), the mixture was stirred for 2 hours at room temperature in hydrogen stream (4 atm). Small quantity of water was added to the reaction mixture and, after dissolved hydrochloride, catalyst was filtered off and the solvent was distilled off. Acetone was added to the residue obtained and the crystals were collected by filtration. These were washed with acetone and then air-dried to obtain 2.01 g of the title compound as colorless powder. Yield 93%.

$^1$H-NMR(DMSO-d$_6$,δ):1.18(3H,t,J=7.3 Hz),3.90(2H,q,J= 5.4 Hz), 4.12–4.17(2H,m),4.83(1H,d,J=2.0 Hz),6.33(1H,t, J=2.4 Hz), 6.69(1H,s),6.88(1H,d,J=2.4 Hz),6.98(1H,s),7.14 (1H,s), 7.64(1H,s),8.06(3H,brs),11.00(1H,s).

EXAMPLE 75

Ethyl 7-(3-(((4-ethoxycarbonylphenyl)aminocarbonylamino)-methyl)pyrrole-1-yl)-3-oxo-1,2,3,4-tetrahydro-6-trifluoromethylquinoxaline-2-carboxylate

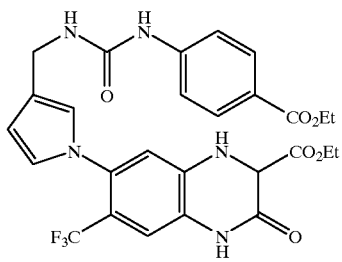

To a solution of the compound in Example 74 (1.03 g, 2.46 mmol) in N,N-dimethylformamide (25 ml) were added triethylamine (514 μl, 3.96 mmol) and successively ethyl 4-isocyanatobenzoate (564 mg, 2.95 mmol) at room temperature, and the mixture was stirred for 3 hours at the same temperature. The reaction mixture was poured into water (200 ml) and the precipitate was collected by filtration. These were washed with water and then with methylene chloride and air-dried to obtain 1.22 g of the title compound as yellowish white powder. Yield 87%.

¹H-NMR(DMSO-d₆,δ):1.17(3H,t,J=7.3 Hz),1.30(3H,t,J= 7.3 Hz), 4.11–4.17(4H,m),4.26(2H,q,J=7.3 Hz),4.81(1H,d, J=2.0 Hz), 6.17(1H,t,J=2.0 Hz),6.46(1H,t,J=5.4 Hz),6.71 (1H,s),6.80(2H,s), 7.11(1H,s),7.52(2H,d,J=8.8 Hz),7.83(2H, d,J=8.8 Hz),8.87(1H,s), 10.94(1H,s).

EXAMPLE 76

Ethyl 7-(3-(((4-ethoxycarbonyl-2-fluorophenyl) aminocarbonylamino)methyl)pyrrole-1-yl)-3-oxo-1, 2,3,4-tetrahydro-6-trifluoromethylquinoxaline-2-carboxylate

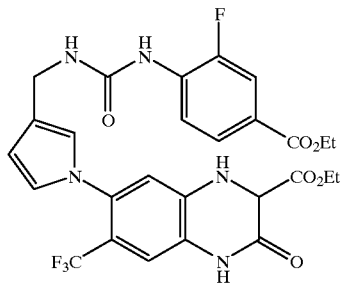

Using the compound in Example 74 (900 mg, 2.15 mmol) and ethyl 3-fluoro-4-isocyanatobenzoate (901 mg, 3.23 mmol) and through the same process as in Example 75, 448 mg of the title compound were obtained as yellow powder. Yield 35%.

¹H-NMR(DMSO-d₆,δ):1.17(3H,t,J=7.3 Hz),1.30(3H,t,J= 7.3 Hz), 4.11–4.19(4H,m),4.28(2H,q,J=7.3 Hz),4.81(1H,d, J=2.0 Hz), 6.17(1H,t,J=2.0 Hz),6.71(1H,s),6.808(1H,s), 6.814(1H,s), 7.00(1H,t,J=5.4 Hz),7.11(1H,s),7.52(1H,s), 7.66(1H,dd,J=11.7,2.0 Hz),7.72(1H,dd,J=8.8,2.0 Hz), 8.39 (1H,t,J=8.3 Hz),8,71(1H,d,J=2.9 Hz),10.94(1H,s).

EXAMPLE 77

Ethyl 3,4-dihydro-7-(3-(((4-ethoxycarbonylphenyl) aminocarbonylamino)methyl)pyrrole-1-yl)-3-oxo-6-trifluoromethylquinoxaline-2-carboxylate

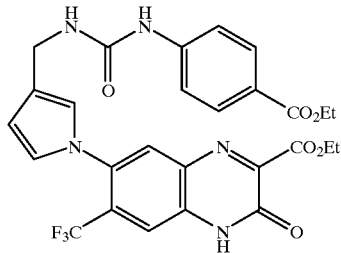

To a solution of the compound in Example 75 (100 mg, 174 μmol) in 1,4-dioxane (3 ml) was added 2,3-dichloro-5, 6-dicyanoquinone (39.5 mg, 174 μmol), and the mixture was refluxed for 1 hour. After cooling, solvent was distilled off, methylene chloride was added to the residuelobtained, and the crystals were collected by filtration. These were washed with methylene chloride and air-dried to obtain 94.2 mg of the title compound as yellow powder. Yield 95%.

¹H-NMR(DMSO-d₆,δ):1.30(3H,t,J=7.3 Hz),1.32(3H,t,J= 7.3 Hz), 4.19(2H,d,J=4.9 Hz),4.26(2H,q,J=7.3 Hz),4.40(2H, q,J=7.3 Hz), 6.25(1H,t,J=2.0 Hz),6.49(1H,t,J=5.4 Hz),6.92 (2H,s), 7.52(2H,d,J=8.8 Hz),7.75(1H,s),7.83(2H,d,J=8.8 Hz),7.91(1H,s), 8.90(1H,s),13.21(1H,s).

EXAMPLE 78

Ethyl 3,4-dihydro-7-(3-(((4-ethoxycarbonyl-2-fluorophenyl)aminocarbonylamino)methyl)pyrrole-1-yl)-3-oxo-6-trifluoromethylquinoxaline-2-carboxylate

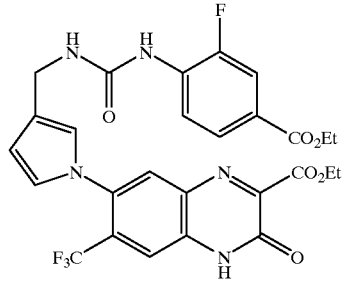

Using the compound in Example 76 (448 mg, 757 μmol) and following the same process as in Example 5, 252 mg of the title compound were obtained as yellow powder. Yield 57%.

¹H-NMR(DMSO-d₆₇,δ):1.31(3H,t,J=7.3 Hz),1.32(3H,t, J=7.3 Hz), 4.21(2H,d,J=4.9 Hz),4.28(2H,q,J=7.3 Hz),4.40 (2H,q,J=7.3 Hz), 6.25(1H,t,J=2.0 Hz),6.93(2H,d,J=2.4 Hz), 7.03(1H,t,J=5.4 Hz), 7.66(1H,dd,J=11.7,2.0 Hz),7.72(1H, dd,J=8.8,2.0 Hz),7.75(1H,s), 7.92(1H,s),8.39(1H,t,J=8.3 Hz),8.73(1H,d,J=2.5 Hz),13.21(1H,s).

EXAMPLE 79

7-(3-(((4-Carboxyphenyl)aminocarbonylamino)-methyl)pyrrole-1-yl)-3,4-dihydro-3-oxo-6-trifluoromethylquinoxaline-2-carboxylic Acid

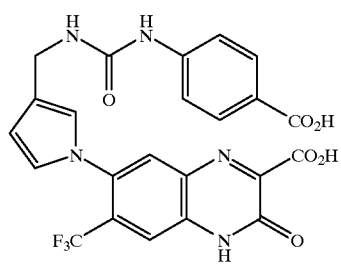

To a solution of the compound in Example 77 (85.2 mg, 174 μmol) in ethanol (2.4 ml) was added 1N aqueous solution of potassium hydroxide (596 μl, 596 μmol), and the mixture was refluxed for 1 hour. After cooling, solvent was distilled off, the residue was dissolved into small quantity of water and brought to pH 4 with 4N hydrochloric acid. Solvent was distilled off and small quantity of water was added again. The crystals were collected by filtration, washed with water, and then air-dried to obtain 69.2 mg of the title compound as yellowish brown powder. Yield 87%.

mp 234–236° C. (decomposition).

Anal.Calcd. for C₂₃H₁₆F₃N₅O₆.H₂O: C,51.79;H,3.40;N, 13.13. Found:C,51.91;H,3.43;N,12.82.

HR-FAB–:514.0968(–0.6 mmu).

EXAMPLE 80

7-(3-(((4-Carboxy-2-fluorophenyl)
aminocarbonylamino)-methyl)pyrrole-1-yl)-3,4-
dihydro-3-oxo-6-trifluoromethylquinoxaline-2-
carboxylic Acid

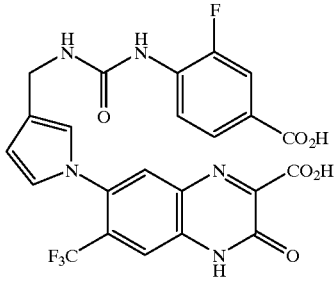

To a solution of the compound in Example 78 (250 mg, 424 μmol) in ethanol (7.5 ml) was added 1N aqueous solution of potassium hydroxide (1.70 ml, 1.70 mmol), and the mixture was refluxed for 1 hour. After cooling, solvent was distilled off, the residue was dissolved into water (5 ml) and brought to pH 2 with 4N hydrochloric acid. The precipitate was collected by filtration, washed with water, and then air-dried to obtain 213 mg of the title compound as yellow powder. Yield 93%.

mp 249–251° C. (decomposition).

Anal.Calcd. for $C_{23}H_{15}F_4N_5O_6 \cdot 1/2H_2O$: C,50.93;H, 2.97;N,12.91. Found:C,50.90;H,2.99;N,12.74.

HR-FAB–:532.0882(+0.2 mmu).

EXAMPLE 81

Ethyl 3,4-dihydro-7-(4-(hydroxymethyl)imidazole-
1-yl)-3-oxo-6-trifluoromethylquinoxaline-2-
carboxylate

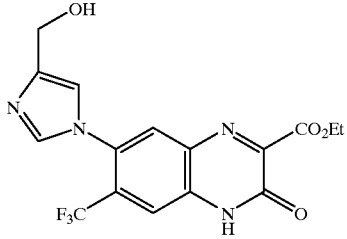

To a solution of 4-(4-(hydroxymethyl)imidazole-1-yl)-5-trifluoromethyl-1,2-phenylenediamine (200 mg, 781 μmol) in ethanol (10 ml) was added diethyl ketomalonate (142 μl, 937 μmol), and the mixture was refluxed for 4 hours. After cooling, solvent was distilled off and the residue obtained was purified by means of silica gel column chromatography [methylene chloride-methanol (50:1→10:1)] to obtain 129 mg of the the title compound as pale yellow powder. Yield 43%.

$^1$H-NMR(DMSO-d$_6$,δ):1.33(3H,t,J=6.8 Hz),4.40(2H,q,J= 6.8 Hz), 4.43(2H,d,J=5.4 Hz),5.01(1H,t,J=5.4 Hz),7.21(1H, s),7.75(1H,s), 7.78(1H,s),8.03(1H,s),13.26(1H,brs).

EXAMPLE 82

Ethyl 3,4-dihydro-7-(4-(((4-ethoxycarbonylphenyl)
carbamoyloxy)methyl)imidazole-1-yl)-3-oxo-6-
trifluoromethylquinoxaline-2-carboxylate

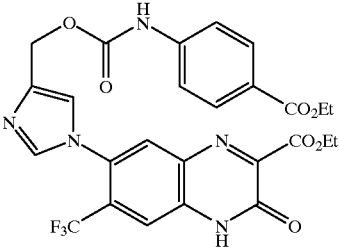

To a solution of the compound in Example 81 (129 mg, 337 μmol) in N,N-dimethylformamide (2 ml) was added ethyl 4-isocyanatobenzoate (118 mg, 675 μmol), and the mixture was stirred for 1 hour at room temperature, then allowed to stand statically overnight. Solvent was distilled off and the residue obtained was purified by means of silica gel column chromatography [methylene chloride-ethanol (50:1 20:1)] to obtain 130 mg of the the title compound as pale yellow powder. Yield 67%.

$^1$H-NMR(DMSO-d$_6$,δ):1.30(3H,t,J=7.3 Hz),1.32(3H,t,J= 6.8 Hz), 4.28(2H,q,J=7.3 Hz),4.38(2H,q,J=6.8 Hz),5.11(2H, s),7.53(1H,s), 7.61(2H,d,J=8.8 Hz),7.74(1H,s),7.86(1H,s), 7.89(2H,d,J=8.8 Hz), 8.02(1H,brs),10.20(1H,s),13.24(1H, brs).

EXAMPLE 83

7-(4-(((4-Carboxyphenyl)carbamoyloxy)methyl)
imidazole-1-yl)-3,4-dihydro-3-oxo-6-
trifluoromethylquinoxaline-2-carboxylic Acid

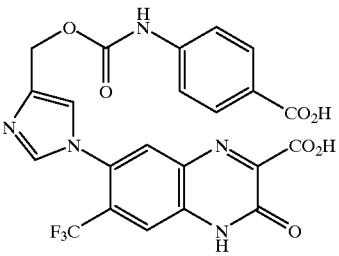

To a solution of the compound in Example 82 (130 mg, 227 μmol) in ethanol (5 ml) were added 1N aqueous solution of potassium hydroxide (681 μl, 681 μmol) and successively water (1 ml), and the mixture was refluxed for 2 hours. After cooling, solvent was distilled off, water was added, and the pH value was brought to 2 using 3N hydrochloric acid. The precipitate was collected by filtration, washed with water and then air-dried to obtain 32.0 mg of the the title compound as white powder. Yield 26%.

mp 278–280° C. (decomposition).

Anal.Calcd. for $C_{22}H_{14}F_3N_5O_7 \cdot 6/5H_2O$: C,49.02;H, 3.06;N,12.99. Found:C,49.37;H,3.10;N,12.66.

HR-FAB–:516.0760 (–0.7 mmu).

EXAMPLE 84

Ethyl 3-ethoxy-7-(4-(hydroxymethyl)imidazolyl)-6-nitroquinoxaline-2-carboxylate

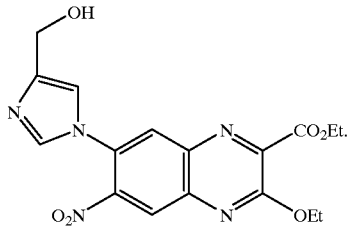

To a solution of ethyl 3-ethoxy-7-fluoro-6-nitroquinoxaline-2-carboxylate (6.90 g, 22.3 mmol) in acetonitrile (70 ml) were added dropwise 4-(hydroxymethyl)imidazole hydrochloride (15.1 g, 112 mmol) and successively triethylamine (23.4 ml, 168 mmol) under shading, and the mixture was refluxed for 16 hours. After cooling, methylene chloride was added to the reaction mixture, which was washed with water. The aqueous layer was extracted with methylene chloride, which was combined with foregoing organic layer. After dried over anhydrous sodium sulfate, solvent was distilled off. The residue obtained was purified by means of silica gel column chromatography [ethyl acetate] to obtain 3.69 g of the the title compound as brown power. Yield 43%. Moreover, 2.15 g of ethyl 3-ethoxy-7-fluoro-6-nitroquinoxaline-2-carboxylate were recovered. Yield 31%.

$^1$H-NMR(CDCl$_3$,δ):1.47(3H,t,J=7.1 Hz),1.53(3H,t,J=7.1 Hz), 4.55(2H,q,J=7.2 Hz),4.66(2H,q,J=7.2 Hz),4.71(2H,s), 7.09(1H,s), 7.68(1H,d,J=1.5 Hz),8.15(1H,s),8.43(1H,s).

EXAMPLE 85

Ethyl 7-(4-((N-(4-bromophenyl)carbamoyloxy)methyl)imidazolyl)-3-ethoxy-6-nitroquinoxaline-2-carboxylate

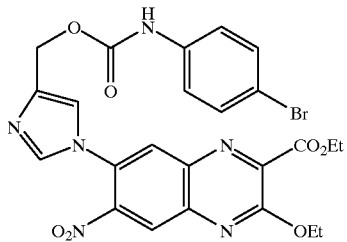

A solution of the compound in Example 84 (100 mg, 258 μmol) and 4-bromophenyl isocyanate (51.1 mg, 258 μmol) in methylene chloride (1 ml) was stirred for 3 hours at room temperature, and then solvent was distilled off to obtain 145 mg of the the title compound as yellow amorphous material. Yield 96%.

$^1$H-NMR(CDCl$_3$,δ):1.47(3H,t,J=7.3 Hz),1.53(3H,t,J=7.1 Hz), 4.55(2H,q,J=7.2 Hz),4.66(2H,q,J=7.0 Hz),5.23(2H,s), 6.81(1H,s), 7.24(1H,s),7.29(2H,d,J=8.8 Hz),7.41(2H,dt,J= 8.8,2.6 Hz),7.70(1H, d,J=1.5 Hz),8.15(1H,s),8.45(1H,s).

EXAMPLE 86

7-(4-((N-(4-Bromophenyl)carbamoyloxy)methyl)imidazolyl)-3,4-dihydro-6-nitro-3-oxoquinoxaline-2-carboxylic Acid

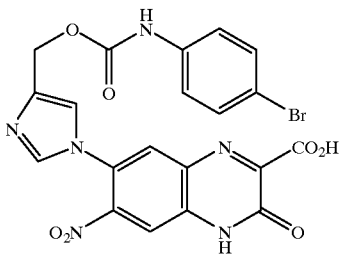

To a solution of the compound in Example 85 (100 mg, 171 μmol) in acetic acid (3 ml) was added concentrated hydrochloric acid (0.5 ml), and the mixture was stirred for 16 hours at room temperature. The reaction mixture was concentrated under reduced pressure, water was added, and the precipitate was collected by filtration. These were washed with water, then with chloroform, and then air-dried to obtain 57.2 mg of the the title compound as yellow powder. Yield 62%.

mp 270–272° C. (decomposition).
Anal.Calcd. for C$_{20}$H$_{13}$BrN$_6$O$_7$.1/2H$_2$O: C,44.62;H, 2.62;N,15.61. Found:C,44.97;H,2.51;N,15.26.
HR-FAB+:529.0123 (+1.5 mmu).

EXAMPLE 87

Sodium 7-(4-((N-benzylcarbamoyloxy)methyl)imidazolyl)-3,4-dihydro-6-nitro-3-oxoquinoxaline-2-carboxylate

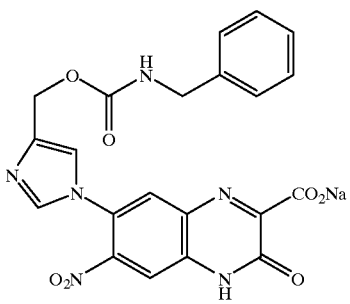

To a solution of the compound in Example 84 (100 mg, 258 μmol) in methylene chloride (3 ml) was added benzyl isocyanate (47.8 μl, 387 μmol), and the mixture was stirred for 6 hours at room temperature. After distilled off solvent, the residue was dissolved into acetic acid (3 ml), concentrated hydrochloric acid (0.6 ml) was added, and the mixture was stirred for 36 hours at room temperature. The reaction mixture was concentrated under reduced pressure and dissolved into 2N aqueous solution of sodium hydroxide, which was washed with ethyl acetate. The aqueous layer was concentrated under reduced pressure and the precipitate was collected by filtration. These were washed with water, then with chloroform and then air-dried to obtain 49.0 mg of the the title compound as yellow powder. Yield 36%.

mp 222–224° C. (decomposition).
HR-FAB+:487.0998 (+2.0 mmu).

EXAMPLE 88

3,4-Dihydro-6-nitro-3-oxo-7-( 4-((N-phenylcarbamoyloxy)methyl)imidazolyl)quinoxaline-2-carboxylic Acid

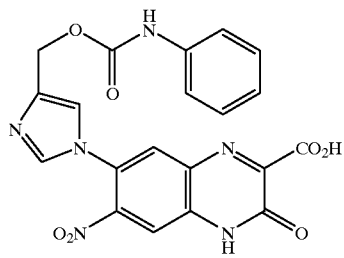

To a solution of the compound in Example 84 (100 mg, 258 μmol) in methylene chloride (3 ml) was added phenyl isocyanate (42.1 μl, 387 μmol), and the mixture was stirred for 6 hours at room temperature. After distilled off solvent, the residue was dissolved into acetic acid (3 ml), concentrated hydrochloric acid (0.6 ml) was added, and the mixture was stirred for 36 hours at room temperature. The reaction mixture was concentrated under reduced pressure and dissolved into 2N aqueous solution of sodium hydroxide, which was washed with ethyl acetate. This was neutralized with concentrated hydrochloric acid and the precipitate was collected by filtration. These were washed with water, then with chloroform and then air-dried to obtain 65.2 mg of the the title compound as blackish brown powder. Yield 52%.

mp 241–243° C. (decomposition).

HR-FAB+:451.1008 (+0.5 mmu).

EXAMPLES 89 THROUGH 107

Through the same process as in Example 88, compounds listed in following Table 5 were obtained.

TABLE 5

| Example | R | Example | R | Example | R | Example | R |
|---|---|---|---|---|---|---|---|
| 89 | 3-Br-C6H4 | 94 | 4-F-C6H4 | 99 | 2-Me-C6H4 | 104 | 3,5-Cl2-C6H3 |
| 90 | 2-Br-C6H4 | 95 | 3-F-C6H4 | 100 | 3-CF3-C6H4 | 105 | i-Pr |
| 91 | 4-Cl-C6H4 | 96 | 2-F-C6H4 | 101 | 2-CF3-C6H4 | 106 | n-Bu |
| 92 | 3-Cl-C6H4 | 97 | 4-Me-C6H4 | 102 | 2,4-Cl2-C6H3 | 107 | t-Bu |
| 93 | 2-Cl-C6H4 | 98 | 3-Me-C6H4 | 103 | 3,4-Cl2-C6H3 | | |

EXAMPLE 89 mp 266–268° C. (decomposition).
Anal.Calcd. for $C_{20}H_{13}BrN_6O_7 \cdot HCl \cdot H_2O$: C,41.15;H, 2.76;N,14.40. Found:C,41.07;H,2.67;N,14.35.
HR-FAB+:529.0140 (+3.3 mmu).

EXAMPLE 90 mp 260–262° C. (decomposition).
Anal.Calcd. for $C_{20}H_{13}BrN_6O_7 \cdot H_2O$: C,43.89;H,2.76;N, 15.36. Found:C,44.24;H,2.66;N,15.03.
HR-FAB+:529.0084 (−2.3 mmu).

EXAMPLE 91 mp 250–252° C. (decomposition).
HR-FAB−:483.0451 (−0.5 mmu).

EXAMPLE 92 mp 215–217° C. (decomposition).
Anal.Calcd. for $C_{20}H_{13}ClN_6O_7 \cdot HCl \cdot 1/2H_2O$: C,45.30;H, 2.85;N,15.85. Found:C,45.23;H,2.95;N,15.84.
HR-FAB−:483.0476 (+2.0 mmu).

EXAMPLE 93 mp 205–207° C. (decomposition).
HR-FAB−:483.0466 (+1.0 mmu).

EXAMPLE 94 mp 217–219° C. (decomposition).
Anal.Calcd. for $C_{20}H_{13}FN_6O_7 \cdot HCl \cdot 1/2H_2O$: C,46.75;H, 2.94;N,16.36. Found:C,47.16;H,3.05;N,16.28.
HR-FAB+:469.0915 (+0.7 mmu).

EXAMPLE 95 mp 270–272° C. (decomposition).
HR-FAB+:467.0748 (−0.4 mmu).

EXAMPLE 96 mp 251–253° C. (decomposition).
Anal.Calcd. for $C_{20}H_{13}FN_6O_7 \cdot 1/2H_2O$: C,50.32;H, 2.96;N,17.60. Found:C,50.01;H,2.68;N,17.65.
HR-FAB−:467.0787 (+3.6 mmu).

EXAMPLE 97 mp 265–267° C. (decomposition).
HR-FAB+:465.1156 (−0.3 mmu).

EXAMPLE 98 mp 223–225° C. (decomposition).
Anal.Calcd. for $C_{21}H_{16}N_6O_7 \cdot 1/2H_2O$: C,53.28;H,3.62;N, 17.75. Found:C,53.27;H,3.51;N,17.61.
HR-FAB−:463.0996 (−0.6 mmu).

EXAMPLE 99 mp 252–254° C. (decomposition).
Anal.Calcd. for $C_{21}H_{16}N_6O_7 \cdot HCl$: C,50.36;H,3.42;N, 16.78. Found:C,50.38;H,3.64;N,16.80.
HR-FAB−:463.1009 (+0.7 mmu).

EXAMPLE 100 mp 256–258° C. (decomposition).
HR-FAB−:517.0723 (+0.3 mmu).

EXAMPLE 101 mp 230–232° C. (decomposition).
Anal.Calcd. for $C_{21}H_{13}F_3N_6O_7 \cdot 1/4H_2O$: C,48.23;H, 2.60;N,16.07. Found:C,47.93;H,2.52;N,16.09.
HR-FAB−:517.0704 (−1.5 mmu).

EXAMPLE 102 mp 203–205° C. (decomposition).
Anal.Calcd. for $C_{20}H_{12}Cl_2N_6O_7 \cdot H_2O$: C,44.71;H,2.63;N, 15.64. Found:C,44.39;H,2.40;N,15.34.
HR-FAB−:517.0046 (−2.0 mmu).

EXAMPLE 103 mp 218–220° C. (decomposition).
Anal.Calcd. for $C_{20}H_{13}Cl_2N_6O_7 \cdot HCl \cdot 1/2H_2O$: C,42.54;H,2.50;N,14.88. Found:C,42.79;H,2.54;N,14.95.
HR-FAB−:517.0062 (−0.5 mmu).

EXAMPLE 104 mp 246–248° C. (decomposition).
Anal.Calcd for $C_{20}H_{12}C_2N_6O_7 \cdot 1/2H_2O$: C,45.47;H, 2.48;N,15.91. Found:C,45.43;H,2.28;N,15.95.
HR-FAB−:517.0065 (−0.2 mmu).

EXAMPLE 105 mp 199–201° C. (decomposition).
Anal.Calcd. for $C_{17}H_{16}N_6O_7 \cdot H_2O$: C,47.01;H,4.18;N, 19.35. Found:C,47.19;H,3.91;N,19.40.
HR-FAB−:415.1001 (−0.2 mmu).

EXAMPLE 106 mp 194–196° C. (decomposition).
Anal.Calcd. for $C_{18}H_{18}N_6O_7 \cdot 1/2H_2O$: C,49.20;H,4.36;N, 19.13. Found:C,49.06;H,4.23;N,18.92.
HR-FAB−:429.1161 (+0.2 mmu).

EXAMPLE 107 mp 185–187° C. (decomposition).
HR-FAB−:429.1140 (−1.9 mmu).

EXAMPLE 108

Sodium 3,4-dihydro-7-4-((-N-(4-methoxyphenyl)carbamoyloxy)methyl)imidazolyl)-6-nitro-3-oxoquinoxaline-2-carboxylate

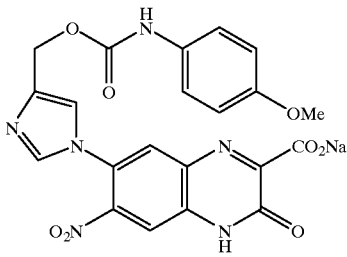

To a solution of the compound in Example 84 (100 mg, 258 μmol) in methylene chloride (1 ml) was added 4-methoxyphenyl isocyanate (50.1 μl, 387 μmol), and the mixture was stirred for 6 hours at room temperature. After distilled off solvent, the residue was dissolved into acetic acid (3 ml) and concentrated hydrochloric acid (0.6 ml) was added, which was stirred for 24 hours at room temperature. The reaction mixture was concentrated under reduced pressure and dissolved into 2N aqueous solution of sodium hydroxide, which was then washed with ethyl acetate. This was concentrated under reduced pressure and the precipitate was collected by filtration. These were washed with water, then with chloroform and then air-dried to obtain 70.2 mg of the the title compound as yellow powder. Yield 53%.

mp 265–267° C. (decomposition).

Anal.Calcd. for $C_{21}H_{15}N_6O_8Na·1/2H_2O$: C,49.32;H, 3.15;N,16.43. Found:C,49.51;H,3.08;N,16.58.

HR-FAB+:503.0913 (−1.4 mmu).

EXAMPLE 109

7-(4-((N-(2,6-Dichlorophenyl)carbamoyloxy) methyl)imidazolyl)-3,4-dihydro-6-nitro-3-oxoquinoxaline-2-carboxylic Acid

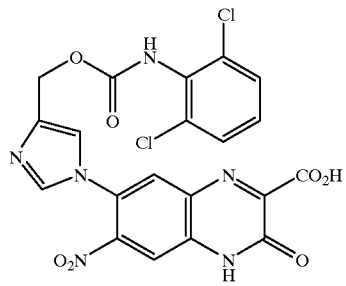

A solution of the compound in Example 84 (100 mg, 258 µmol) and 2,6-dichlorophenyl isocyanate (72.8 mg, 387 µmol) in benzene (5 ml) was refluxed for 2 hours. After cooling, the reaction mixture was purified by means of silica gel column chromatography[hexane-ethyl acetate=1:1] to obtain a yellow oil. This was dissolved into acetic acid (5 ml) and concentrated hydrochloric acid (1 ml) was added, which was stirred for 24 hours at room temperature. The reaction mixture was concentrated under reduced pressure, dissolved into 2N aqueous solution of sodium hydroxide, and then the insolubles were filtered off. After neutralized using concentrated hydrochloric acid, the precipitate was collected by filtration. These were washed with water, then with ethyl acetate and then air-dried to obtain 9.8 mg of the the title compound as yellowish brown powder. Yield 7%.

mp 253–255° C. (decomposition).

HR-FAB−:517.0087 (+2.1 mmu).

EXAMPLES 110 THROUGH 113

Through the same process as in Example 109, compounds listed in following Table 6 were obtained.

TABLE 6

| Example | R |
|---|---|
| 110 | 4-methylphenyl-OCF₃ |
| 111 | 4-methylphenyl-iPr |
| 112 | 2,3-dichloro-methylphenyl |
| 113 | 2,4-dichloro-methylphenyl |

EXAMPLE 110 mp 252–254° C. (decomposition).

HR-FAB−:533.0677 (+0.9 mmu).

EXAMPLE 111 mp 263–265° C. (decomposition).

HR-FAB−:491.1323 (+0.8 mmu).

EXAMPLE 112 mp 234–236° C. (decomposition).

Anal.Calcd. for $C_{20}H_{12}Cl_2N_6O_7$: C,46.26;H,2.33;N, 16.18. Found:C,46.12;H,2.38;N,15.90.

HR-FAB−:517.0043 (−0.5 mmu).

EXAMPLE 113 mp 272–274° C. (decomposition).

HR-FAB−:517.0090 (+2.4 mmu).

EXAMPLE 114

3,4-Dihydro-6-nitro(3-oxo-7-(4-((N-(4-trifluoromethylphenyl)carbamoyloxy)methyl)imidazolyl)quinoxaline-2-carboxylic Acid

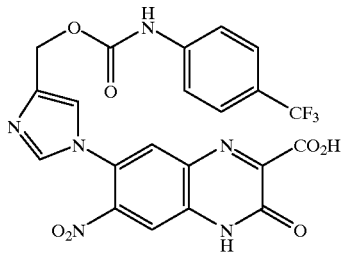

A solution of the compound in Example 84 (100 mg, 258 μmol), 4-trifluoromethylbenzoic acid (73.6 mg, 387 μmol), diphenylphosphoric azide (83.4 μl, 387 μmol) and triethylamine (53.9 μl, 387 μmol) in benzene (5 ml) was refluxed for 3 hours. After cooling, the reaction mixture was purified by means of silica gel column chromatography [hexane-ethyl acetate=1:1] to obtain a yellow oil. This was dissolved into acetic acid (5 ml), and concentrated hydrochloric acid (1 ml) was added, which was stirred for 24 hours at room temperature. The reaction mixture was concentrated under reduced pressure, 2N aqueous solution of sodium hydroxide was added, and the insolubles were filtered off. The filtrate was made acidic with concentrated hydrochloric acid and the precipitate was collected by filtration. These were washed with water and ethyl acetate in sequence and then air-dried to obtain 14.6 mg of the title compound as yellow powder. Yield 11%.

mp 276–278° C. (decomposition).

HR-FAB−:517.0703 (−1.6 mmu).

EXAMPLE 115

7-(4-((N-(4-Carboxyphenyl)carbamoyloxy)methyl)imidazolyl)-3,4-dihydro-6-nitro-3-oxoquinoxaline-2-carboxylic Acid

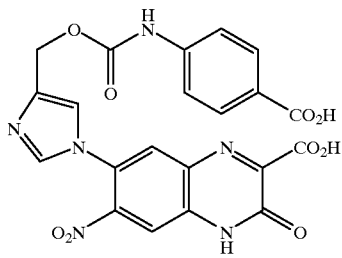

A solution of the compound in Example 84 (100 mg, 258 μmol) and ethyl 4-isocyanatobenzoate (74.0 mg, 387 μmol) in benzene (5 ml) was refluxed for 2 hours. After cooling, the reaction mixture was purified by means of silica gel column chromatography [hexane-ethyl acetate=1:1] to obtain yellow oil. This was dissolved into acetic acid (5 ml) and concentrated hydrochloric acid (1 ml) was added, which was stirred for 24 hours at room temperature. The reaction mixture was concentrated under reduced pressure, water was added, and the precipitate was collected by filtration. These were washed with water, then with ethyl acetate and then air-dried to obtain brown powder. This was dissolved into 1N aqueous solution of lithium hydroxide (15 ml) and the solution was stirred for 2.5 hours at room temperature. After filtered off the insolubles, the solution was made acidic with concentrated hydrochloric acid and the precipitate was collected by filtration. These were washed with water and then air-dried to obtain 47.8 mg of the title compound as brown powder. Yield 37%.

mp 268–270° C. (decomposition).

HR-FAB−:493.0769 (+2.5 mmu).

EXAMPLE 116

7-(4-((N-(3-Carboxyphenyl)carbamoyloxy)methyl)imidazolyl)-3,4-dihydro-6-nitro-3-oxoquinoxaline-2-carboxylic Acid

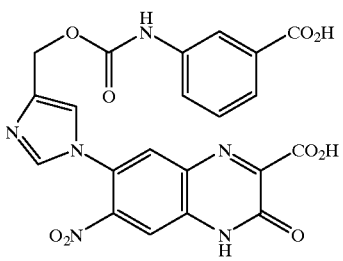

Using the compound in Example 84 (500 mg, 1.29 mmol) and ethyl 3-isocyanatobenzoate (321 μl, 1.94 mmol) and following the same process as in Example 32, 297 mg of the title compound were obtained as yellowish brown powder. Yield 44%.

mp 272–274° C. (decomposition).

Anal.Calcd. for $C_{21}H_{14}N_6O_9 \cdot 3/2H_2O$: C,48.47;H,3.29;N, 16.15. Found:C,48.62;H,3.13, N,16.27.

HR-FAB−:493.0739 (−0.5 mmu).

EXAMPLE 117

Ethyl 3-ethoxy-6-nitro-7-(4-(trifluoroacetamidomethyl)imidazolyl)quinoxaline-2-carboxylate

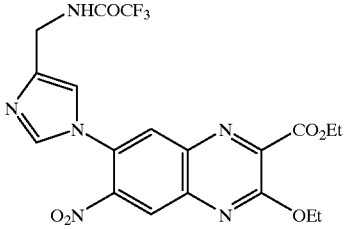

To a solution of ethyl 3-ethoxy-7-fluoro-6-nitroquinoxaline-2-carboxylate (308 mg, 999 μmol) and 4-(trifluoroacetamidomethyl)imidazole (1.72 g, 8.91 mmol) in acetonitrile (10 ml) was added triethylamine (3.00 ml, 21.5 mmol), and the mixture was stirred for 15 hours at 130° C. in sealed tube. The reaction mixture was concentrated under reduced pressure and the residue obtained was purified by means of silica gel column chromatography [methylene chloride] to obtain 179 mg of the title compound as light brown powder. Yield 37%.

$^1$H-NMR(CDCl$_3$,δ):1.47(3H,t,J=6.8 Hz),1.52(3H,t,J=7.3 Hz), 4.545(2H,s),4.553(2H,q,J=7.3 Hz),4.67(2H,q,J=6.8 Hz), 7.12(1H,d,J=1.5 Hz),7.16(1H,brs),7.67(1H,d,J=1.5 Hz), 8.16(1H,s),8.46(1H,s).

EXAMPLE 118

3,4-Dihydro-7-(4-(((2-fluorophenyl)aminocarbonylamino)methyl)imidazolyl)-6-nitro-3-oxoquinoxaline-2-carboxylic Acid

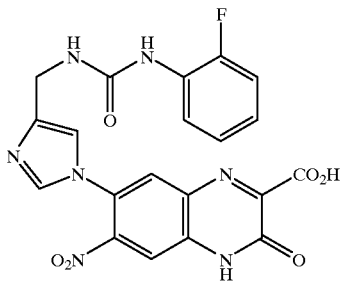

To a solution of the compound in Example 117 (177 mg, 367 μmol) in methanol (5 ml) was added an aqueous (5 ml) solution of potassium carbonate (700 mg, 5.06 mmol), and the mixture was allowed to stand statically for 5 hours at room temperature. This was neutralized with 1N hydrochloric acid and, after allowed to stand statically overnight, the mixture was concentrated under reduced pressure. The residue was made weakly basic with saturated aqueous solution of sodium hydrogencarbonate. The precipitate was collected by filtration, washed with water and then air-dried. The crystals obtained were suspended into N,N-dimethylformamide (2 ml), then 2-fluorophenyl isocyanate (31.0 μl, 282 μmol) was added, and the mixture was stirred for 20 minutes at 60° C. The reaction mixture was concentrated under reduced pressure and the residue was collected by filtration, washed with water, air-dried and then washed with diisopropyl ether. The crystals thus obtained were dissolved into acetic acid-concentrated hydrochloric acid (5:1, 2 ml), which was allowed to stand statically overnight. After the reaction mixture was concentrated under reduced pressure, cold water was added to the residue and the crystals were collected by filtration and washed with water. After air-drying, these were washed with ethyl acetate and dried to obtain 59.9 mg of the title compound as pale brown powder. Yield 33%.

mp 300° C.

Anal.Calcd. for $C_{20}H_{14}FN_7O_6 \cdot 6/5H_2O$: C,49.12;H,3.38;N,20.05. Found:C,49.12;H,3.23;N,19.80.

EXAMPLE 119

7-(4-(((4-Carboxyphenyl)aminocarbonylamino)methyl)imidazolyl)-3,4-dihydro-6-nitro-3-oxoquinoxaline-2-carboxylic Acid

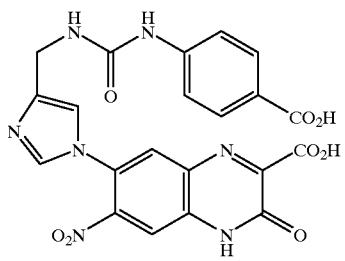

To a solution of the compound in Example 117 (243 mg, 504 μmol) in methanol (7 ml) was added an aqueous (7 ml) solution of potassium carbonate (960 mg, 6.95 mmol), and, after allowed to stand statically overnight, the mixture was concentrated under reduced pressure. Ice water was added to the residue and, after made weakly acidic (pH 4) with 1N hydrochloric acid, the solution was made weakly basic (pH 8) with saturated aqueous solution of sodium hydrogencarbonate, which was concentrated under reduced pressure. The crystals obtained were suspended into N,N-dimethylformamide (2 ml), then ethyl 4-isocyanatobenzoate (145 mg, 758 μmol) was added and the mixture was stirred for 4 hours at 60° C. Ethyl 4-isocyanatobenzoate (55.1 mg, 288 μmol) was added further and the mixture was stirred for 5 hours at 80° C. The reaction mixture was concentrated under reduced pressure and the residue was collected by filtration, washed with water and then air-dried. The crystals thus obtained were dissolved into acetic acid-concentrated hydrochloric acid (5:1, 6 ml) and the mixture was stirred for 8 hours at 30° C. Then, concentrated hydrochloric acid (1 ml) was added additionally and the mixture was stirred for 3 hours at 40° C. After the reaction mixture was concentrated under reduced pressure, a solution of lithium hydroxide monohydrate (105 mg, 2.50 mmol) in methanol-water (1:1, 10 ml) was added to the residue, which was stirred for 2 hours at 50° C. The reaction mixture was concentrated to around half volume under reduced pressure and filtered. The filtrate was brought to pH 3 with 1N hydrochloric acid and the precipitate was collected by filtration and washed with water. After air-drying, these were washed with ethanol and with methanol and dried to obtain 31.0 mg of the title compound as light brown powder. Yield 12%.

mp 300° C. (decomposition).

Anal.Calcd. for $C_{21}H_{15}N_7O_8 \cdot HCl \cdot 4/5H_2O$: C,46.33;H,3.07;N,18.01. Found:C,46.53;H,3.25;N,17.84.

EXAMPLE 120

Ethyl 3-ethoxy-7-(3-(hydroxymethyl)-4-pyridone-1-yl)-6-nitroquinoxaline-2-carboxylate

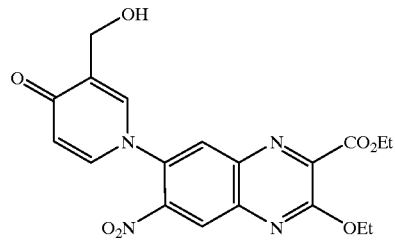

To a solution of 4-chloro-3-(hydroxymethyl)pyridine (2.33 g, 16.2 mmol) in water (25 ml) was added sodium hydroxide (5.20 g, 130 mmol), and the mixture was refluxed for 24 hours. After cooling, the reaction mixture was neutralized with concentrated hydrochloric acid and concentrated under reduced pressure. The residue obtained was dissolved into N,N-dimethylformamide (20 ml), then ethyl 3-ethoxy-7-fluoro-6-nitroquinoxaline-2-carboxylate (500 mg, 1.62 mmol) was added, and the mixture was stirred for 4 hours at 110° C. The reaction mixture was poured into ice water, which was extracted with ethyl acetate. After dried over anhydrous sodium sulfate, solvent was distilled off. The residue obtained was purified by means of silica gel column chromatography [ethyl acetate] to obtain 410 mg of the title compound as yellow powder. Yield 61%.

$^1$H-NMR(CDCl$_3$,δ):1.47(3H,t,J=7.1 Hz),1.54(3H,t,J=7.1 Hz), 4.56(2H,q,J=7.2 Hz),4.59(2H,s),4.68(2H,q,J=7.2 Hz), 6.52(1H,d,J=8.0 Hz),7.41(1H,dd,J=7.3,2.4 Hz),7.45(1H,d,J=2.4 Hz), 8.20(1H,s),8.57(1H,s).

EXAMPLE 121

3,4-Dihydro-6-nitro-3-oxo-7-(3-((N-phenylcarbamoyloxy)methyl)-4-pyridone-1-yl)quinoxaline-2-carboxylic Acid

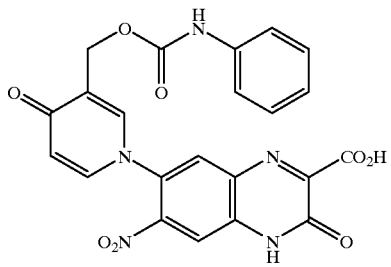

To a solution of the compound in Example 120 (100 mg, 241 μmol) in methylene chloride (1 ml) was added phenyl isocyanate (39.4 μl, 362 μmol), and the mixture was stirred for 8 hours at room temperature. Hexane-methylene chloride (1:1, 3 ml) was added to the reaction mixture and the precipitate was collected by filtration, followed by air-drying. These were dissolved into acetic acid (3 ml), concentrated hydrochloric acid (0.6 ml) was added and the mixture was stirred for 24 hours at room temperature. Water was added to the reaction mixture and the precipitate was collected by filtration, then air-dried to obtain 61.8 mg of the title compound as yellow powder. Yield 51%.

mp 230–232° C. (decomposition).

Anal.Calcd. for $C_{22}H_{15}N_5O_8 \cdot 3/2H_2O$: C,52.39;H,3.60;N,13.88. Found:C,52.70;H,3.41;N,13.81.

HR-FAB–:476.0837 (–0.6 mmu).

EXAMPLES 122 THROUGH 124

Through the same process as in Example 121, compounds listed in following Table 7 were obtained.

TABLE 7

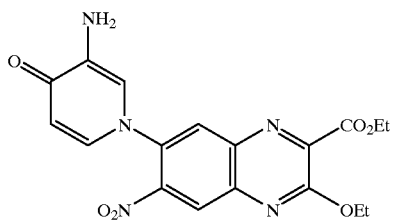

| Example | position |
|---------|----------|
| 122 | para |
| 123 | mela |
| 124 | ortho |

EXAMPLE 122 mp 195–197° C. (decomposition).

Anal.Calcd. for $C_{22}H_{14}BrN_5O_8 \cdot 3/2H_2O$: C,45.30;H,2.94;N,12.01. Found:C,45.20;H,2.63;N,12.17.

HR-FAB–:553.9958 (+1.1 mmu).

EXAMPLE 123 mp 199–201° C. (decomposition).

Anal.Calcd. for $C_{22}H_{14}BrN_5O_8 \cdot H_2O$: C,46.01;H,2.81;N,12.19. Found:C,45.62;H,2.59;N,12.12.

HR-FAB–:553.9988 (+4.1 mmu).

EXAMPLE 124 mp 230–232° C. (decomposition).

HR-FAB–:553.9958 (+1.0 mmu).

EXAMPLE 125

7-(3-((N-(3-Carboxyphenyl)carbamoyloxy)methyl)-4-pyridone-1-yl)-3,4-dihydro-6-nitro-3-oxoquinoxaline-2-carboxylic Acid

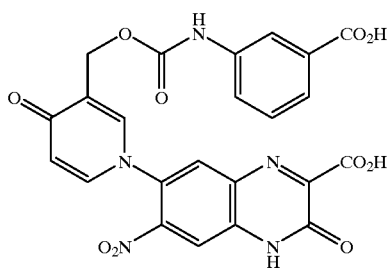

To a solution of the compound in Example 120 (500 mg, 1.21 mmol) in methylene chloride (5 ml) was added ethyl 3-isocyanatobenzoate (302 μl, 1.82 mmol), and the mixture was stirred for 8 hours at room temperature. Hexane-methylene chloride (1:1, 5 ml) was added to the reaction mixture and the precipitate was collected by filtration, followed by air-drying. These were dissolved into acetic acid (15 ml), concentrated hydrochloric acid (3 ml) was added and the mixture was stirred for 24 hours at room temperature. The reaction mixture was concentrated under reduced pressure, water was added and the precipitate was collected by filtration. Then, these were washed with ethyl acetate and air-dried. These were dissolved into 1N aqueous solution of lithium hydroxide (15 ml) and the solution was stirred for 3 hours at room temperature. The insolubles were filtered off and then the solution was made acidic with concentrated hydrochloric acid. The precipitate was collected by filtration, washed with water and then air-dried to obtain 257 mg of the title compound as yellow powder. Yield 38%.

mp 250–252° C. (decomposition).

Anal.Calcd. for $C_{23}H_{15}N_5O_{10} \cdot 5/2H_2O$: C,48.86;H,3.56;N,12.39. Found:C,48.58;H,3.29;N,12.34.

HR-FAB–:520.0735 (–0.6 mmu).

EXAMPLE 126

Ethyl 7-(3-amino-4-pyridone-1-yl)-3-ethoxy-6-nitroquinoxaline-2-carboxylate

A solution of ethyl 3-ethoxy-7-fluoro-6-nitroquinoxaline-2-carboxylate (3.99 g, 12.9 mmol) and 3-amino-4-pyridone (7.10 g, 64.5 mmol) in N,N-dimethylformamide (150 ml) was stirred for 8 hours at 100° C. Solvent was distilled off and the residue obtained was dissolved into methylene chloride. Then, the solution was washed with water, dried over anhydrous sodium sulfate, and solvent was distilled off. The residue obtained was purified by means of silica gel column chromatography [ethyl acetate] to obtain 2.50 g of the title compound as brown powder. Yield 49%.

$^1$H-NMR(CDCl$_3$,δ):1.47(3H,t,J=7.3 Hz),1.53(3H,t,J=7.1 Hz), 4.55(2H,q,J=7.2 Hz),4.67(2H,q,J=7.2 Hz),6.47(1H,d, J=7.3 Hz), 7.03(1H,d,J=2.4 Hz),7.24(1H,dd,J=7.3,2.4 Hz), 8.19(1H,s), 8.49(1H,s).

EXAMPLE 127

Ethyl 7-(3-((4-bromophenyl)aminocarbonylamino)-4-pyridone-1-yl)-3-ethoxy-6-nitroquinoxaline-2-carboxylate

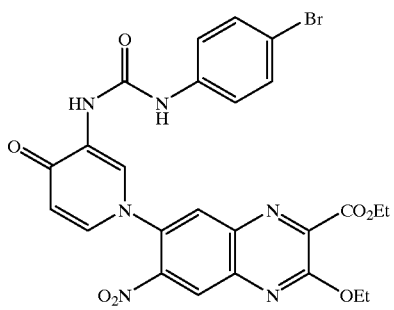

A solution of the compound in Example 126 (69.9 mg, 175 μmol) and 4-bromophenyl isocyanate (34.7 mg, 175 μmol) in methylene chloride (5 ml) was stirred for 3 hours at room temperature. Precipitate was collected by filtration, washed with hexane-methylene chloride (1:1) and then air-dried to obtain 83.0 mg of the title compound as yellow powder. Yield 79%.

$^1$H-NMR(CDCl$_3$,δ):1.37(3H,t,J=6.8 Hz),1.44(3H,t,J=6.8 Hz), 4.48(2H,q,J=6.8 Hz),4.63(2H,q,J=6.8 Hz),6.41(1H,d, J=7.8 Hz), 7.38(2H,d,J=8.9 Hz),7.43(2H,d,J=9.3 Hz),7.95 (1H,dd,J=7.8,2.4 Hz), 8.66(2H,s),8.67(1H,d,J=2.4 Hz),8.71 (1H,s),9.76(1H,s).

EXAMPLE 128

7-(3-((4-Bromophenyl)aminocarbonylamino)-4-pyridone-1-yl)-3,4-dihydro-6-nitro-3-oxoquinoxaline-2-carboxylic Acid

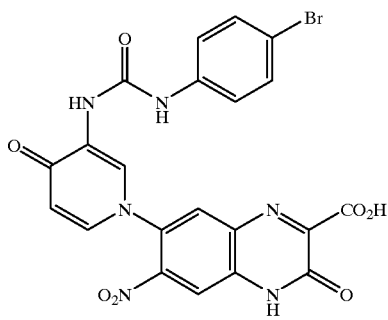

To a solution of the compound in Example 126 (83.0 mg, 139 μmol) in acetic acid (3 ml) was added concentrated hydrochloric acid (0.6 ml), and the mixture was stirred for 24 hours at room temperature. The reaction mixture was poured into water (30 ml) and the precipitate was collected by filtration, washed with water and chloroform in sequence and then air-dried to obtain 72.9 mg of the title compound as yellow powder. Yield 91%.

mp 252–254° C. (decomposition).

Anal.Calcd. for C$_{21}$H$_{13}$BrN$_6$O$_7$.2H$_2$O: C,43.69;H,2.97;N, 14.55. Found:C,43.90;H,2.59;N,14.53.

HR-FAB+:541.0070 (−3.8 mmu).

EXAMPLE 129

3,4-Dihydro-6-nitro-3-oxo-7-(3-(phenylaminocarbonylamino)-4-pyridone-1-yl) quinoxaline-2-carboxylic Acid

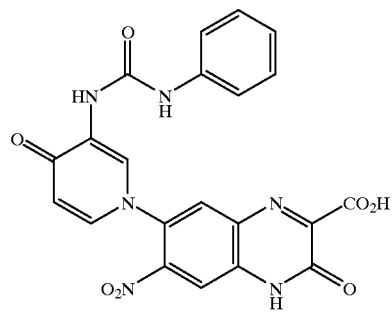

To a solution of the compound in Example 126 (100 mg, 250 μmol) in methylene chloride (5 ml) was added phenyl isocyanate (40.8 μl, 375 μmol), and the mixture was stirred for 8 hours at room temperature. Hexane-methylene chloride (1:1, 3 ml) was added to the reaction mixture and the precipitate was collected by filtration. These were washed with hexane-methylene chloride (1:1) and then air-dried. These were dissolved into acetic acid (3 ml), then concentrated hydrochloric acid (0.6 ml) was added and the mixture was stirred for 24 hours at room temperature. The reaction mixture was poured into water (30 ml) and the precipitate was collected by filtration. These were washed with water and chloroform in sequence and then air-dried to obtain 63.5 mg of the title compound as yellowish brown powder. Yield 54%.

mp 282–284° C. (decomposition).

Anal.Calcd. for C$_{21}$H$_{14}$N$_6$O$_7$.1/2H$_2$O: C,53.51;H,3.21;N, 17.83. Found:C,53.72;H,3.59;N,18.00.

HR-FAB+:463.1020 (+1.8 mmu).

EXAMPLES 130 THROUGH 135

Through the same process as in example 129, compounds listed in following Table 8 were obtained.

TABLE 8

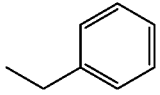

| Example | R | Example | R |
|---|---|---|---|
| 130 | 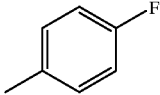 | 133 | 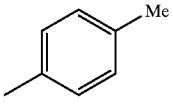 F |
| 131 | 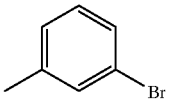 Br | 134 | 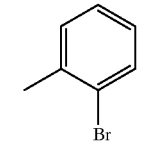 Me |
| 132 | 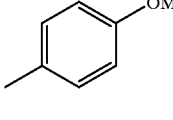 Br | 135 | 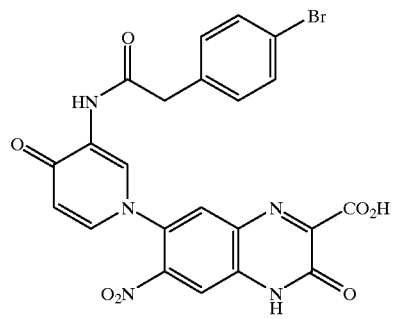 OMe |

EXAMPLE 130 mp 220–222° C. (decomposition).
Anal.Calcd. for $C_{22}H_{16}N_6O_7 \cdot H_2O$: C,53.44;H,3.67;N, 17.00. Found:C,53.60;H,3.59;N,17.02.
HR-FAB+:477.1170 (+1.1 mmu).

EXAMPLE 131 mp 298–300° C. (decomposition).
Anal.Calcd. for $C_{21}H_{31}BrN_6O_7 \cdot H_2O$: C,45.1 0;H,2.70;N, 15.03. Found:C,45.31;H,2.48;N,14.77.
HR-FAB+:541.0086 (−2.1 mmu).

EXAMPLE 132 mp 263–265° C. (decomposition).
Anal.Calcd. for $C_{21}H_{13}BrN_6O_7 \cdot 1/2H_2O$: C,45.84;H,2.56; N,15.27. Found:C,45.69;H,2.65;N,15.09.
HR-FAB+:541.0096 (−1.1 mmu).

EXAMPLE 133 mp 300° C. (decomposition).
HR-FAB+:481.0926 (+1.8 mmu).

EXAMPLE 134 mp 280–282° C. (decomposition).
HR-FAB+:477.1150 (−0.9 mmu).

EXAMPLE 135 mp >300° C. (decomposition).
Anal.Calcd. for $C_{22}H_{16}N_6O_8 \cdot 3/2H_2O$: C,50.87;H,3.69;N, 16.18. Found:C,50.55;H,3.49;N,16.08.
HR-FAB+:493.1119 (+1.1 mmu).

EXAMPLE 136

7-(3-((4-Bromobenzyl)carbonylamino)-4-pyridone-1-yl)-3,4-dihydro-6-nitro-3-oxoquinoxaline-2-carboxylic Acid

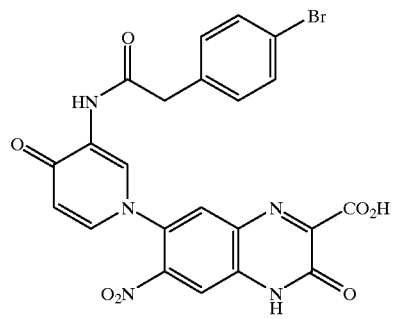

A solution of the compound in Example 126 (100 mg, 250 µmol), 4-bromophenylacetic acid (53.8 mg, 250 µmol) and 1-(3-dimethylaminopropyl)-3-ethylcarbodiimide hydrochloride (71.9 mg, 375 µmol) in methylene chloride (3 ml) was stirred for 8 hours at room temperature. Methylene chloride (50 ml) was added to the reaction mixture, which was washed with water. After dried over anhydrous sodium sulfate, solvent was distilled off. The residue obtained was dissolved into acetic acid (3 ml), concentrated hydrochloric acid (0.6 ml) was added and the mixture was stirred for 24 hours at room temperature. The reaction mixture was poured into water (30 ml) and the precipitate was collected by filtration. These were washed with water and chloroform in sequence and then air-dried to obtain 14.1 mg of the title compound as yellow powder. Yield 10%.

mp 240–242° C. (decomposition).
Anal.Calcd. for $C_{22}H_{14}BrN_5O_7 \cdot H_2O$: C,47.33;H,2.89;N, 12.54. Found:C,46.98;H,3.19;N,12.24.
HR-FAB+:540.0171 (+1.6 mmu).

EXAMPLE 137

7-(3-((4-Bromophenyl)carbonylamino)-4-pyridone-1-yl)-3,4-dihydro-6-nitro-3-oxoquinoxaline-2-carboxylic Acid

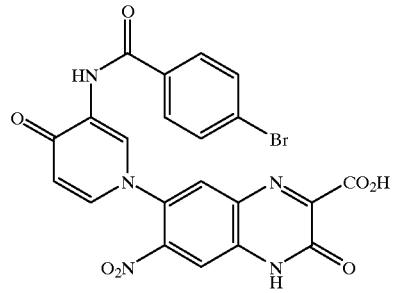

To a solution of the compound in Example 126 (100 mg, 250 µmol) and triethylamine (52.3 µl, 375 µmol) in methylene chloride (3 ml) was added dropwise a solution of 4-bromobenzoyl chloride (65.8 mg, 300 µmol) in methylene chloride (1 ml) at 0° C., and the mixture was stirred for 6 hours at room temperature. Hexane-methylene chloride (1:1, 3 ml) was added to the reaction mixture and the precipitate was collected by filtration. These were washed with hexane-methylene chloride (1:1) and then air-dried. These were dissolved into acetic acid (3 ml), then concentrated hydrochloric acid (0.6 ml) was added and the mixture was stirred for 24 hours at room temperature. The reaction mixture was poured into water (30 ml) and the precipitate was collected by filtration. These were washed with water and chloroform in sequence and then air-dried to obtain 79.2 mg of the title compound as yellow powder. Yield 56%.

mp 230–232° C. (decomposition).

HR-FAB+:526.0009 (+1.1 mmu).

EXAMPLE 138

3,4-Dihydro-7-morpholino-6-nitro-3-oxoquinoxaline-2-carboxylic Morpholineamide

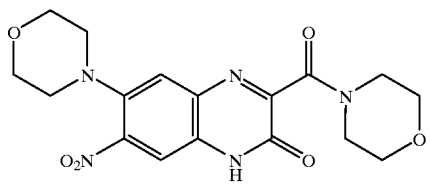

To the compound in Example 2 (195 mg, 694 μmol) was added morpholine (2 ml), and the mixture was stirred for 5 hours at 150° C. in sealed tube. After cooling, the reaction mixture was poured into water and the pH value was brought to 4 using acetic acid. The precipitate was collected by filtration, washed with water and then air-dried to obtain 137 mg of the title compound as dark red powder. Yield 51%.

mp 298–299° C.

Anal.Calcd. for $C_{17}H_{19}N_5O_6$: C52 44;H,4.92;N,17.99. Found:C,52.41;H,4.81;N,17.72.

EXAMPLE 139

Ethyl 3-ethoxy-7-fluoro-6-nitroquinoxaline-2-carboxylate

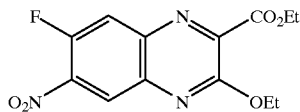

Using the compound in Example 2 (27.4 g, 97.4 mmol) and following the same process as in Example 9, 20.5 g of the title compound were obtained as pale yellow powder. Yield 68%.

$^1$H-NMR(DMSO-$d_6$,δ):1.36(3H,t,J=6.8 Hz),1.41(3H,t,J= 7.3 Hz), 4.47(2H,q,J=6.8 Hz),4.57(2H,q,J=7.3 Hz),8.33(1H, d,J=11.7 Hz), 8.63(1H,d,J=7.8 Hz).

EXAMPLE 140

Ethyl 3-ethoxy-7-(3-fluoro-4-pyridone-1-yl)-6-nitroquinoxaline-2-carboxylate

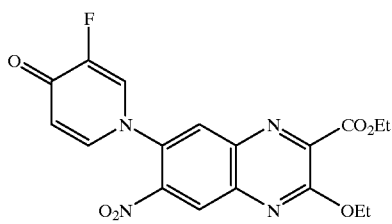

Using the compound in Example 139 (1.00 g, 3.23 mmol) and 3-fluoro-4-pyridone (1.83 g, 16.2 mmol), and following the same process as in Example 32, 930 mg of the title compound were obtained as yellow amorphous material. Yield 72%.

$^1$H-NMR(CDCl$_3$,δ):1.46(3H,t,J=7.1 Hz),1.54(3H,t,J=7.1 Hz), 4.56(2H,q,J=7.2 Hz),4.68(2H,q,J=7.0 Hz),6.68(1H,t,J= 8.1 Hz), 7.36(1H,dd,J=7.6,2.2 Hz),7.55(1H,dd,J=6.3,2.4 Hz),8.22(1H,s), 8.60(1H,s).

EXAMPLE 141

3,4-Dihydro-7-(3-fluoro-4-pyridone-1-yl)-6-nitro-3-oxoquinoxaline-2-carboxylic Acid

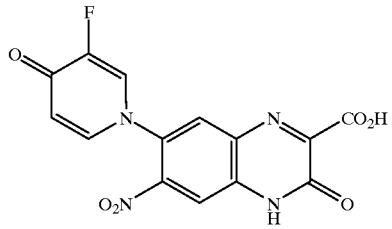

Using the compound in Example 140 (120 mg, 323 μmol) and following the same process as in Example 54, 100 mg of the title compound were obtained as brown powder. Yield 58%.

mp 270–272° C. (decomposition).
HR-FAB+:347.0412 (−1.6 mmu).

EXAMPLE 142

7-(3-Amino-4-pyridone-1-yl)-3,4-dihydro-6-nitro-3-oxoquinoxaline-2-carboxylic Acid To the compound in Example 126 (100 mg, 250 μmol) was added 3N hydrochloric acid (5 ml), and the mixture was stirred for 1 hour at room temperature, which was then allowed to stand statically overnight. After distilled off the solvent, water was added and the precipitate was collected by filtration. These were washed with water and then air-dried to obtain 74.0 mg of the title compound as yellowish brown powder. Yield 58%.

mp >300° C.

Anal.Calcd. for $C_{14}H_9N_5O_6 \cdot 1.9H_2O$: C,44.55;H,3.42;N, 18.55. Found:C,44.17;H,3.02;N,18.28.

HR-FAB−:342.0484 (+0.9 mmu).

EXAMPLE 143

Ethyl 3-ethoxy-7-(4-methylimidazolyl)-6-nitroquinoxaline-2-carboxylate

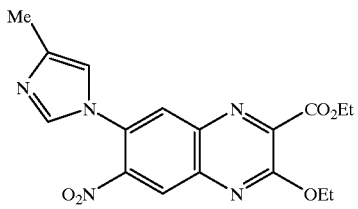

Using the compound in Example 139 (500 mg, 1.62 mmol) and 4-methylimidazole (665 mg, 8.10 mmol), and following the same process as in Example 32, 280 mg of the title compound were obtained as yellowish brown amorphous material. Yield 47%.

$^1$H-NMR(CDCl$_3$,δ):1.47(3H,t,J=7.3 Hz),1.52(3H,t,J=7.1 Hz), 2.31(3H,s),4.55(2H,q,J=7.2 Hz),4.66(2H,q,J=7.0 Hz), 6.83(1H,s), 7.60(1H,d,J=1.5 Hz),8.12(1H,s),8.38(1H,s).

EXAMPLE 144

3,4-Dihydro-7-(4-methylimidazolyl)-6-nitro-3-oxoquinoxaline-2-carboxylic Acid

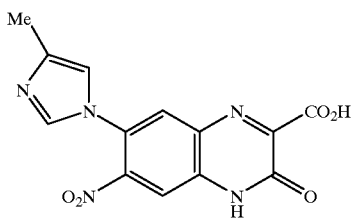

Using the compound in Example 143 (120 mg, 323 μmol) and following the same process as in Example 54, 70.0 mg of the title compound were obtained as brown powder. Yield 69%.

mp 210–212° C. (decomposition).

HR-FAB+:316.0688 (−1.6 mmu).

EXAMPLES 145 THROUGH 149

Using the compound in Example 139 and following through the same process as in Example 31, compounds listed in following Table 9 were obtained.

TABLE 9

| Example | Ar | R | Example | Ar | R |
|---|---|---|---|---|---|
| 145 | (imidazolyl with Me at 2) | Et | 148 | (imidazolyl with Ph) | Et |
| 146 | (imidazolyl with iPr) | Et | 149 | (benzimidazolyl) | Et |
| 147 | (imidazolyl with Me, Me) | Et | | | |

EXAMPLE 145

$^1$H-NMR(CDCl$_3$,δ):1.47(3H,t,J=7.3 Hz),1.53(3H,t,J=7.3 Hz), 2.28(3H,s),4.55(2H,q,J=7.3 Hz),4.67(2H,q,J=7.3 Hz), 6.97(1H,d,J=1.5 Hz),7.01(1H,d,J=1.5 Hz),8.12(1H,s),8.42 (1H,s).

EXAMPLE 146

$^1$H-NMR(CDCl$_3$,δ):1.25(6H,d,J=6.8 Hz),1.47(3H,t,J=7.3 Hz), 1.53(3H,t,J=7.3 Hz),2.71–2.79(1H,m),4.55(2H,q,J=7.3 Hz), 4.67(2H,q,J=7.3 Hz),6.92(1H,d,J=1.0 Hz),7.14(1H,d, J=1.5 Hz), 8.13(1H,s),8.48(1H,s).

EXAMPLE 147

$^1$H-NMR(CDCl$_3$,δ):1.47(3H,t,J=7.3 Hz),1.53(3H,t,J=7.3 Hz), 2.24(6H,s),4.23(3H,s),4.56(2H,q,J=7.3 Hz),4.66(2H,q, J=7.3 Hz), 6.66(1H,s),8.10(1H,s),8.44(1H,s).

EXAMPLE 148

$^1$H-NMR(CDCl$_3$,δ):1.47(3H,t,J=7.3 Hz),1.53(3H,t,J=7.3 Hz), 4.55(2H,q,J=7.3 Hz),4.67(2H,q,J=7.3 Hz),7.30(1H,m), 7.40–7.44(3H,m),7.76(1H,t,J=1.0 Hz),7.82(1H,s), 7.84(1H, d,J=1.5 Hz),8.21(1H,s),8.45(1H,s).

EXAMPLE 149

$^1$H-NMR(CDCl$_3$,δ):1.47(3H,t,J=7.3 Hz),1.55(3H,t,J=7.3 Hz), 4.56(2H,q,J=7.3 Hz),4.70(2H,q,J=7.3 Hz),7.18(1H,t,J= 7.8 Hz), 7.30–7.39(2H,m),7.91(1H,d,J=7.8 Hz),8.08(1H,s), 8.28(1H,s), 8.58(1H,s).

EXAMPLE 150

Ethyl 7-(4-ethoxycarbonylpiperidin-1-1yl)methyl-3-methoxy-6-nitroquinoxaline-2-carboylate

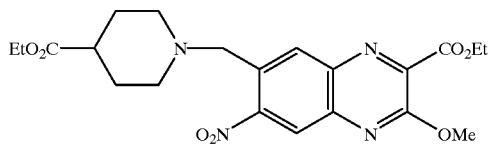

Using the compound in Example 10 (1.05 g, 3.61 mmol) and following the same process as in Example 33, 917 mg of the title compound were obtained as yellowish brown amorphous material. Yield 57%.

$^1$H-NMR(CDCl$_3$,δ):1.25(3H,t,J=7.3 Hz),1.47(3H,t,J=7.3 Hz), 1.70–1.76(2H,m),1.82–1.85(2H,m),2.12–2.17(2H,m), 2.24–2.30(1H,m),2.76–2.78(2H,m),3.87(2H,s),4.12(2H,q, J=7.3 Hz), 4.17(3H,s),4.54(2H,q,J=7.3 Hz),8.20(1H,s),8.26 (1H,s).

EXAMPLE 151

3,4-Dihydro-7-(2-methylimidazolyl)-6-nitro-3-oxoquinoxaline-2-carboxylic Acid

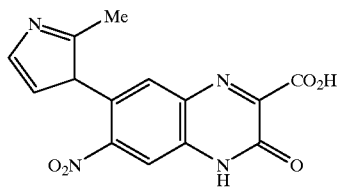

To a solution of the compound in Example 145 (218 mg, 587 μmol) in acetic acid (10 ml) was added concentrated hydrochloric acid (700 μl), and the mixture was stirred for 23 hours at room temperature. After distilled off the solvent, water was added and the precipitate was collected by filtration, followed by air-drying, to obtain 97.4 mg of the title compound as brown powder. Yield 53%.

mp 268–271° C. (decomposition).
HR-FAB–:314.0514(–1.2 mmu).

EXAMPLES 152 THROUGH 154

Through the same process as in Example 151, compounds listed in following Table 10 were obtained.

TABLE 10

| Example | Ar |
|---|---|
| 152 | ![imidazole with isopropyl] |
| 153 | ![benzimidazole N-methyl] |
| 154 | ![N-ethylpiperidine-CO2H] |

EXAMPLE 152 mp 243–245° C. (decomposition).
HR-FAB–:342.0837 (–0.1 mmu).

EXAMPLE 153 mp 229–231° C. (decomposition).
Anal.Calcd. for $C_{16}H_9N_5O_5$.HCl: C,49.56;H,2.60;N, 18.06. Found:C,49.68;H,2.77;N,18.16.
HR-FAB–:350.0545 (+1.9 mmu).

EXAMPLE 154 mp 254–256° C. (decomposition).
Anal.Calcd. for $C_{16}H_{16}N_4O_7$.HCl.1/10H$_2$O: C,46.35; H,4.18;N,13.51. Found:C,46.36;H,4.21;N,13.72.
HR-FAB–:375.0954 (+1.4 mmu).

EXAMPLE 155

Ethyl 3-ethoxy-7-(4-methoxybenzyl)amino-6-nitroquinoxaline-2-carboxylate

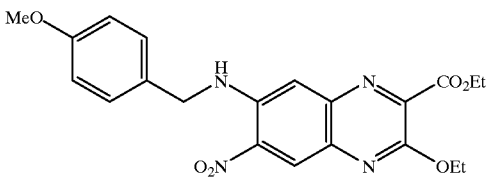

To a solution of the compound in Example 139 (2.00 g, 6.47 mmol) in tetrahydrofuran (15 ml) were added 4-methoxybenzylamine (1.06 g, 7.76 mmol) and successively triethylamine (785 mg, 7.76 mmol), and the mixture was refluxed for 24 hours. After cooling, ethyl acetate was added and the solution was washed with brine. After the organic layer was dried over anhydrous magnesium sulfate, the residue obtained by distilling off the solvent was purified by means of silica gel column chromatography [methylene chloride methylene chloride-methanol (50:1)] to obtain 2.09 g of the title compound as purple powder. Yield 76%.

$^1$H-NMR(DMSO-d$_6$,δ):1.32(3H,t,J=7.3 Hz),1.37(3H,t,J= 7.3 Hz), 3.72(3H,s),4.41(2H,q,J=7.3 Hz),4.47(2H,q,J=7.3

Hz), 4.58(2H,d,J=6.3 Hz),6.91(2H,d,J=8.8 Hz),7.22(1H,s), 7.37(2H,d,J=8.8 Hz),8.08(1H,t,J=6.3 Hz),8.49(1H,s).

EXAMPLE 156

Ethyl 7-amino-3-ethoxy-6-nitroquinoxaline-2-carboxylate

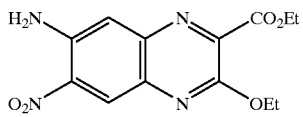

To a solution of the compound in Example 155 (2.09 g, 4.90 mmol) in anisole (5 ml) was added trifluoroacetic acid (5 ml), and the mixture was stirred for 6 hours at room temperature. The residue obtained by concentrating the reaction mixture was purified by means of silica gel column chromatography [methylene chloride] to obtain 1.20 g of the title compound as purple powder. Yield 80%.

$^1$H-NMR(DMSO-$d_6$,δ):1.35(3H,t,J=6.8 Hz),1.37(3H,t,J= 7.3 Hz), 4.43(2H,q,J=7.3 Hz),4.47(2H,q,J=6.8 Hz),7.12(2H, s),7.49(1H,s), 8.41(1H,s).

EXAMPLE 157

7-Amino-3,4-dihydro-6-nitro-3-oxoquinoxaline-2-carboxylic Acid

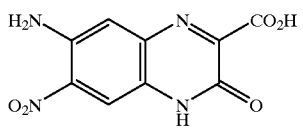

To a solution of the compound in Example 156 (200 mg, 653 μmol) in ethanol (10 ml) were added 1N aqueous solution of potassium hydroxide (1.96 ml, 1.96 mmol) and water (2 ml), and the mixture was refluxed for 30 minutes. After cooling, the pH value was brought to 4 using 10% hydrochloric acid and brine was added, which was extracted with chloroform. After the organic layer was dried over anhydrous magnesium sulfate, solvent was distilled off to obtain 159 mg of reddish brown powder. This was dissolved into ethanol (10 ml), then concentrated hydrochloric acid (2 ml) was added and the mixture was stirred for 24 hours at room temperature. Solvent was distilled off, the residue was washed with water and diisopropyl ether in sequence and then air-dried to obtain 156 mg of the title compound as brown powder. Yield 95%.

mp 300° C. HR-MS:250.0311 (−2.7 mmu).

EXAMPLE 158

3,4-Dihydro-6-nitro-3-oxo-7-(pyrrole-1-yl) quinoxaline-2-carboxylic Acid

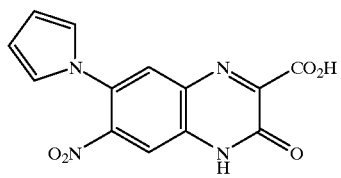

To a solution of the compound in Example 157 (50.0 mg, 200 μmol) in acetic acid (5 ml) was added 2,5-dimethoxytetrahydrofuran (31.7 mg, 240 μmol), and the mixture was stirred for 4 hours at 80° C. The reaction mixture was concentrated and then the residue was washed with water and diisopropyl ether in sequence to obtain 28.0 mg of the title compound as brown powder. Yield 47%.

mp >300° C.

HR-MS:300.0502 (+0.7 mmu).

EXAMPLE 159

Ethyl 3-methoxy-7-(morpholine-1-yl)methyl-6-nitroquinoxaline-2-carboxylate

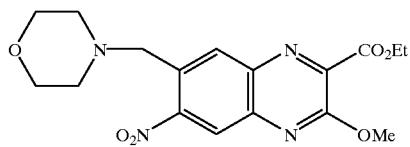

Using the compound in Example 10 (792 mg, 2.72 mmol) and following the same process as in Example 33, 488 mg of the title compound were obtained as a brown oil. Yield 48%.

$^1$H-NMR(CDCl$_3$,δ):1.47(3H,t,J=6.9 Hz),2.44–2.47(2H, m),3.64–3.66(2H,m),3.90(2H,s),4.17(3H,s),4.54(2H,q,J= 6.9 Hz), 8.19(1H,s),8.27(1H,s).

EXAMPLE 160

3,4-Dihydro-7-(morpholine-1-yl)methyl-6-nitro-3-oxoquinoxaline-2-carboxylic Acid Hydrochloride

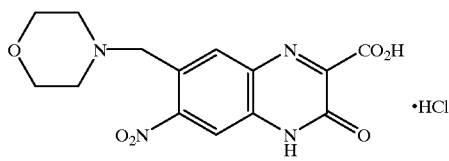

Using the compound in Example 159 (487 mg, 1.29 mmol) and following the same process as in Example 151, 125 mg of the title compound were obtained as brown powder. Yield 26%.

mp 209–211° C. (decomposition).

Anal.Calcd. for C$_{14}$H$_{14}$N$_4$O$_6$.HCl: C,45.36;H,4.08;N, 15.11. Found:C,45.31;H,4.35;N,15.15.

HR-FAB+:335.1004 (+1.2 mmu).

EXAMPLE 161

Ethyl 3,4-dihydro-7-fluoro-4-methyl-6-nitro-3-oxoquinoxaline-2-carboxylate

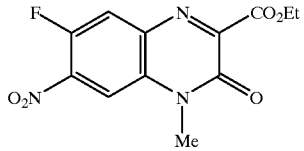

To a solution of the compound in Example 2 (345 mg, 1.23 mmol) in N,N-dimethylformamide (10 ml) were added a 50% dispersion of sodium hydride in oil (61.3 mg, 1.54 mmol), and the mixture was stirred for 30 minutes at room temperature. Then, after added methyl iodide (95.5 ml, 1.54 mmol), the mixture was stirred further for 2 hours. The reaction mixture was poured into ice water, which was extracted with ethyl acetate. After the organic layer was dried over anhydrous sodium sulfate, solvent was distilled off under reduced pressure. The residue obtained was purified by means of silica gel column chromatography [hexane-ethyl acetate=5:2] to obtain 272 mg of title compound as pale yellow powder. Yield 75 %.

$^1$H-NMR(CDCl$_3$,δ):1.45(3H,t,J=7.3 Hz),3.77(3H,s), 4.53 (2H,q,J=7.3 Hz),7.87(1H,d,J=10.3 Hz),8.04(1H,d,J=6.3 Hz).

EXAMPLE 162

3,4-Dihydro-7-fluoro-4-methyl-6-nitro-3-oxoquinoxaline-2-carboxylic Acid

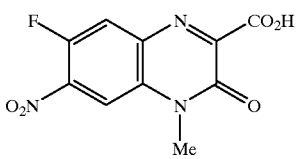

Using the compound in Example 161 (207 mg, 701 μmol) and following the same process as in Example 62, 78.4 mg of title compound were obtained as greenish brown powder. Yield 41%.

mp 173–175° C.

Anal.Calcd. for C$_{10}$H$_6$FN$_3$O$_5$.1/5H$_2$O: C,44.36;H,2.38;N, 15.52. Found:C,44.33;H,2.25;N,15.79.

HR-FAB+:268.0366 (−0.4 mmu).

EXAMPLE 163

3,4-Dihydro-6-nitro-3-oxo-7-trifluoromethylquinoxaline-2-carboxylic Acid

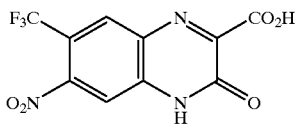

To a solution of ethyl 3,4-dihydro-6-nitro-3-oxo-7-trifluoromethylquinoxaline-2-carboxylate (120 mg, 362 μmol) in ethanol (5 ml) was added 1N aqueous solution of potassium hydroxide (724 μl, 724 μmol), and the mixture was refluxed for 1 hour. After cooling, water was added and the p$^H$ value was brought to 2 with concentrated hydrochloric acid. The precipitate was collected by filtration, washed with water and then air-dried to obtain 102 mg of the title compound as colorless powder. Yield 88%.

mp 213–215° C. (decomposition).

Anal.Calcd. for C$_{10}$H$_4$F$_3$N$_3$O$_5$.H$_2$O: C,37.40;H,1.88;N, 13.08. Found:C,37.71;H,1.94;N,13.01.

HR-MS:303.0113 (+1.0 mmu).

EXAMPLE 164

7-Amino-3,4-dihydro-3-oxo-6-trifluoromethylquinoxaline-2-carboxylic Acid

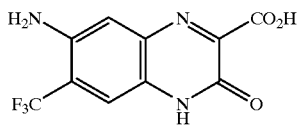

To a solution of ethyl 7-amino-3,4-dihydro-3-oxo-6-trifluoromethylquinoxaline-2-carboxylate (55.9 mg, 186 μmol) in ethanol (2 ml) was added 1N aqueous solution of potassium hydroxide (446 μl, 446 μmol), and the mixture was refluxed for 1.5 hours. After cooling, solvent was distilled off, water was added and the pH value was brought to 2 with 4N hydrochloric acid. Solvent was distilled off again and small quantity of water was added. The crystals were collected by filtration, washed with water and then air-dried to obtain 24.2 mg of the title compound as dark red powder. Yield 45%.

mp 218–220° C. (decomposition).

Anal.Calcd. for C$_{10}$H$_6$F$_3$N$_3$O$_3$.H$_2$O: C,41.24;H,2.77;N, 14.43. Found:C,40.96;H,2.70;N,14.26.

HR-MS:273.0337 (−2.4 mmu).

EXAMPLE 165

3,4-Dihydro-3-oxo-7-(pyrrole-1-yl)-6-trifluoromethylquinoxaline-2-carboxylic Acid

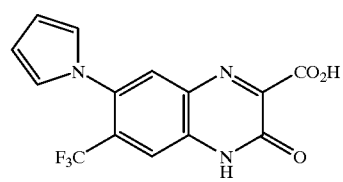

To a solution of ethyl 3,4-dihydro-3-oxo-7-(pyrrole-1-yl)-6-trifluoromethylquinoxaline-2-carboxylate (67.0 mg, 191 μmol) in ethanol (2 ml) was added 1N aqueous solution of potassium hydroxide (382 μl, 382 μmol), and the mixture was refluxed for 1 hour. After cooling, the residue obtained by distilling off the solvent was dissolved into water and the pH value was brought to 2 with 4N hydrochloric acid. This was extracted with ethyl acetate and, after dried over anhydrous sodium sulfate, solvent was distilled off. Small quantity of water was added to the residue obtained. The crystals were collected by filtration, washed with water and then air-dried to obtain 52.9 mg of the title compound as yellowish brown powder. Yield 86%.

mp 136–138° C. (decomposition).

HR-FAB−:322.0424 (−1.6 mmu).

EXAMPLE 166

Ethyl 3,4-dihydro-7-imidazolyl-3-oxo-6-trifluoromethylquinoxaline-2-carboxylate

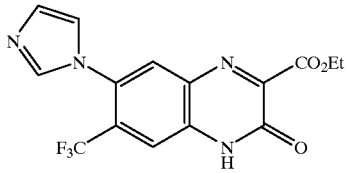

To a solution of 5-imidazolyl-4-trifluoromethyl-1,2-phenylenediamine (303 mg, 1.25 mmol) in ethanol (50 ml) was added diethyl ketomalonate (210 μl, 1.38 mmol) at room temperature, and the mixture was refluxed for 6 hours. The reaction mixture. was concentrated to around half volume under reduced pressure, then the precipitate was collected by filtration and washed with cold ethanol. The filtrate was distilled off under reduced pressure, small quantity of mixed solution of ethyl acetate-diisopropyl ether was added to the residue obtained and the precipitate was collected by filtration to obtain 148 mg of the title compound as pale yellowish brown powder. Yield 34%.

$^1$H-NMR(DMSO-d$_6$,δ):1.34(3H,t,J=7.4 Hz),4.41(2H,q,J=7.4 Hz), 7.14(1H,s),7,33(1H,s),7.49(1H,s),7.93(2H,s),8.39 (1H,s), 13.30(1H,brs).

EXAMPLE 167

Ethyl 3,4-dihydro-3-oxo-7-(4-pyridone-1-yl)-6-trifluoromethylquinoxaline-2-carboxylate

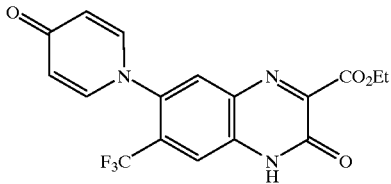

To a solution of 4-(4-pyridone-1-yl)-5-trifluoromethyl-2-nitroaniline (210 mg, 701 μmol) in ethanol (10 ml) was added 10% palladium-carbon (40.0 mg) at room temperature, and the catalytic hydrogenation was conducted for 2 hours at ambient temperature under ambient pressure. Catalyst was filtered off using celite and the filtrate was distilled off under reduced pressure. After dissolved this into ethanol (3 ml), diethyl ketomalonate (214 μl, 1.40 mmol) was added and the mixture was refluxed for 5 hours. The residue obtained by concentrating the reaction mixtnre was purified by means of silica gel column chromatography [methylene chloride-ethanol (50:1 6:1)] to obtain 158 mg of the title compound as pale yellow powder. Yield 59%.

$^1$H-NMR(DMSO-d$_6$,δ):1.33(3H,t,J=7.3 Hz),4.41(2H,q,J=7.3 Hz), 6.19(2H,d,J=7.3 Hz),7.72(2H,d,J=7.3 Hz),8.33(1H, s), 13.32(1H,brs).

EXAMPLE 168

3,4-Dihydro-7-imidazolyl-3-oxo-6-trifluoromethylquinoxaline-2-carboxylic Acid

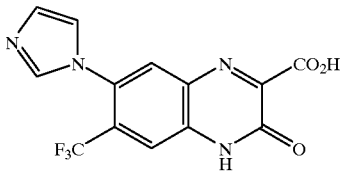

To a solution of the compound in Example 166 (141 mg, 400 μmol) in acetic acid (5 ml) was added 6N hydrochloric acid at room temperature, and the mixture was stirred for 3.5 hours at 80° C. Ethyl acetate was added to the residue obtained by distilling off solvent under reduced pressure. This was washed with brine, dried over anhydrous sodium sulfate and solvent was distilled off under reduced pressure. Small quantity of water was added to the residue obtained, which was stirred for 30 minutes under ice-cooling. The precipitate was collected by filtration and further recrystallized from water to obtain 48.7 mg of the title compound as light reddish brown powder. Yield 38%.

mp 232–234° C. (decomposition).

Anal.Calcd. for $C_{13}H_7F_3N_4O_3$·2H$_2$O: C,43.34;H,3.08;N, 15.55. Found:C,43.20;H,2.70;N,15.45.

HR-FAB−:323.0396 (+0.4 mmu).

EXAMPLE 169

3,4-Dihydro-3-oxo-7-(4-pyridone-1-yl)-6-trifluoromethylquinoxaline-2-carboxylic Acid

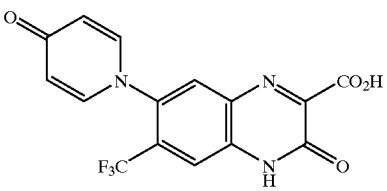

To a solution of the compound in Example 167 (100 mg, 264 μmol) in ethanol (3 ml) was added 1N aqueous solution of lithium hydroxide (659 μl, 659 μmol), and the mixture was stirred for 1.5 hours at 50° C. After cooling, the insolubles were filtered off and the pH value was brought to 4 with 3N hydrochloric acid. The precipitate was collected by filtration, washed with water and then air-dried to obtain 83.0 mg of the title compound as colorless powder. Yield 90%.

mp 300° C.

Anal.Calcd. for $C_{15}H_8F_3N_3O_4$: C,51.29;H,2.30;N,11.96. Found:C,51.27;H,2.46;N,11.62.

EXAMPLE 170

Ethyl 6-(aminosulfonyl)-7-chloro-3,4-dihydro-3-oxoquinoxaline-2-carboxylate

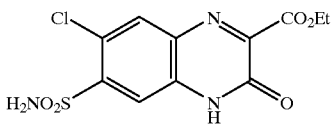

To a solution of 4-amino-2-chloro-5-nitrobenzenesulfonamide (2.00 g, 7.95 mmol) in methanol (40 ml) were added 10% palladium-carbon (400 mg) and successively 10% hydrochloric acid (6 ml) at room temperature, and catalytic hydrogenation was conducted for 2 hours at ambient temperature under ambient pressure. Catalyst was filtered off using celite and the filtrate was distilled off under reduced pressure. After dissolved this into ethanol (16 ml), diethyl ketomalonate (1.21 ml, 7.95 mmol) was added, which was stirred for 5 hours at room temperature. The precipitate was collected by filtration, washed with ethanol and then purified by means of silica gel column chromatography [hexane-ethyl acetate=1:2] to obtain 288 mg of the title compound. Yield 11%.

$^1$H-NMR(DMSO-d$_6$,δ):1.32(3H,t,J=6.9 Hz),3.33(3H,s), 4.39(2H,q,J=7.4 Hz),7.87(1H,s),8.01(1H,s),8.12(1H,s).

EXAMPLE 171

6-(Aminosulfonyl)-7-chloro-3,4-dihydro-3-oxoquinoxaline-2-carboxylic Acid

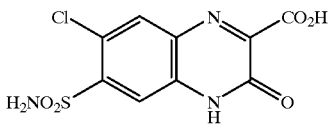

To a suspension of the compound in Example 170 (200 mg, 603 μmol) in ethanol (6 ml) was added 1N aqueous solution of potassium hydroxide (1.21 ml, 1.21 mmol), and the mixture was refluxed for 3 hours. Water was added to the reaction mixture, the pH value was brought to 4 with acetic acid and solvent was distilled off. The residue obtained was purified by synthetic adsorbent Sepabeads ® SP850 [water water-acetonitrile (20:1 4:1)] to obtain 58.5 mg of the title compound as yellow powder. Yield 32%.

mp 213–214° C. (decomposition).

Anal.Calcd. for C$_9$H$_6$ClNO$_3$S.4/5H$_2$O: C,33.98;H, 2.41;N,13.21. Found:C,34.15;H,2.72;N,12.96.

HR-FAB–:303.9837 (+4.2 mmu).

EXAMPLE 172

Ethyl 3-ethoxy-7-fluoro-6-methanesulfonylquinoxaline-2-carboxylate

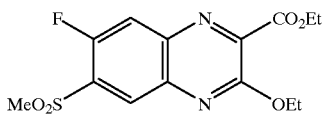

To a solution of ethyl 3-ethoxy-7-fluoro-6-methylthioquinoxaline-2-carboxylate (450 mg, 1.45 mmol) in chloroform (15 ml) was added 3-chloroperbenzoic acid (715 mg, 2.90 mmol) at room temperature, and the mixture was stirred for 3 hours at room temperature. Calcium hydroxide was added to the reaction liquor and the mixture was stirred for 10 minutes. Then, the insolubles were filtered off using celite and the filtrate was distilled off under reduced pressure. The residue obtained was purified by means of silica gel column chromatography [methylene chloride] to obtain 496 mg of the title compound as colorless solids. Quantitative yield.

$^1$H-NMR(CDCl$_3$,δ):1.47(3H,t,J=6.9 Hz),1.50(3H,t,J=6.9 Hz), 3.33(3H,s),4.54(2H,q,J=6.9 Hz),4.61(2H,q,J=6.9 Hz), 7.89(1H,d,J=10.3 Hz),8.52(1H,d,J=6.9 Hz).

EXAMPLE 173

3-Ethoxy-7-fluoro-6-methanesulfonylquinoxaline-2-carboxylic Acid

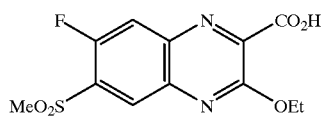

To a solution of the compound in Example 172 (262 mg, 765 μmol) in ethanol (8 ml) was added 1N aqueous solution of potassium hydroxide (1.53 ml, 1.53 mmol), and the mixture was refluxed for 1.5 hours. Water was added to the reaction mixture and the pH value was brought to 3 with concentrated hydrochloric acid, which was extracted with ethyl acetate. After the organic layer was dried over anhydrous sodium sulfate, solvent was distilled off under reduced pressure to obtain 199 mg of the title compound as yellowish brown powder. Yield 83%.

$^1$H-NMR(CDCl$_3$,δ):1.56(3H,t,J=6.9 Hz),3.35(3H,s), 4.70 (2H,q,J=6.9 Hz),7.93(1H,d,J=9.3 Hz),8.58(1H,d,J=6.8 Hz).

EXAMPLE 174

3,4-Dihydro-7-fluoro-6-methanesulfonyl-3-oxoquinoxaline-2-carboxylic Acid

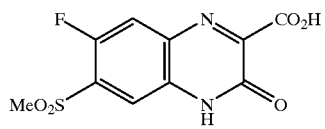

To a solution of the compound in Example 173 (149 mg, 474 μmol) in acetic acid (3 ml) was added concentrated hydrochloric acid (1.5 ml) at room temperature, and the mixture was stirred for 24 hours at room temperature. The reaction mixture was distilled off under reduced pressure. The residue obtained was purified with synthetic adsorbent Sepabeads® SP850 [water water-acetonitrile (20:1 4:1)] to obtain 37.2 mg of the title compound as yellow powder. Yield 27%.

mp 190–192° C.

Anal.Calcd. for C$_{10}$H$_7$FN$_2$O$_5$S.H$_2$O: C,39.48;H,2.98;N, 9.21. Found:C,39.60;H,2.62;N,9.01.

HR-FAB–:286.0089 (+2.9 mmu).

EXAMPLE 175

7-Bromo-3,4-dihydro-3-oxo-6-trifluoromethylquinoxaline-2-carboxylic Acid

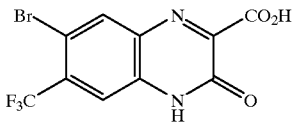

To a solution of ethyl 7-bromo-3,4-dihydro-3-oxo-6-trifluoromethylquinoxaline-2-carboxylate (120 mg, 329 µmol) in ethanol (4 ml) were added 1N aqueous solution of potassium hydroxide (1.32 ml, 1.32 mmol) and water (2 ml), and the mixture was refluxed for 30 minutes. After cooling with ice, the pH value was brought to 4 with 1.2N hydrochloric acid. The precipitate was collected by filtration, washed with water and then air-dried to obtain 91.0 mg of the title compound as yellowish brown powder. Yield 82%.

mp 210–212° C. (decomposition).

HR-MS:335.9358 (+0.1 mmu).

EXAMPLE 176

Ethyl 3,4-dihydro-7-(3-formylpyrrole-1-yl)-3-oxo-6-trifluoromethylquinoxaline-2-carboxylate

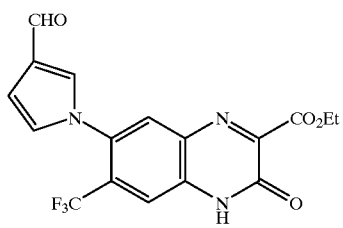

To a solution of the compound in Example 73 (2.00 g, 5.25 mmol) in 1,4-dioxane (100 ml) was added 2,3-dichloro-5,6-dicyanoquinone (1.25 g, 5.50 mmol), and the mixture was stirred for 3 hours at room temperature. The precipitate was filtered off and the residue obtained by distilling off solvent was purified by means of silica gel column chromatography [ethyl acetate-hexane=2:1] to obtain 1.88 g of the title compound as yellow amorphous material. Yield 94%.

$^1$H-NMR(DMSO-$d_6$,δ):1.33(3H,t,J=7.3 Hz),4.41(2H,q,J= 7.3 Hz), 6.66(1H,dd,J=3.4,1.5 Hz),7.13(1H,s),7.79(1H,s), 7.88(1H,s), 8.15(1H,s),9.79(1H,s),13.28(1H,s).

EXAMPLE 177

3,4-Dihydro-7-(3-formylpyrrole-1-yl)-3-oxo-6-trifluoromethylquinoxaline-2-carboxylic Acid

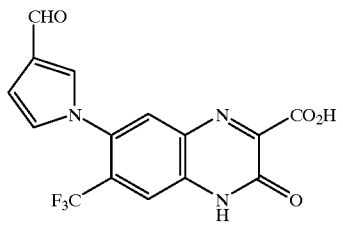

To a solution of the compound in Example 176 (142 mg, 375 µmol) in ethanol (7.5 ml) was added 1N aqueous solution of potassium hydroxide (825 µl, 825 µmol), and the mixture was refluxed for 1 hour. After cooling, solvent was distilled off, the residue was dissolved into small amount of water and then the pH value was brought to 2 using 4N hydrochloric acid. The precipitate was collected by filtration, washed with water and then air-dried to obtain 83.2 mg of the title compound as yellowish brown powder. Yield 61%.

mp 158–160° C. (decomposition).

Anal.Calcd. for $C_{23}H_{16}F_3N_5O_6 \cdot 2/3H_2O$: C,49.59;H, 2.59;N,11.57. Found:C,49.43;H,2.73;N,11.34.

HR-FAB+:352.0536 (−0.9 mmu).

EXAMPLE 178

Ethyl 3,4-dihydro-7-(3-((( 2-fluorophenyl) aminocarbonylamino)methyl)pyrrole-1-yl)-3-oxo-6-trifluoromethylquinoxaline-2-carboxylate

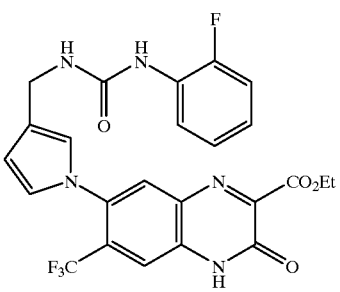

To a solution of the compound in Example 74 (180 mg, 430 µmol) in N,N-dimethylformamide (4.3 ml) were added triethylamine (89.9 µl, 645 µmol) and 2-fluorophenyl isocyanate (57.9 µl, 516 µmol) at room temperature, and the mixture was stirred for 4 hours at the same temperature. The reaction mixture was poured into water (50 ml), which was extracted with ethyl acetate. After dried over anhydrous sodium sulfate, solvent was distilled off. Methylene chloride was added to the residue obtained. The precipitate was collected by filtration, washed with methylene chloride and then air-dried to obtain 111 mg of a mixture of the title compound and tetrahydrated compound thereof (around 3:2) as yellow powder. After dissolved these into 1,4-dioxane (4 ml), 2,3-dichloro-5,6-dicyanoquinone (23.6 mg, 104 µmol: use level was varied depending on the formation ratio) was added and the mixture was refluxed for 1 hour. After cooling, the precipitate was filtered off and solvent was distilled off. Methylene chloride was added to the residue obtained. The precipitate was collected by filtration, washed with methylene chloride and then air-dried to obtain 75.5 mg of the title compound as yellowish brown powder. Yield 34%.

$^1$H-NMR(DMSO-$d_6$,δ):1.32(3H,t,J=6.9 Hz),4.19(2H,d,J= 5.4 Hz), 4.40(2H,q,J=6.9 Hz),6.24(1H,t,J=2.0 Hz),6.83(1H, d,J=5.4 Hz), 6.89–6.94(1H,m),6.920(1H,s),6.924(1H,s), 7.08(1H,t,J=7.8 Hz), 7.14–7.19(1H,m),7.75(1H,s),7.92(1H, s),8.14–8.19(1H,m), 8.33(1H,d,J=2.4 Hz),13.22(1H,s).

EXAMPLE 179

Ethyl 3,4-dihydro-7-(3-(((3-fluorophenyl)aminocarbonylamino)methyl)pyrrole-1-yl)-3-oxo-6-trifluoromethylquinoxaline-2-carboxylate

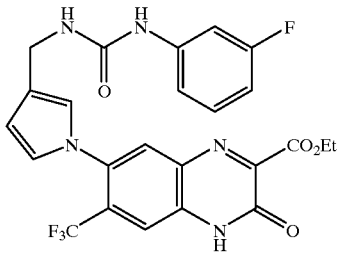

Using the compound in Example 74 (180 mg, 430 μmol) and 3-fluorophenyl isocyanate (58.9 μl, 516 μmol), and following the same process as in Example 178, 95.9 mg of the title compound were obtained as yellowish brown powder. Yield 43%.

$^1$H-NMR(DMSO-d$_6$,δ):1.32(3H,t,J=6.8 Hz),4.18(2H,d,J=5.4 Hz), 4.40(2H,q,J=6.8 Hz),6.24(1H,t,J=2.0 Hz),6.41(1H,d,J=5.4 Hz), 6.69(1H,td,J=8.3,2.5 Hz),6.910(1H,s),6.914 (1H,s), 7.00–7.02(1H,m),7.23(1H,dd,J=15.2,8.3 Hz), 7.47 (1H,dt,J=12.7,2.5 Hz),7.75(1H,s),7.91(1H,s),8.72(1H,s), 13.22(1H,s).

EXAMPLE 180

Ethyl 3,4-dihydro-7-(3-(((4-fluorophenyl)aminocarbonylamino)methyl)pyrrole-1-yl)-3-oxo-6-trifluoromethylquinoxaline-2-carboxylate

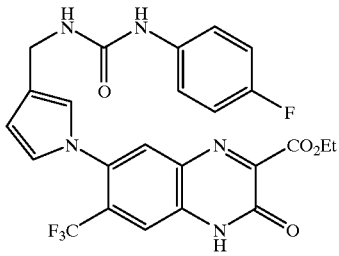

Using the compound in Example 74 (180 mg, 430 μmol) and 4-fluorophenyl isocyanate (58.7 μl, 516 μmol) and following the same process as in Example 178, 132 mg of the title compound were obtained as yellowish brown powder. Yield 59%.

$^1$H-NMR(DMSO-d$_6$,δ):1.32(3H,t,J=6.8 Hz),4.17(2H,d,J=5.4 Hz), 4.40(2H,q,J=6.8 Hz),6.24(1H,t,J=2.0 Hz),6.30(1H,d,J=5.4 Hz), 6.90(1H,s),6.91(1H,s),7.03–7.08(2H,m), 7.38–7.41(2H,m), 7.75(1H,s),7.91(1H,s),8.49(1H,s),13.22 (1H,s).

EXAMPLE 181

3,4-Dihydro-7-(3-(((2-fluorophenyl)aminocarbonylamino)methyl)pyrrole-1-yl)-3-oxo-6-trifluoromethylquinoxaline-2-carboxylic Acid

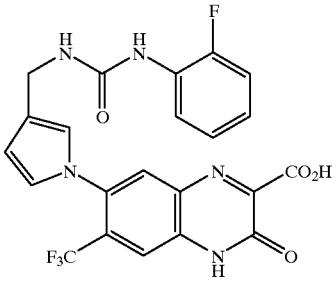

To a solution of the compound in Example 178 (74.0 mg, 143 μmol) in ethanol (3 ml) was added 1N aqueous solution of potassium hydroxide (715 μl, 715 μmol), and the mixture was refluxed for 1 hour. After cooling, solvent was distilled off, and the residue was dissolved into small quantity of water, then the pH value was brought to 2 using 4N hydrochloric acid. The precipitate was collected by filtration, washed with water and then air-dried to obtain 37.1 mg of the title compound as yellowish brown powder. Yield 53%.

mp 177–179° C.

HR-FAB–:488.0985 (–0.9 mmu).

EXAMPLE 182

3,4-Dihydro-7-(3-(((3-fluorophenyl)aminocarbonylamino)methyl)pyrrole-1-yl)-3-oxo-6-trifluoromethylquinoxaline-2-carboxylic Acid

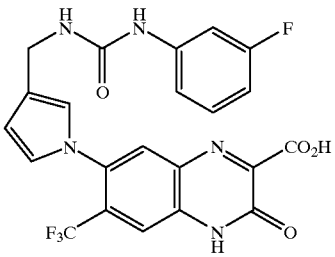

Using the compound in Example 179 (131 mg, 253 μmol) and following the same process as in Example 181, 73.6 mg of the title compound were obtained as yellowish brown powder. Yield 83%.

mp 169–171° C.

HR-FAB–:488.0991 (+0.9 mmu).

EXAMPLE 183

3,4-Dihydro-7-(3-(((4-fluorophenyl)aminocarbonylamino)methyl)pyrrole-1-yl)-3-oxo-6-trifluoromethylquinoxaline-2-carboxylic Acid

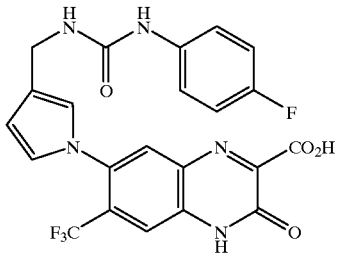

Using the compound in Example 180 (94.4 mg, 182 μmol) and following the same process as in Example 181, 90.3 mg of the title compound were obtained as yellowish brown powder. Yield 73%.

mp 168–170° C.

HR-FAB–:488.0985(+0.3 mmu).

EXAMPLE 184

Ethyl 7-(3-(((4-bromophenyl)aminocarbonylamino)methyl)pyrrole-1-yl)-3,4-dihydro-3-oxo-6-trifluoromethylquinoxaline-2-carboxylate

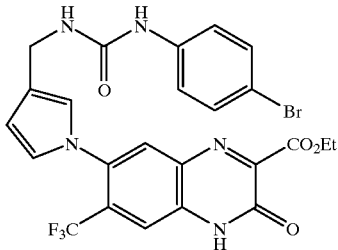

To a solution of the compound in Example 74 (200 mg, 478 μmol) in N,N-dimethylformamide (5 ml) were added 4-bromophenyl isocyanate (113 mg, 573 μmol) and triethylamine (99.9 μl, 717 μmol), and the mixture was stirred for 1 hour at 60° C. Triethylamine (666 μl, 4.78 mmol) was added to the reaction mixture after stirred further for 4 hours, solvent was distilled off. Water was added to the residue obtained, which was extracted with ethyl acetate. After dried over anhydrous sodium sulfate, solvent was distilled off. The residue obtained was purified by means of silica gel column chromatography [methylene chloride-ethanol=20:1] to obtain 154 mg of the title compound as yellow powder. Yield 56%.

$^1$H-NMR(DMSO-$d_6$,δ):1.32(3H,t,J=7.3 Hz),4.17(2H,d,J=5.4 Hz), 4.40(2H,q,J=7.3 Hz),6.24(1H,t,J=2,0 Hz),6.37(1H, d,J=5.4 Hz), 6.90(1H,s),6.91(1H,s),7.38(4H,s),7.75(1H,s), 7.90(1H,s), 8.62(1H,s),13.00–13.40(1H,br).

EXAMPLE 185

7-(3-(((4-Bromophenyl)aminocarbonylamino)methyl)pyrrole-1-yl)-3,4-dihydro-3-oxo-6-trifluoromethylquinoxaline-2-carboxylic Acid

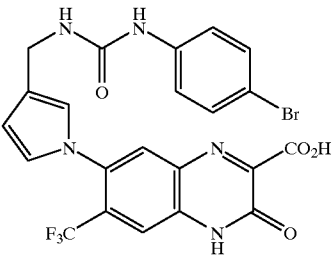

To a solution of the compound in Example 184 (152 mg, 263 μmol) in ethanol (5 ml) was added 1N aqueous solution of sodium hydroxide (789 μl, 789 μmol), and the mixture was refluxed for 1 hour. After distilled off solvent, water was added and the pH value was brought to 2 using 4N hydrochloric acid. The precipitate was collected by filtration, washed with water and chloroform in sequence and then air-dried to obtain 133 mg of the title compound as yellowish brown powder. Yield 88%.

mp 196–198° C. (decomposition).

Anal.Calcd. for $C_{22}H_{15}BrF_3N_5O_4 \cdot 4/3H_2O$: C,46.01;H, 3.10;N,12.19. Found:C,45.84;H,2.82;N,12.02.

HR-FAB–:548.0144 (–3.7 mmu).

EXAMPLE 186

Ethyl 3,4-dihydro-7-(3-(((3-ethoxycarbonylphenyl)aminocarbonylamino)methyl)pyrrole-1-yl)-3-oxo-6-trifluoromethylquinoxaline-2-carboxylate

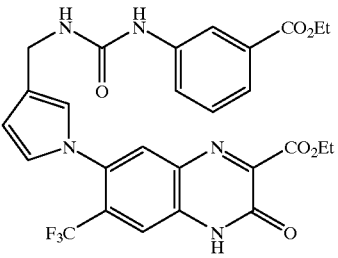

To a solution of the compound in Example 74 (200 mg, 478 μmol) in N,N-dimethylformamide (5 ml) were added ethyl 3-isocyanatobenzoate (94.9 μl, 573 μmol) and triethylamine (99.9 μl, 717 μmol), and the mixture was stirred for 3 hours at room temperature. Water was added to the reaction mixture, which was extracted with ethyl acetate. After dried over anhydrous sodium sulfate, solvent was distilled off. Methylene chloride was added to the residue obtained, the crystals were collected by filtration and washed with methylene chloride, and then air-dried. These were dissolved into N,N-dimethylformamide (5 ml), triethylamine (666 μl, 4.78 mmol) was added and the mixture was stirred for 4 hours at 80° C. The residue obtained by distilling off solvent was purified by means of silica gel column chromatography [methylene chloride-ethanol=20:1] to obtain 63.0 mg of the title compound as pale yellow powder. Yield 23%.

$^1$H-NMR(DMSO-$d_6$,δ):1.31(3H,t,J=6.9 Hz),1.32(3H,t,J=7.3 Hz), 4.19(2H,d,J=5.4 Hz),4.30(2H,q,J=6.9 Hz),4.40(2H, q,J=7.3 Hz), 6.24(1H,t,J=2.0 Hz),6.36(1H,d,J=5.4 Hz),6.91 (2H,d,J=2.0 Hz), 7.36(1H,t,J=7.8 Hz),7.49(1H,d,J=7.8 Hz), 7.61(1H,dd,J=8.3,1.0 Hz), 7.75(1H,s),7.91(1H,s),8.09(1H,t, J=2.0 Hz),8.75(1H,s), 13.22(1H,s).

HR-FAB–:570.1626 (+2.6 mmu).

EXAMPLE 187

7-(3-(((3-Carboxyphenyl)aminocarbonylamino) methyl)pyrrole-1-yl)-3,4-dihydro-3-oxo-6-trifluoromethylquinoxaline-2-carboxylic Acid

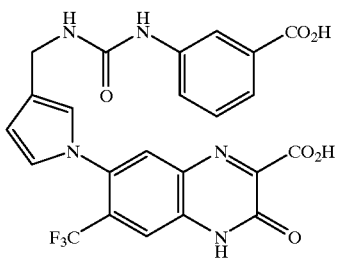

To a solution of the compound in Example 186 (60.0 mg, 105 μmol) in ethanol (2 ml) was added 1N aqueous solution of sodium hydroxide (525 μl, 525 μmol), and the mixture was refluxed for 1 hour. After distilled off solvent, water was added and the pH value was brought to 3 using 4N hydrochloric acid. The precipitate was collected by filtration, washed with water and then air-dried to obtain 50.7 mg of the title compound as yellow powder. Yield 88%.

mp 300° C.

Anal.Calcd. for $C_{23}H_{16}F_3N_5O_6 \cdot 2H_2O$: C,50.10;H,3.66;N, 12.70. Found:C,50.21;H,3.67;N,12.71.

HR-FAB–:514.1017 (+4.3,mmu).

EXAMPLE 188

3,4-Dihydro-3-oxo-7-(3-((phenylaminocarbonylamino)methyl)pyrrole-1-yl)-6-trifluoromethylquinoxaline-2-carboxylic Acid

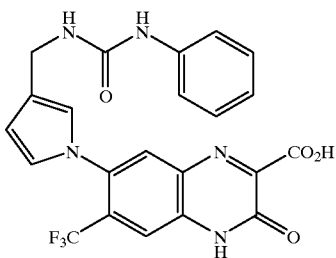

To a solution of the compound in Example 74 (200 mg, 478 μmol) in N,N-dimethylformamide (5 ml) were added phenyl isocyanate (62.3 μl, 573 μmol) and triethylamine (99.9 μl, 717 μmol), and the mixture was stirred for 1 hour at 60° C. Triethylamine (666 μl, 4.78 mmol) was added to the reaction mixture and the mixture was stirred further for 4 hours, then the solvent was distilled off. Water was added to the residue obtained, which was extracted with ethyl acetate. After dried over anhydrous sodium sulfate, solvent was distilled off. The residue obtained was purified by means of silica gel column chromatography [methylene chloride-ethanol=20:1]. After dissolved this into ethanol (5 ml), 1N aqueous solution of sodium hydroxide (1.43 ml, 1.43 mmol) was added and the mixture was refluxed for 1 hour. After distilled off solvent, water was added and the pH value was brought to 2 using 4N hydrochloric acid. The precipitate was collected by filtration, washed with water and chloroform in sequence and the air-dried to obtain 108 mg of the title compound as yellow-powder. Yield 47%.

mp >300° C.

Anal.Calcd. for $C_{22}H_{16}F_3N_5O_4 \cdot 1/2H_2O$: C,55.00;H, 3.57;N,14.58. Found:C,54.95;H,3.69;N,14.32.

HR-FAB–:470.1058 (–1.8 mmu).

EXAMPLES 189 THROUGH 205

Through the same process as in Example 188, compounds listed in following Table 11 were obtained.

TABLE 11

| Example | R | X | Example | R | X | Example | R | X |
|---|---|---|---|---|---|---|---|---|
| 189 | 2-Br-tolyl | O | 195 | 4-OMe-tolyl | O | 201 | 1-methylnaphthyl | O |
| 190 | 3-Br-tolyl | O | 196 | 4-isopropyl-tolyl | O | 202 | benzyl | O |

TABLE 11-continued

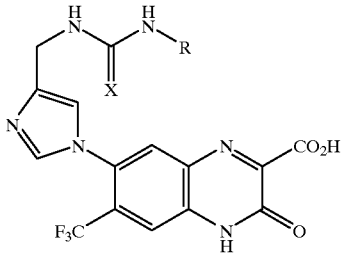

| Example | R | X | Example | R | X | Example | R | X |
|---|---|---|---|---|---|---|---|---|
| 191 | 4-Cl-C6H4- | O | 197 | 4-(CO2H-CH2)-C6H4- | O | 203 | cyclohexyl | O |
| 192 | 2-CF3-C6H4- | O | 198 | 3-(CO2H-CH2)-C6H4- | O | 204 | t-Bu | O |
| 193 | 4-CF3-C6H4- | O | 199 | 3-NO2-C6H4- | O | 205 | phenyl | S |
| 194 | 4-Me-C6H4- | O | 200 | 3,5-diCl-C6H4- | O | | | |

EXAMPLE 189 mp 165–167° C.
HR-FAB-:548.0154 (−2.7 mmu).

EXAMPLE 190 mp 207–209° C.
HR-FAB-:548.0226 (+4.5 mmu).

EXAMPLE 191 mp 198–200° C.
Anal.Calcd. for $C_{22}H_{15}ClF_3N_5O_4 \cdot 4/3H_2O$: C,49.87;H, 3.36;N,13.22. Found:C,49.94;H,3.12;N,13.01.
HR-FAB-:504.0683 (−0.3 mmu).

EXAMPLE 192 mp >300° C.
Anal.Calcd. for $C_{23}H_{15}F_6N_5O_4 \cdot 6/5H_2O$: C,49.24;H, 3.10;N,12.48. Found:C,49.18;H,3.09;N,12.38.
HR-FAB-:538.0934 (−1.6 mmu).

EXAMPLE 193 mp 194–196° C.
HR-FAB-:538.0938 (−1.2 mmu).

EXAMPLE 194 mp 183–185° C.
Anal.Calcd. for $C_{23}H_{18}F_3N_5O_4 \cdot H_2O$: C,54.87;H,4.00;N, 13.91. Found:C,54.88;H,3.92;N,13.79.
HR-FAB-:484.1262 (+2.9 mmu).

EXAMPLE 195 mp 198–200° C.
Anal.Calcd. for $C_{23}H_{18}F_3N_5O_5 \cdot 3/2H_2O$: C,52.28;H, 4.01;N,13.25. Found:C,51.97;H,3.66;N,13.07.
HR-FAB-:500.1165 (−1.6 mmu).

EXAMPLE 196 mp 235–237° C.
Anal.Calcd. for $C_{25}H_{22}F_3N_5O_4 \cdot 3/2H_2O$: C,55.55;H, 4.66;N,12.96. Found:C,55.64;H,4.33;N,12.69.
HR-FAB-:512.1569 (+2.4 mmu).

EXAMPLE 197 mp >300° C.
Anal.Calcd. for $C_{24}H_{18}F_3N_5O_6 \cdot 5/3H_2O$: C,51.52;H, 3.84;N,12.52. Found:C,51.78;H,3.74;N,12.13.
HR-FAB-:528.1124 (−0.7 mmu).

EXAMPLE 198 mp 277–279° C. (decomposition).
HR-FAB-:528.1143 (+1.2 mmu).

EXAMPLE 199 mp 189–191° C.
HR-FAB-:515.0917 (−1.0 mmu).

EXAMPLE 200 mp 195–197° C.
HR-FAB-:538.0300 (+0.4 mmu).

EXAMPLE 201 mp 223–225° C.
Anal.Calcd. for $C_{26}H_{18}F_3N_5O_4 \cdot 5/4H_2O$: C,57.41;H, 3.80;N,12.87. Found:C,57.64;H,3.69;N,12.49.
HR-FAB-:520.1235 (+0.2 mmu).

EXAMPLE 202 mp 162–164° C.
HR-FAB-:484.1227 (−0.6 mmu).

EXAMPLE 203 mp 218–220° C.
HR-FAB-:476.1571 (+2.5 mmu).

EXAMPLE 204 mp >300° C.
HR-FAB-:450.1408 (+1.9 mmu).

EXAMPLE 205 mp 198–200° C.
HR-FAB-:486.0858 (+1,1 mmu).

EXAMPLE 206

Ethyl 3,4-dihydro-7-(4-(((4-ethoxycarbonylphenyl)aminocarbonylamino)methyl)imidazole-1-yl)-3-oxo-6-trifluoromethylquinoxaline-2-carboxylate

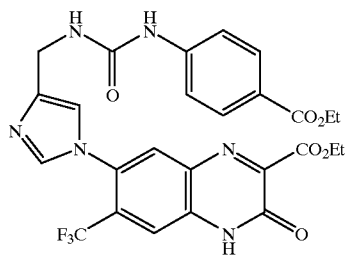

To a solution of 3-(4-(((4-ethoxycarbonylphenyl)aminocarbonylamino)methyl)imidazole-1-yl)-4-trifluoromethyl-1,2-phenylenediamine (500 mg, 1.08 mmol) in ethanol (30 ml) was added diethyl ketomalonate (260 µl, 1.70 mmol), and the mixture was refluxed for 3 hours. Then, diethyl ketomalonate (130 µl, 852 µmol) was added additionally and the mixture was refluxed further for 2 hours. The residue obtained by concentrating the reaction mixture under reduced pressure was purified by means of silica gel column chromatography [methylene chloride-methanol= 30:1] to obtain 210 mg of the title compound as yellow powder. Yield 34%.

$^1$H-NMR(DMSO-$d_6$,δ):1.30(3H,t,J=7.3 Hz),1.32(3H,t,J= 7.3 Hz), 4.20–4.32(4H,m),4.40(2H,q,J=7.3 Hz),6.61(1H,d, J=5.4 Hz), 7.30(1H,s),7.52(2H,d,J=8.8 Hz),7.78(1H,s), 7.827(1H,s), 7.833(2H,d,J=8.8 Hz),8.09(1H,s),8.26(1H,s), 13.26(1H,s).

EXAMPLE 207

7-(4-(((4-Carboxyphenyl)aminocarbonylamino)methyl)imidazole-1-yl)-3,4-dihydro-3-oxo-6-trifluoromethylquinoxaline-2-carboxylic Acid

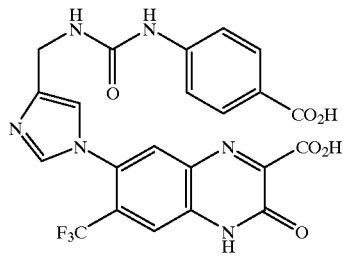

To a suspension of the compound in Example 206 (207 mg, 362 µmol) in ethanol (5 ml) was added aqueous (5 ml) solution of lithium hydroxide monohydrate (76.0 mg, 1.81 mmol), and the mixture was stirred for 2 hours at 80° C. Then, an aqueous (5 ml) solution of lithium hydroxide monohydrate (76.0 mg, 1.81 mmol) was added and the mixture was stirred further for 30 minutes at 90° C. After concentrated the reaction mixture to about half volume under reduced pressure, the pH value was brought to 2 with 1N hydrochloric acid under cooling with ice. The precipitate was collected by filtration, washed with water and then air-dried to obtain 155 mg of the title compound as yellowish brown powder. Yield 76%.

mp 255° C. (decomposition).
Anal.Calcd.for $C_{22}H_{15}F_3N_6O_6 \cdot HCl \cdot 3/5H_2O$: C,46.88;H, 3.08;N,14.91. Found:C,47.02;H,3.22; N,14.63.
HR-FAB-:515.0919 (−0.8 mmu).

EXAMPLE 208

Ethyl 3,4-dihydro-7-(4-formylimidazole-1-yl)-3-oxo-6-trifluoromethylquinoxaline-2-carboxylate

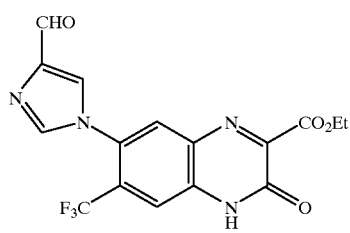

To a suspension of the compound in Example 81 (1.75 g, 4.58 mmol) in 1,4-dioxane (50 ml) was added manganese dioxide (1.99 g, 22.9 mmol), and the mixture was refluxed for 24 hours. Then, manganese dioxide (1.99 g, 22.9 mmol) was added and the mixture was refluxed further for 10 hours. After cooling, manganese dioxide was filtered off using celite and solvent was distilled off. Isopropyl ether was added to the residue obtained. The crystals were collected by filtration, washed with isopropyl ether and then air-dried to obtain 895 mg of the title compound as yellow powder. Yield 51%.

$^1$H-NMR(DMSO-$d_6$,δ):1.32(3H,t,J=7.3 Hz),4.38(2H,q,J= 7.3 Hz), 7.76(1H,s),8.11(1H,s),8.18(1H,s),8.35(1H,s),9.84 (1H,s).

EXAMPLE 209

Ethyl 7-(4-(aminomethyl)imidazole-1-yl)-3-oxo-1,2, 3,4-tetrahydro-6-trifluoromethylquinoxaline-2-carboxylate Hydrochloride

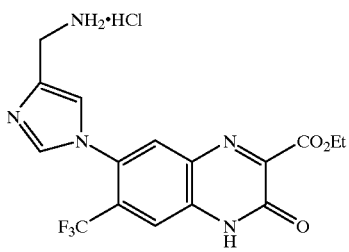

To a suspension of the compound in Example 208 (890 mg, 2.34 mmol) in ethanol (20 ml) were added hydroxylamine hydrochloride (325 mg, 4.68 mmol) and sodium acetate (384 mg, 4.68 mmol), and the mixture was refluxed for 4 hours. After cooling, the insolubles were filtered off using celite and solvent was distilled off. The residue obtained was purified by means of silica gel column chromatography [methylene chloride-ethanol=10:1] to obtain pale yellow powder. After dissolved this into ethanol (10 ml), 10% palladium-carbon (100 mg) and concentrated hydrochloric acid (0.5 ml) were added and the mixture was stirred for 2 hours at room temperature under hydrogen atmosphere (4 atm). Catalyst was filtered off using celite and solvent was distilled off. Ethyl acetate was added to the residue obtained. The crystals were collected by filtration, washed with ethyl acetate and then air-dried to obtain 556 mg of the title compound as pale yellow powder. Yield 57%.

$^1$H-NMR(DMSO-$d_6$,δ):1.18(3H,t,J=7.3 Hz),4.15(2H,q,J=7.3 Hz), 4.86(1H,s),7.21(1H,s),7.59(1H,s),7.83(1H,s), 8.20–8.40(4H,br),11.13(1H,s).

HR-FAB+:384.1255 (−2.9 mmu).

EXAMPLES 210 THROUGH 214

Using the compound in Example 209 and following the same process as in Example 188, compounds listed in following Table 12 were obtained.

TABLE 12

| Example | R | Example | R |
|---|---|---|---|
| 210 | phenyl-CH₂ | 213 | 4-OMe-phenyl-CH₂ |

TABLE 12-continued

| Example | R | Example | R |
|---|---|---|---|
| 211 | 4-Br-phenyl-CH₂ | 214 | 1-naphthyl |
| 212 | 4-Me-phenyl-CH₂ | | |

EXAMPLE 210 mp 224–226° C.

HR-FAB−:471.1030 (+0.1 mmu).

EXAMPLE 211 mp 220–222° C.

HR-FAB−:549.0111 (−2.3 mmu).

EXAMPLE 212 mp 219–221° C.

HR-FAB−:485.1172 (−1.4 mmu).

EXAMPLE 213 mp 210–212° C.

HR-FAB−:501.1155 (+2.1 mmu).

EXAMPLE 214 mp 212–214° C.

HR-FAB−:521.1146 (−3.9 mmu).

EXAMPLE 215

Ethyl 3,4-dihydro-3-oxo-7-((4-(N-phenylcarbamoyloxy)methyl)imidazole-1-yl)-6-trifluoromethylquinoxaline-2-carboxylate

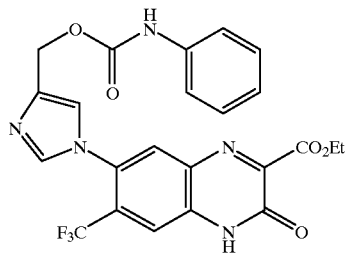

To a solution of the compound in Example 81 (200 mg, 523 μmol) in N,N-dimethylformamide (2 ml) was added phenyl isocyanate (114 μl, 1.05 mmol), and the mixture was stirred for 2 hours at 60° C. Ethanol was added to the residue obtained by distilling off solvent and, after the insolubles were filtered off, the solvent was distilled off. The residue obtained was purified by means of silica gel column chromatography [ethyl acetate-hexane (1:1 3:1)] to obtain 120 mg of the title compound as yellow powder. Yield 46%.

$^1$H-NMR(DMSO-$d_6$,δ):1.32(3H,t,J=6.8 Hz),4.40(2H,q,J=6.8 Hz), 5.08(2H,s),6.98(1H,t,J=7.3 Hz),7.27(1H,t,J=7.3 Hz),7.53(1H,s), 7.48(2H,d,J=7.3 Hz),7.78(1H,s),7.88(1H,s), 8.12(1H,s), 9.77(1H,s),13.30(1H,brs).

EXAMPLES 216 THROUGH 231

Through the same process as in Example 215, compounds listed in following Table 13 were obtained.

TABLE 13-continued

[Structure: carbamate-imidazole-quinoxaline with CO2Et, F3C, and NH-R substituents]

| Example | R |
|---|---|
| 229 | 1-naphthyl |
| 230 | benzyl (CH2-phenyl) |
| 231 | cyclohexylmethyl |

EXAMPLE 216

$^1$-NMR(DMSO-$d_6$,δ):1.33(3H,t,J=6.8 Hz),4.40(2H,q,J=6.8 Hz), 5.07(2H,s),7.12(1H,dt,J=1.5,7.8 Hz),7.37(1H,dt,J=1.5,7.8 Hz), 7.51(1H,s),7.52(1H,dd,J=1.5,7.8 Hz),7.64(1H,dd,J=1.5,7.8 Hz), 7.78(1H,s),7.88(1H,s),8.13(1H,s),9.12(1H,s),13.30(1H,brs).

EXAMPLE 217

$^1$H-NMR(DMSO-$d_6$,δ):1.32(3H,t,J=6.8 Hz),4.40(2H,q,J=6.8 Hz), 5.09(2H,s),7.18(1H,d,J=7.3 Hz),7.25(1H,t,J=7.3 Hz), 7.43(1H,d,J=7.3 Hz),7.54(1H,s),7.76(1H,s),7.78(1H,s),7.88(1H,s),10.01(1H,s),13.29(1H,brs).

EXAMPLE 218

$^1$H-NMR(DMSO-$d_6$,δ):1.32(3H,t,J=6.8 Hz),4.40(2H,q,J=6.8 Hz), 5.08(2H,s),7.46(4H,s),7.53(1H,s),7.78(1H,s),7.88(1H,s), 8.11(1H,s),9.95(1H,s),13.29(1H,brs).

EXAMPLE 219

$^1$H-NMR(DMSO-$d_6$,δ):1.33(3H,t,J=6.8 Hz),4.40(2H,q,J=6.8 Hz), 5.08(2H,s),7.11–7.26(3H,m),7.51(1H,s),7.60–7.67(1H,m), 7.79(1H,s),7.88(1H,s),8.12(1H,s),9.45(1H,s),13.30(1H,brs).

EXAMPLE 220

$^1$H-NMR(DMSO-$d_6$,δ):1.32(3H,t,J=6.8 Hz),4.40(2H,q,J=6.8 Hz), 5.08(2H,s),7.34(1H,d,J=8.8 Hz),7.50(2H,d,J=8.8 Hz),7.53(1H,s), 7.78(1H,s),7.88(1H,s),8.11(1H,s),9.94(1H,s),13.28(1H,brs).

EXAMPLE 221

$^1$H-NMR(DMSO-$d_6$,δ):1.32(3H,t,J=7.3 Hz),4.39(2H,q,J=6.8 Hz), 5.11(2H,s),7.22(1H,s),7.53(1H,s),7.55(1H,s),7.77(1H,s), 7.88(1H,s),8.09(1H,s),10.24(1H,s),13.32(1H,brs).

EXAMPLE 222

$^1$H-NMR(DMSO-$d_6$,δ):1.33(3H,t,J=7.3 Hz),4.40(2H,q,J=7.3 Hz), 5.50(2H,s),7.45(1H,t,J=7.8 Hz),7.48(1H,s),7.50(1H,d,J=7.8 Hz), 7.68(1H,t,J=7.8 Hz),7.72(1H,d,J=7.8 Hz), 7.78(1H,s),7.87(1H,s), 8.11(1H,s),9.22(1H,s),13.30(1H,brs).

EXAMPLE 223

$^1$H-NMR(DMSO-$d_6$,δ):1.32(3H,t,J=6.8 Hz),4.40(2H,t,q,J=6.8 Hz), 5.12(2H,s),7.54(1H,s),7.65(2H,d,J=8.8 Hz),7.69(2H,d,J=8.8 Hz), 7.78(1H,s),7.88(1H,s),8.10(1H,s),10.23(1H,s),13.30(1H,brs).

EXAMPLE 224

$^1$H-NMR(DMSO-$d_6$,δ):1.32(3H,t,J=7.3 Hz),2.23($_3$H,s), 4.40(2H,q,J=7.3 Hz),5.06(2H,s),7.07(2H,d,J=8.3 Hz), 7.35(2H,d,J=8.3 Hz),7.51(1H,s),7.78(1H,s),7.87(1H,s), 8.11(1H,s),9.65(1H,s),13.28(1H,brs).

EXAMPLE 225

$^1$H-NMR(DMSO-$d_6$,δ):1.32(3H,t,J=7.3 Hz),4.39(2H,q,J=7.3 Hz), 5.05(2H,s),6.86(2H,d,J=8.8 Hz),7.37(2H,d,J=8.8 Hz),7.50(1H,s), 7.76(1H,s),7.86(1H,s),8.07(1H,s),9.57(1H,s),13.27(1H,brs).

EXAMPLE 226

$^1$H-NMR(DMSO-$d_6$,δ):1.17(3H,t,J=7.3 Hz),1.32(3H,t,J=7.3 Hz), 3.57(2H,s),4.06(2H,q,J=7.3 Hz),4.40(2H,q,J=7.3 Hz), 5.07(2H,s), 7.16(2H,d,J=8.3 Hz),7.41(2H,d,J=8.3 Hz), 7.52(1H,s),7.78(1H,s), 7.87(1H,s),8.11(1H,s),9.76(1H,s),13.30(1H,brs).

EXAMPLE 227

$^1$H-NMR(DMSO-$d_6$,δ):1.32(3H,t,J=6.8 Hz),3.61(3H,s), 3.62(2H,s), 4.40(2H,q,J=6.8 Hz),5.08(2H,s),6.89(1H,d,J=7.3 Hz), 7.22(1H,t,J=7.3 Hz),7.36(1H,d,J=7.3 Hz),7.41(1H,s),7.52(1H,s), 7.78(1H,s),7.87(1H,s),8.12(1H,s),9.79(1H,s),13.29(1H,brs).

EXAMPLE 228

$^1$H-NMR(DMSO-$d_6$,δ):1.31(3H,t,J=6.8 Hz),1.32(3H,t,J=7.3 Hz), 4.31(2H,q,J=6.8 Hz),4.40(2H,q,J=7.3 Hz),5.10(2H,s), 7.43(1H,t,J=7.8 Hz),7.54(1H,s),7.59(1H,d,J=7.8 Hz), 7.69(1H,d,J=7.8 Hz),7.78(1H,s),7.88(1H,s),8.12(1H,s), 8.19(1H,s),10.03(1H,s),13.30(1H,brs).

EXAMPLE 229

$^1$H-NMR(DMSO-$d_6$,δ):1.33(3H,t,J=6.8 Hz),4.40(2H,q,J=6.8 Hz), 5.12(2H,s),7.46–7.55(4H,m),7.59–7.66(1H,m), 7.74(1H,d,J=7.8 Hz), 7.79(1H,s),7.88–7.98(1H,m),7.90(1H,s),8.05–8.10(1H,m), 8.13(1H,s),9.68(1H,s),13.30(1H,brs).

EXAMPLE 230

$^1$H-NMR(DMSO-$d_6$,δ):1.32(3H,t,J=6.8 Hz),4.19(1H,s), 4.21(1H,s), 4.40(2H,q,J=6.8 Hz),4.96(2H,s),7.23(2H,d,J=7.3 Hz),7.26(1H,s), 7.31(2H,t,J=7.3 Hz),7.43(1H,s),7.77(1H,s),7.80(1H,t,J=7.3 Hz), 7.84(1H,s),8.10(1H,s),13.26(1H,s).

EXAMPLE 231

$^1$H-NMR(DMSO-$d_6$,δ):1.03–1.26(4H,m),1.32(3H,t,J=7.3 Hz), 1.49–1.79(4H,m),4.38(2H,q,J=7.3 Hz),4.90(2H,s), 7.17(1H,d,J=8.3 Hz),7.41(1H,s),7.75(1H,s),7.82(1H,s), 8.02(1H,s).

EXAMPLE 232

Ethyl 3,4-dihydro-3-oxo-7-((4-(N-(4-pyridyl)-carbamoyloxy)methyl)imidazole-1-yl)-6-trifluoromethylquinoxaline-2-carboxylate

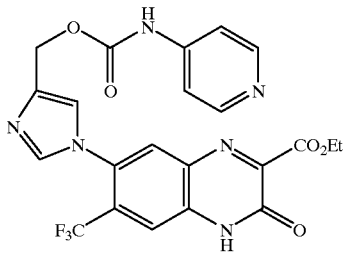

To a solution of isonicotinic acid (129 mg, 1.05 mmol) in benzene (5 ml) were added diphenylphosphoryl azide (226 µl, 1.05 mmol) and triethylamine (146 µl, 1.05 mmol), and the mixture was refluxed for 3 hours. To this was added a solution of the compound in Example 81 (200 mg, 523 µmol) in N,N-dimethylformamide (1 ml), and the mixture was refluxed further for 2 hours. Ethyl acetate was added to the reaction mixture, which was washed with brine, then dried over anhydrous magnesium sulfate, and solvent was distilled off. The residue obtained was purified by means of silica gel column chromatography [methylene chloride-ethanol (30:1 7:1)] to obtain 87.0 mg of the title compound as yellow powder. Yield 33%.

HR-FAB-:510.1154 (+1.9 mmu).

EXAMPLE 233

Ethyl 3,4-dihydro-3-oxo-7-((4-(N-(3-thienyl)carbamoyloxy)methyl)imidazole-1-yl)-6-trifluoromethylquinoxaline-2-carboxylate

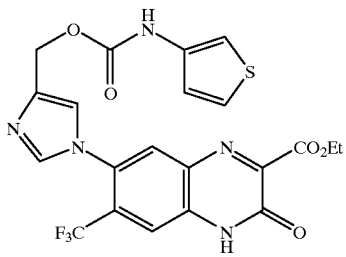

Using the compound in Example 81 (200 mg, 523 µmol) and thiophene-3-carboxylic acid (135 mg, 1.05 mmol) and following the same process as in Example 232, 204 mg of the title compound were obtained as orange powder. Yield 77%.

HR-FAB-:506.0739 (-0.7 mmu).

EXAMPLE 234

Ethyl 3,4-dihydro-3-oxo-7-((4-(N-(benzofuran-2-yl)-carbamoyloxy)methyl)imidazole-1-yl)-6-trifluoromethylquinoxaline-2-carboxylate

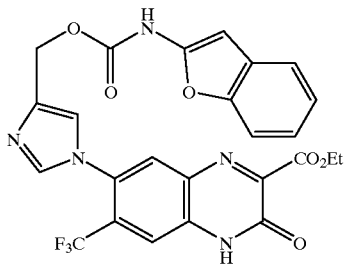

To a solution of the compound in Example 81 (200 mg, 523 µmol) and benzofuran-2-carboxylic acid (102 mg, 628 µmol) in N,N-dimethylformamide (5 ml) were added diphenylphosphoryl azide (226 µl, 1.05 mmol) and triethylamine (146 µl, 1.05 mmol), and the mixture was stirred for 6 hours at 60° C. Ethyl acetate was added to the reaction mixture, which was washed with brine, then dried over anhydrous magnesium sulfate, and solvent was distilled off. The residue obtained was purified by means of silica gel column chromatography [ethyl acetate-hexane (1:1) ethyl acetate] to obtain 114 mg of the title compound as yellow powder. Yield 40%.

HR-FAB-:540.1104 (-2.7 mmu).

EXAMPLE 235

3,4-Dihydro-3-oxo-7-((4-(N-phenylcarbamoyloxy)methyl)imidazole-1-yl)-6-trifluoromethylquinoxaline-2-carboxylic Acid

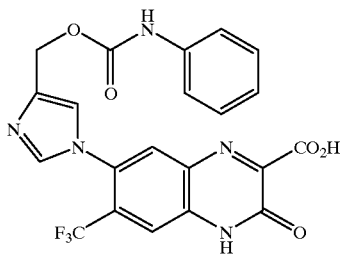

To a solution of the compound in Example 215 (100 mg, 199 µmol) in ethanol (4 ml) were added 1N aqueous solution of lithium hydroxide (697 µl, 697 µmol) and water (4 ml), and the mixture was stirred for 1.5 hours at 50° C. After cooling, ice water was added, the insolubles were filtered off, and the filtrate was made acidic using 3N hydrochloric acid. The precipitate was collected by filtration, washed with water and then air-dried to obtain 63.0 mg of the title compound as yellow powder. Yield 64%.

mp 193–195° C. (decomposition).

Anal.Calcd. for $C_{21}H_{14}F_3N_5O_5 \cdot 6/5H_2O$: C,50.95;H, 3.34;N,14.15. Found:C,50.95;H,3.06;N,13.95.

HR-FAB-:472.0885 (+1.6 mmu).

EXAMPLES 236 THROUGH 252

Through the same process as in Example 235, compounds listed in following Table 14 were obtained.

TABLE 14

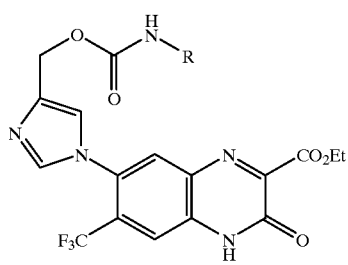

| Example | R |
|---|---|
| 236 | 2-bromophenyl-methyl |
| 237 | 3-bromophenyl-methyl |
| 238 | 4-bromophenyl-methyl |
| 239 | 2-fluorophenyl-methyl |
| 240 | 4-chlorophenyl-methyl |
| 241 | 3,5-dichlorophenyl-methyl |
| 242 | 2-trifluoromethylphenyl-methyl |
| 243 | 4-trifluoromethylphenyl-methyl |
| 244 | 4-methylphenyl-methyl |
| 245 | 4-methoxyphenyl-methyl |

TABLE 14-continued

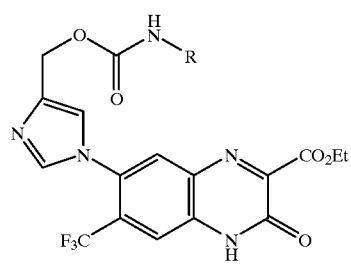

| Example | R |
|---|---|
| 246 | 4-(carboxymethyl)phenyl-methyl |
| 247 | 3-(carboxymethyl)phenyl-methyl |
| 248 | 1-naphthyl-methyl |
| 249 | phenyl-ethyl |
| 250 | cyclohexyl-methyl |
| 251 | 3-thienyl-methyl |
| 252 | 2-benzofuranyl-methyl |

EXAMPLE 236 mp 152–154° C.

HR-FAB−:549.9987 (+1.3 mmu).

EXAMPLE 237 mp 219–221° C.

Anal.Calcd. for $C_{21}H_{13}BrF_3N_5O_5 \cdot 1/2H_2O$: C,44.95;H, 2.51;N,12.47. Found:C44.80;H,2.28;N,12.21.

HR-FAB−:549.9981 (+0.7 mmu).

EXAMPLE 238 mp 218–220° C.

Anal.Calcd. for $C_{21}H_3BrF_3N_5O_5 \cdot 1/2H_2O$: C,44.94;H,2.51;N,12.47. Found:C,45.00;H,2.29;N,12.23.

HR-FAB–:549.9969 (–0.4 mmu).

EXAMPLE 239 mp 184–186° C.

Anal.Calcd. for $C_{21}H_{13}F_4N_5O_5 \cdot 1/2H_2O$: C,50.41;H,2.82;N,13.99. Found:C,50.11;H,2.72;N,13.67.

HR-FAB–:490.0788 (+1.4 mmu).

EXAMPLE 240 mp 204–206° C.

HR-FAB–:506.0497 (+1.8 mmu).

EXAMPLE 241 mp 204–206° C.

Anal.Calcd. for $C_{21}H_{12}Cl_2F_3N_5O_5 \cdot 6/5H_2O$: C,44.73;H,2.57;N,12.42. Found:C,44.91;H,2.31;N,12.09.

HR-FAB–:540.0046 (–4.4 mmu).

EXAMPLE 242 mp 166–168° C.

Anal.Calcd. for $C_{22}H_{13}F_6N_5O_5 \cdot H_2O$: C,47.24;H,2.70;N,12.52. Found:C,47.36: H,2.51;N,12.21.

HR-FAB–:540.0732 (–1.1 mmu).

EXAMPLE 243 mp 194–196° C.

HR-FAB–:540.0743 (+0.0 mmu).

EXAMPLE 244 mp 179–181° C.

HR-FAB–:486.1013 (–1.2 mmu).

EXAMPLE 245 mp 210–212° C.

Anal.Calcd. for $C_{22}H_{16}F_3N_5O_6 \cdot 1/2H_2O$: C,51.57;H,3.34;N,13.67. Found:C,51.71;H,3.13;N,13.43.

HR-FAB–:502.0992 (+1.7 mmu).

EXAMPLE 246 mp 210–212° C.

Anal.Calcd. for $C_{23}H_{16}F_3N_5O_7 \cdot 3/2H_2O$: C,49.47;H,3.34;N,12.54. Found:C,49.67;H,3.10;N,12.37.

HR-FAB–:530.0942 (+1.8 mmu).

EXAMPLE 247 mp 196–198° C.

HR-FAB–:530.0925 (+0.2 mmu).

EXAMPLE 248 mp 208–210° C.

Anal.Calcd. for $C_{25}H_{16}F_3N_5O_5 \cdot 2.8H_2O$: C,52832;H3.79;N,12.20. Found:C,52.09;H,3.40;N,12.01.

HR-FAB–:552.1044 (+1.9 mmu).

EXAMPLE 249 mp 165–167° C.

HR-FAB–:486.1043 (+1.8 mmu).

EXAMPLE 250 mp 225–227° C.

Anal.Calcd. for $C_{21}H_{20}F_3N_5O_5 \cdot 7/10H_2O$: C,51.2 6;H,4.38;N,14.23. Found:C,51.13;H,4.16;N,14.04.

HR-FAB–:478.1336 (–0.2 mmu).

EXAMPLE 251 mp 267–269° C. (decomposition).

Anal.Calcd. for $C_{19}H_{12}F_3N_5O_5S \cdot 2.3H_2O$: C,43.82;H,3.21;N,13.44. Found:C,43.96;H,2.89;N,13.07.

HR-FAB–:478.0433 (+0.0 mmu).

EXAMPLE 252 mp 245–247° C. (decomposition).

HR-FAB–:512.0789 (–2.9 mmu).

EXAMPLE 253

7-((4-(N-(3-Carboxyphenyl)carbamoyloxy)methyl)imidazole-1-yl)-3,4-dihydro-3-oxo-6-trifluoromethylquinoxaline-2-carboxylic Acid

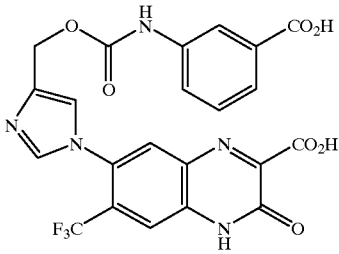

To a solution of the compound in Example 228 (180 mg, 314 μmol) in acetic acid (5 ml) was added concentrated hydrochloric acid (1 ml), and the mixture was stirred for 2 hours at room temperature. After allowed to stand statically overnight, ice water was added, the precipitate was collected by filtration and washed with water. After dissolved these into 1N aqueous solution of lithium hydroxide, the insolubles were filtered off and the pH value was brought to 4 using 3N hydrochloric acid. The precipitate was collected by filtration, washed with water and then air-dried to obtain 25.0 mg of the title compound as brown powder. Yield 15%.

mp 215–217° C. (decomposition).

HR-FAB–:516.0778 (+1.1 mmu).

EXAMPLE 254

3,4-Dihydro-3-oxo-7-((4-(N-(4-pyridyl)carbamoyloxy)methyl)imidazole-1-yl)-6-trifluoromethylquinoxaline-2-carboxylic Acid

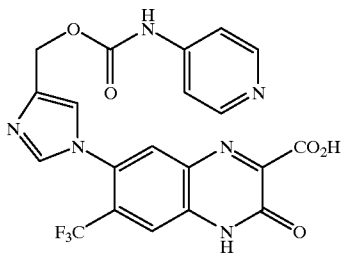

To a solution of the compound in Example 232 (75.0 mg, 149 μmol) in ethanol (2 ml) were added 1N aqueous solution of lithium hydroxide (522 μl, 522 μmol) and water (2 ml), and the mixture was stirred for 1.5 hours at 50° C. After cooling, ice water was added, the insolubles were filtered off, and the pH value was brought to 4 using 3N hydrochloric acid. This was concentrated under reduced pressure, purified with synthetic adsorbent Sepabeads® SP850 [water→water-acetonitrile (5:1)] and recrystallized from water to obtain 5.0 mg of the title compound as pale yellow powder. Yield 7%.

mp 254–256° C. (decomposition).
HR-FAB–:473.0844 (+2.3 mmu).

EXAMPLE 255

3,4-Dihydro-3-oxo-7-((4-(N-(4-quinolyl)carbamoyloxy)methyl)imidazole-1-yl)-6-trifluoromethylquinoxaline-2-carboxylic Acid

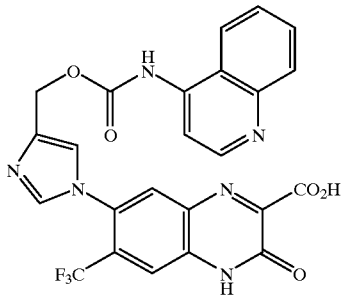

To a solution of quinoline-4-carboxylic acid (182 mg, 1.05 mmol) in benzene (5 ml) were added diphenylphosphoryl azide (226 μl, 1.05 mmol) and triethylamine (146 μl, 1.05 mmol), and the mixture was refluxed for 3 hours. To this was added a solution of the compound in Example 81 (200 mg, 523 μmol) in N,N-dimethylformamide (1 ml), and the mixture was refluxed further for 2 hours. Ethyl acetate was added to the reaction mixture, which was washed with brine, then dried over anhydrous magnesium sulfate, and solvent was distilled off. The residue obtained was purified by means of silica gel column chromatography [methylene chloride-ethanol [30:1 7:1]] to obtain 188 mg of ethyl 3,4-dihydro-3-oxo-7-((4-(N-(4-quinolyl)carbamoyloxy)methyl)-imidazole-1-yl)-6-trifluoromethylquinoxaline-2-carboxylate as yellow powder. Yield 65%.

To a solution of the ethyl ester (150 mg, 272 μmol) obtained in ethanol (3 ml) were added 1N aqueous solution of lithium hydroxide (950 μl, 950 μmol) and water (3 ml), and the mixture was stirred for 1.5 hours at 50° C. After cooling, ice water was added and the insolubles were filtered off. After dissolved these by adding 3N hydrochloric acid, the insolubles were filtered off. The filtrate was purified with synthetic adsorbent Sepabeads® SP850 [water-acetonitrile (20:1→5:1)] and recrystallized from water to obtain 10.3 mg of the title compound as light brown powder. Yield 7%.

mp 239–241° C. (decomposition).

HR-FAB–:523.0975 (–0.2 mmu).

EXAMPLE 256

7-((4-(N-(4-Carboxyphenyl)carbamoyloxy)methyl)imidazole-1-yl)-3,4-dihydro-4-ethyl-3-oxo-6-trifluoromethylquinoxaline-2-carboxylic Acid

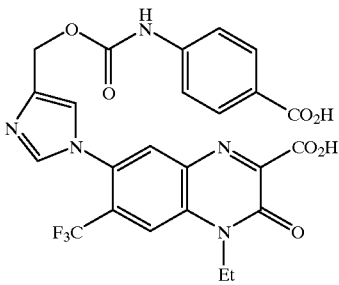

To a solution of the compound in Example 82 (560 mg, 976 μmol) in N,N-dimethylformamide (10 ml) were added potassium carbonate (540 mg, 3.90 mmol) and iodoethane (625 μl, 7.81 mmol), and the mixture was stirred for 2 hours at 80° C. Then, iodoethane (625 μl, 7.81 mmol) was added and the mixture was stirred further for 16 hours. After distilled off solvent, ethyl acetate was added and the solution was made acidic by further adding 3N hydrochloric acid. The organic layer was separated, washed with brine, then dried over anhydrous magnesium sulfate and solvent was distilled off. The residue obtained was purified by means of silica gel column chromatography [ethyl acetate-hexane (1:3→5:1)] to obtain 102 mg of 4-ethylquinoxaline ester as yellow powder. After dissolved this into ethanol (2 ml), 1N aqueous solution of lithium hydroxide (593 μl, 593 umol) and water (2 ml) were added in sequence and the mixture was stirred for 1.5 hours at 50° C. After cooling, ice water was added and the insolubles were filtered off. After the pH value was brought to 4 by adding 3N hydrochloric acid, the crystals were collected by filtration, washed with water and with ethyl acetate in sequence and then air-dried to obtain 19.0 mg of the title compound as light orange powder. Yield 20%.

mp 194–196° C.

HR-FAB–:544.1055 (–2.5 mmu).

EXAMPLE 257

Ethyl 3-ethoxy-7-(4-((N-(4-ethoxycarbonylphenyl)carbamoyloxy)methyl)imidazolyl)-6-nitroquinoxaline-2-carboxylate

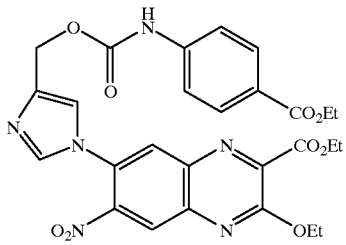

To a solution of the compound in Example 84 (329 mg, 849 μmol) in benzene (30 ml) was added ethyl 4-isocyanatobenzoate (325 mg, 1.70 mmol), and the mixture was refluxed for 2 hours After cooling, the residue obtained by distilling off solvent was submitted to silica gel column chromatography [hexane-ethyl acetate=1:1] to obtain 488 mg of the title compound as yellow amorphous material. Yield 99%.

$^1$H-NMR(CDCl$_3$,δ):1.38(3H,t,J=6.9 Hz),1.46(3H,t,J=7.3 Hz), 1.53(3H,t,J=6.9 Hz),4.35(2H,q,J=6.9 Hz),4.55(2H,q,J=7.3 Hz), 4.66(2H,q,J=6.9 Hz),5.25(2H,s),7.17(1H,s),7.25(1H,d,J=1.0 Hz), 7.47(2H,d,J=8.8 Hz),7.71(1H,d,J=1.5 Hz), 7.99(2H,d,J=8.8 Hz), 8.15(1H,s),8.45(1H,s).

EXAMPLES 258 THROUGH 262

Through the same process as in Example 257, compounds listed in following Table 15 were obtained.

TABLE 15

| Example | R |
|---|---|
| 258 | 3-cyanophenyl |
| 259 | 2,5-difluoro-4-methylphenyl |
| 260 | 3,5-bis(trifluoromethyl)phenyl |

TABLE 15-continued

| Example | R |
|---|---|
| 261 | 1-naphthyl |
| 262 | cyclohexylmethyl |

EXAMPLE 258

$^1$H-NMR(CDCl$_3$,δ):1.46(3H,t,J=7.3 Hz),1.53(3H,t,J=7.3 Hz), 4.55(2H,q,J=7.3 Hz),4.67(2H,q,J=7.3 Hz),5.25(2H,s), 7.11(1H,s), 7.26(1H,d,J=1.5 Hz),7.33–7.42(2H,m),7.57(1H,dt,J=8.3,1.0 Hz), 7.71(1H,d,J=1.5 Hz),7.84(1H,s),8.16(1H,s),8.45(1H,s).

EXAMPLE 259

$^1$H-NMR(CDCl$_3$,δ):1.47(3H,t,J=7.3 Hz),1.53(3H,t,J=6.9 Hz), 4.55(2H,q,J=7.3 Hz),4.67(2H,q,J=6.9 Hz),5.25(2H,s), 6.82–6.89(3H,m),7.71(1H,d,J=1.5 Hz),8.04–8.07(1H,br), 8.16(1H,s), 8.45(1H,s).

EXAMPLE 260

$^1$H-NMR(CDCl$_3$,δ):1.46(3H,t,J=7.3 Hz),1.53(3H,t,J=6.9 Hz), 4.55(2H,q,J=7.3 Hz),4.67(2H,q,J=6.9 Hz),5.27(2H,s), 7.55(1H,s), 7.71(1H,d,J=1.5 Hz),7.91(2H,s),8.16(1H,s),8.46(1H,s).

EXAMPLE 261

$^1$H-NMR(CDCl$_3$,δ):1.47(3H,t,J=7.3 Hz),1.53(3H,t,J=7.3 Hz), 4.55(2H,q,J=7.3 Hz),4.66(2H,q,J=7.3 Hz),5.30(2H,d,J=1.5 Hz), 7.13(1H,s),7.45–7.52(3H,m),7.53(1H,dd,J=6.9, 1.5 Hz), 7.66(1H,d,J=8.3 Hz),7.72–7.90(3H,m),8.16(1H,s), 8.45(1H,s).

EXAMPLE 262

$^1$H-NMR(CDCl$_3$,δ):1.08–1.25(2H,m),1.30–1.44(2H,m), 1.47(3H,t,J=7.3 Hz),1.53(3H,t,J=6.9 Hz),1.55–1.60(2H,m), 1.67–1.72(2H,m),1.91–1.95(2H,m),3.48–3.52(1H,m), 4.55(2H,q,J=7.3 Hz),4.66(2H,q,J=7.3 Hz),5.10(2H,s), 7.18(1H,d,J=1.0 Hz),7.68(1H,d,J=1.5 Hz),8.14(1H,s),8.43(1H,s).

EXAMPLE 263

Ethyl 7-(4-((N-((4-bromophenyl)methyl)carbamoyloxy)methyl)imidazolyl)-3-ethoxy-6-nitroquinoxaline-2-carboxylate

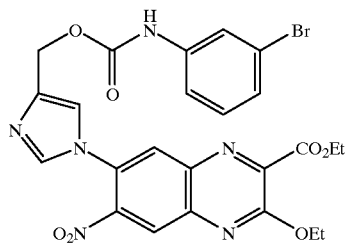

To a solution of the compound in Example 84 (150 mg, 387 μmol) and 4-bromophenylacetic acid (166 mg, 774 μmol) in benzene (12 ml) were added diphenylphosphoryl azide (167 μl, 774 μmol) and triethylamine (108 μl, 774 μmol), and the mixture was refluxed for 3 hours. After cooling, the residue obtained by distilling off solvent was submitted to silica gel column chromatography [hexane-ethyl acetate=2:1] to obtain 121 mg of the title compound as yellow amorphous material. Yield 52%.

$^1$H-NMR(CDCl$_3$,δ):1.47(3H,t,J=7.3 Hz),1.53(3H,t,J=7.3 Hz), 4.34(2H,d,J=6.4 Hz),4.55(2H,q,J=7.3 Hz),4.67(2H,q, J=7.3 Hz), 5.16(2H,s),7.17(2H,d,J=8.3 Hz),7.19(1H,s),7.45 (2H,d,J=8.3 Hz), 7.68(1H,s),8.14(1H,s),8.44(1H,s).

EXAMPLES 264 THROUGH 277

Through the same process as in Example 263, compounds listed in following Table 16 were obtained.

TABLE 16

| Example | R |
|---|---|
| 264 | 3-Br-benzyl-CH2 |
| 265 | 2-Br-benzyl-CH2 |
| 266 | phenethyl-CH2 |
| 267 | 4-NMe2-3-Me-phenyl |
| 268 | 2,4-diF-3-Me-phenyl |
| 269 | 2,4-bis(CF3)-3-Me-phenyl |
| 270 | 6-Me-naphthalen-2-yl |
| 271 | 5-Me-pyridin-3-yl |
| 272 | 5-Me-pyrazin-2-yl |
| 273 | 4-Me-quinolin-2-yl |
| 274 | 5-F-2-Me-1H-indol-3-yl |
| 275 | 2-Me-thiophen-5-yl |
| 276 | 3-Me-thiophen-5-yl |

TABLE 16-continued

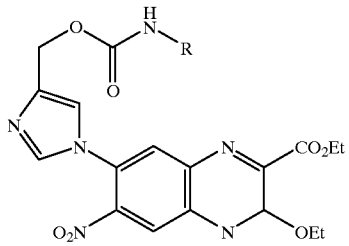

| Example | R |
|---|---|
| 277 | 2-methylbenzofuran |

EXAMPLE 264

$^1$H-NMR(CDCl$_3$,δ):1.47(3H,t,J=7.3 Hz),1.53(3H,t,J=7.3 Hz), 4.37(2H,d,J=5.9 Hz),4.55(2H,q,J=7.3 Hz),4.67(2H,q,J=7.3 Hz), 5.17(2H,s),7.18–7.24(3H,m),7.38–7.44(2H,m), 7.68(1H,d,J=1.0 Hz),8.15(1H,s),8.44(1H,s).

EXAMPLE 265

$^1$H-NMR(CDCl$_3$,δ):1.47(3H,t,J=7.3 Hz),1.53(3H,t,J=6.9 Hz), 4.46(2H.,d,J=6.4 Hz),4.55(2H,q,J=7.3 Hz),4.67(2H,q,J=6.9 Hz), 5.15(2H,s),5.30–5.40(1H,br),7.12–7.33(2H,m), 7.41(1H,d,J=6.9 Hz),7.54(1H,d,J=7.8 Hz),7.68(1H,s),8.14(1H,s), 8.44(1H,s).

EXAMPLE 266

$^1$H-NMR(CDCl$_3$,δ):1.47(3H,t,J=7.3 Hz),1.53(3H,t,J=6.9 Hz), 2.82(2H,t,J=6.9 Hz),3.47(2H,q,J=6.9 Hz),4.55(2H,q,J=7.3 Hz), 4.66(2H,q,J=6.9 Hz),4.85(1H,brs),5.12(2H,s), 7.17–7.22(3H,m), 7.27–7.31(2H,m),7.67(1H,d,J=1.5 Hz), 8.14(1H,s),8.43(1H,s).

EXAMPLE 267

$^1$H-NMR(CDCl$_3$,δ):1.47(3H,t,J=7.3 Hz),1.53(3H,t,J=6.9 Hz), 2.90(6H,s),4.55(2H,q,J=7.3 Hz),4.66(2H,q,J=6.9 Hz), 5.21(2H,s), 6.57(1H,brs),6.70(2H,d,J=8.8 Hz),7.69(1H,d,J=1.0 Hz), 8.15(1H,s),8.44(1H,s).

EXAMPLE 268

$^1$H-NMR(CDCl$_3$,δ):1.47(3H,t,J=7.3 Hz),1.53(3H,t,J=6.9 Hz), 4.55(2H,q,J=7.3 Hz),4.67(2H,q,J=6.9 Hz),5.26(2H,s), 6.63–6.69(1H,m),6.97–7.06(2H,m),7.26(1H,d,J=2.0 Hz), 7.71(1H,d,J=1.0 Hz),7.90–8.10(1H,br),8.16(1H,s),8.45(1H,s).

EXAMPLE 269

$^1$H-NMR(CDCl$_3$,δ):1.47(3H,t,J=7.3 Hz),1.53(3H,t,J=6.9 Hz), 4.55(2H,q,J=7.3 Hz),4.67(2H,q,J=6.9 Hz),5.28(2H,s), 7.21(2H,s), 7.27(1H,d,J=1.5 Hz),7.72(1H,d,J=1.5 Hz),7.80(1H,d,J=8.8 Hz), 7.83(1H,s),8.17(1H,s),8.45(1H,d,J=9.3 Hz),8.46(1H,s).

EXAMPLE 270

$^1$H-NMR(CDCl$_3$,δ):1.46(3H,t,J=7.3 Hz),1.52(3H,t,J=6.9 Hz), 4.54(2H,q,J=7.3 Hz),4.66(2H,q,J=6.9 Hz),5.28(2H,s), 7.01(1H,s), 7.27(1H,d,J=1.0 Hz),7.35–7.46(3H,m),7.71(1H,d,J=1.0 Hz), 7.75(1H,d,J=7.3 Hz),7.76(1H,d,J=8.8 Hz),7.99(1H,s),8.15(1H,s), 8.44(1H,s).

EXAMPLE 271

$^1$H-NMR(CDCl$_3$,δ):1.46(3H,t,J=7.3 Hz),1.52(3H,t,J=6.9 Hz), 4.54(2H,q,J=7.3 Hz),4.66(2H,q,J=6.9 Hz),5.25(2H,s), 7.25(1H,s), 7.63(1H,brs),7.12–7.33(2H,m),7.74(1H,d,J=1.5 Hz), 8.03(1H,d,J=8.3 Hz),8.15(1H,s),8.29(1H,dd,J=4.9,1.5 Hz), 8.44(1H,s),8.55(1H,d,J=2.4 Hz).

EXAMPLE 272

$^1$H-NMR(CDCl$_3$,δ):1.47(3H,t,J=7.3 Hz),1.53(3H,t,J=7.3 Hz), 4.55(2H,q,J=7.3 Hz),4.66(2H,q,J=7.3 Hz),5.30(2H,s), 7.28(1H,s), 7.73(1H,s),8.12(1H,s),8.17(1H,s),8.23(1H,s), 8.30(1H,d,J=2.4 Hz),8.46(1H,s),9.36(1H,s).

EXAMPLE 273

$^1$H-NMR(CDCl$_3$,δ):1.47(3H,t,J=7.3 Hz),1.53(3H,t,J=7.3 Hz), 4.55(2H,q,J=7.3 Hz),4.66(2H,q,J=7.3 Hz),5.33(2H,s), 7.30(1H,s), 7.56(1H,d,J=8.3 Hz),7.70(1H,s),7.72(1H,d,J=5.4 Hz),7.74(1H,s), 7.83(1H,d,J=8.3 Hz),8.10(1H,s),8.17(1H,s),8.14(1H,d,J=4.9 Hz), 8.47(1H,s),8.83(1H,d,J=5.4 Hz).

EXAMPLE 274

$^1$H-NMR(CDCl$_3$,δ):1.45(3H,t,J=7.3 Hz),1.51(3H,t,J=7.3 Hz), 4.53(2H,q,J=7.3 Hz),4.62(2H,q,J=7.3 Hz),5.25(2H,s), 5.75(1H,s), 6.74(1H,td,J=8.8,2.5 Hz),7.00(1H,dd,J=9.8,2.5 Hz), 7.11(1H,dd,J=8.8,4.4 Hz),7.25(1H,d,J=1.0 Hz),7.73(1H,s), 8.11(1H,s),8.40(1H,s),8,75(1H,s),9.82(1H,s).

EXAMPLE 275

$^1$H-NMR(CDCl$_3$,δ):1.46(3H,t,J=6.9 Hz),1.53(3H,t,J=6.9 Hz), 4.55(2H,q,J=6.9 Hz),4.66(2H,q,J=6.9 Hz),5.25(2H,s), 6.60(1H,dd,J=3.9,1.5 Hz),6.80–6.86(2H,m),7.25(1H,s),7.52(1H,s), 7.69(1H,d,J=1.5 Hz),8.15(1H,s),8.44(1H,s).

EXAMPLE 276

$^1$H-NMR(CDCl$_3$,δ):1.47(3H,t,J=7.3 Hz),1.53(3H,t,J=6.9 Hz), 4.55(2H,q,J=7.3 Hz),4.66(2H,q,J=6.9 Hz),5.23(2H,s), 6.94(1H,dd,J=4.9,1.0 Hz),7.07(1H,s),7.20–7.24(3H,m), 7.69(1H,d,J=1.0 Hz),8.15(1H,s),8.44(1H,s).

EXAMPLE 277

$^1$H-NMR(CDCl$_3$,δ):1.47(3H,t,J=7.3 Hz),1.53(3H,t,J=7.3 Hz), 4.54(2H,q,J=7.3 Hz),4.66(2H,q,J=7.3 Hz),5.29(2H,s), 6.52(1H,brs), 7.14–7.19(2H,m),7.32(1H,d,J=7.3 Hz),7.36(1H,s), 7.44(1H,d,J=7.3 Hz),7.71(1H,s),8.15(1H,s),8.45(1H,s).

EXAMPLE 278

3,4-Dihydro-7-(4-((N-(4-ethoxycarbonylphenyl)carbamoyloxy)methyl)imidazolyl)-6-nitro-3-oxoquinoxaline-2-carboxylic Acid

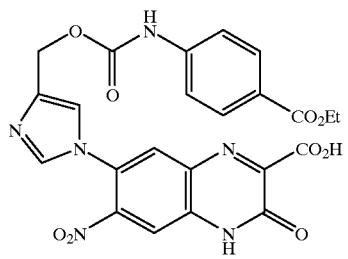

To a solution of the compound in Example 257 (488 mg, 844 μmol) in acetic acid (10 ml) was added hydrochloric acid (2.5 ml), and the mixture was stirred for 24 hours at room temperature. Water was added to the reaction mixture. The precipitate was collected by filtration, washed with water and then air-dried to obtain 372 mg of the title compound as yellowish brown powder. Yield 80%.

mp 207–209° C. (decomposition).

Anal.Calcd. for $C_{23}H_{18}N_6O_9 \cdot 3/2H_2O$: C,50.28;H,3.85;N,15.30. Found:C,50.02;H,3.62;N,14.94.

HR-FAB-:521.1057 (-0.8 mmu).

EXAMPLE 279 THROUGH 288

Through the same process as in Example 278, compounds listed in following Table 17 were obtained.

TABLE 17

| Example | R |
|---|---|
| 279 | 3-cyanophenyl (m-CN-C6H4) |
| 280 | 4-(NMe2)-3-methylphenyl |
| 281 | 2,5-difluoro-methylphenyl |
| 282 | 2,5-bis(CF3)-methylphenyl |
| 283 | 1-methylnaphthyl |
| 284 | 2-methylnaphthyl |
| 285 | phenylpropyl |
| 286 | methylcyclohexyl |
| 287 | methylpyrazinyl |
| 288 | 4-methylquinolinyl |

EXAMPLE 279 mp 242–244° C. (decomposition).

HR-FAB-:474.0788 (-1.0 mmu).

EXAMPLE 280 mp 209–211° C. (decomposition).

Anal.Calcd. for $C_{22}H_{19}N_7O_7 \cdot H_2O$: C,51.66;H,4.14;N,19.17. Found:C,51.72;H,4.15;N,18.46.

HR-FAB-:492.1248 (-2.0 mmu).

EXAMPLE 281 mp 241–243° C. (decomposition).

Anal.Ca;cd. for $C_{20}H_{12}F_2N_6O_7 \cdot 3/2H_2O$: C,46.79;H,2.95;N,16.37. Found:C,46.90;H,2.58;N,16.11.

HR-FAB-:485.0650 (-0.7 mmu).

EXAMPLE 282 mp 217–219° C. (decomposition).

HR-FAB-:585.0613 (+1.9 mmu).

EXAMPLE 283)

mp 224–226° C. (decomposition).

Anal.Calcd. for $C_{24}H_{16}N_6O_7 \cdot H_2O$: C,55.60;H,3.50;N,16.21. Found:C,55.67;H,3.39;N,15.88.

HR-FAB-:499.1031 (+2.9 mmu).

EXAMPLE 284 mp 275–277° C. (decomposition).

Anal. Calcd.for $C_{24}H_{16}N_6O_7 \cdot 3/4H_2O$: C,56.09;H,3.43;N,16.18. Found:C,56.25;H,3.36;N,15.94.

HR-FAB-:499.1021 (+1.9 mmu).

EXAMPLE 285 mp 212–214° C. (decomposition).

Anal.Calcd. for $C_{22}H_{18}N_6O_7 \cdot 1/2H_2O$: C,54.21;H,3.93;N,17.24. Found:C,54.22;H,3.78;N,17.21.

HR-FAB-:477.1151 (-0.8 mmu).

EXAMPLE 286 mp 237–239° C. (decomposition).

Anal.Calcd. for $C_{20}H_{20}N_6O_7 \cdot 3/4H_2O$: C,51.12;H,4.61,N,17.88. Found:C,51.35;H,4.62;N,17.44.

HR-FAB-:455.1324 (-2.0 mmu).

EXAMPLE 287 mp >300° C.

Anal.Calcd. for $C_{18}H_{12}N_8O_7 \cdot HCl \cdot 3/5H_2O$: C,43.27;H,2.86;N,22.43. Found:C,43.21;H,2.83;N,22.55.

HR-FAB-:451.0753 (+0.3 mmu).

EXAMPLE 288 mp >300° C.

Anal.Calcd. for $C_{23}H_{15}N_7O_7 \cdot 2HCl \cdot 3.3H_2O$: C,43.59;H,3.75;N,15.47. Found:C,43.25;H,3.36;N,15.08.

HR-FAB-:500.0960 (+0.5 mmu).

EXAMPLE 289

7-(4-((N-((4-Bromophenyl)methyl)carbamoyloxy)methyl)imidazolyl)-3,4-dihydro-6-nitro-3-oxoquinoxaline-2-carboxylic Acid

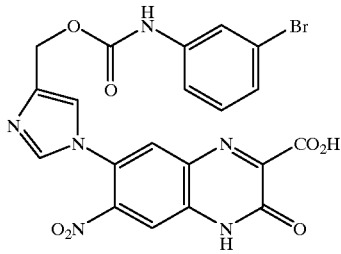

To a solution of the compound in Example 263 (121 mg, 202 μmol) in acetic acid (2.5 ml) was added hydrochloric acid (0.5 ml), and the mixture was stirred for 20 hours at room temperature. Water was added to the reaction mixture and, after the precipitate was filtered off, the reaction mixture were purified with synthetic adsorbent Sepabeads® SP850 [water→water-acetonitrile (20:1→2:1)] to obtain 22.2 mg of the title compound as yellow powder. Yield 20%.

mp 217–219° C. (decomposition).

Anal.Calcd. for $C_{21}H_{15}BrN_6O_7 \cdot 1/2H_2O$: C,45.67;H,2.92;N,15.22. Found:C,45.71;H,2.79;N,15.20.

HR-FAB-:541.0099 (-0.8 mmu).

EXAMPLES 290 THROUGH 293

Through the same process as in Example 289, compounds listed in following Table 18 were obtained.

TABLE 18

| Example | R |
|---|---|
| 290 | 3-bromophenyl-ethyl |
| 291 | 2-bromophenyl-ethyl |
| 292 | 2,5-difluoro-4-methylphenyl |

TABLE 18-continued

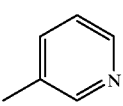

| Example | R |
|---|---|
| 293 | 3-pyridylmethyl |

EXAMPLE 290 mp 159–161° C. (decomposition).
Anal.Calcd. for $C_{21}H_{15}BrN_6O_7$: C,46.43;H,2.78;N,15.47. Found:C,46.55;H,2.87;N,14.92.
HR-FAB–:541.0085 (–2.2 mmu).

EXAMPLE 291 mp 187–189° C. (decomposition).
Anal.Calcd. for $C_{21}H_{15}BrN_6O_7$: C,46.43;H,2.78;N,15.47. Found:C,46.13;H,2.80;N,15.34.
HR-FAB–:541.0113 (+0.6 mmu).

EXAMPLE 292 mp 218–220° C. (decomposition).
Anal.Calcd. for $C_{20}H_{12}F_2N_6O_7 \cdot 2/3H_2O$: C48.20;H, 2.68;N,16.86. Found:C,48.40;H,2.85;N,16.50.
HR-FAB–:485.0698 (+4.1 mmu).

EXAMPLE 293 mp 228–230° C. (decomposition).
Anal.Calcd. for $C_{19}H_{13}N_7O_7 \cdot H_2O$: C,48.61;H,3.22;N, 20.89. Found:C,48.38: H,3.11;N,20.99.
HR-FAB–:450.0784 (–1.5 mmu).

EXAMPLE 294

Ethyl 3-ethoxy-7-(4-((N-(4-ethoxycarbonyl-2-fluorophenyl)carbamoyloxy)methyl)imidazolyl)-6-nitroquinoxaline-2-carboxylate

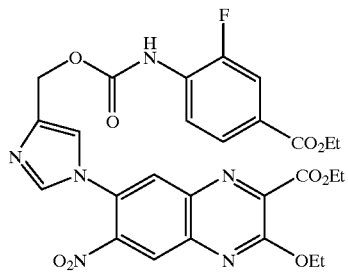

To a solution of the compound in Example 84 (500 mg, 1.29 mmol) in methylene chloride (10 ml) was added ethyl 4-isocyanato-3-fluorobenzoate (541 mg, 2.59 mmol), and the mixture was stirred for 2 hours at room temperature. After allowed to stand statically overnight, solvent was distilled off and the residue obtained was purified by means of silica gel column chromatography [hexane-ethyl acetate (2:1 1:2)] to obtain 670 mg of the title compound as pale yellow powder. Yield 87%.

$^1$H-NMR(DMSO-$d_6$,δ):1.31(3H,t,J=6.8 Hz),1.36(3H,t,J= 6.8 Hz), 1.43(3H,t,J=6.8 Hz),4.30(2H,q,J=6.8 Hz),4.48(2H, q,J=6.8 Hz), 4.62(2H,q,J=6.8 Hz),5.14(2H,s),7.62(1H,s), 7.70(1H,d,J=11.2 Hz), 7.77(1H,d,J=8.3 Hz),8.00(1H,t,J=8.3 Hz),8.46(1H,s),8.66(1H,s), 9.93(1H,s).

EXAMPLE 295

Ethyl 3-ethoxy-7-(4-((N-(5-ethoxycarbonyl-2-fluorophenyl)carbamoyloxy)methyl)imidazolyl)-6-nitroquinoxaline-2-carboxylate

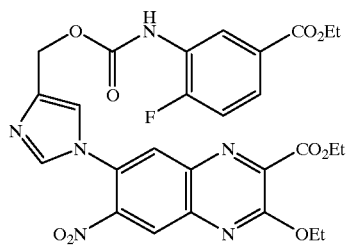

Using the compound in Example 84 (200 mg, 516 μmol) and following the same process as in Example 294, 249 mg of the title compound were obtained as pale yellow powder. Yield 81%.

$^1$H-NMR(DMSO-$d_6$,δ):1.31(3H,t,J=7.3 Hz),1.36(3H,t,J= 7.3 Hz), 1.43(3H,t,J=7.3 Hz),4.31(2H,q,J=7.3 Hz),4.48(2H, q,J=7.3 Hz), 4.62(2H,q,J=7.3 Hz),5.12(2H,s),7.37(1H,t,J= 9.3 Hz),7.62(1H,s), 7.71–7.75(1H,m),8.06(1H,s),8.38(1H,d, J=5.9 Hz),8.46(1H,s), 8.66(1H,s),9.74(1H,s).

EXAMPLE 296

Ethyl 3-ethoxy-7-(4-((N-(2-ethoxycarbonylphenyl)carbamoyloxy)methyl)imidazolyl)-6-nitroquinoxaline-2-carboxylate

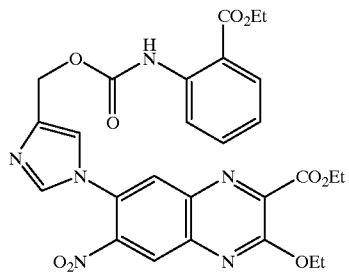

Using the compound in Example 84 (200 mg, 516 μmol) and following the same process as in Example 294, 199 mg of the title compound were obtained as pale yellow powder. Yield 67%.

$^1$H-NMR(DMSO-$d_6$,δ):1.32(3H,t,J=7.3 Hz),1.37(3H,t,J= 7.3 Hz), 1.43(1H,t,J=7.3 Hz),4.32(2H,q,J=7.3 Hz),4.48(2H, q,J=7.3 Hz), 4.62(2H,q,J=7.3 Hz),5.12(2H,s),7.16(1H,t,J= 8.8 Hz),7.625(1H,s), 7.634(1H,t,J=8.8 Hz),7.95(1H,d,J=8.8 Hz),8.05(1H,s), 8.18(1H,d,J=8.8 Hz),8.49(1H,s),8.66(1H,s), 10.33(1H,s).

EXAMPLE 297

7-(4-((N-(4-Carboxy-2-fluorophenyl)carbamoyloxy)methyl)imidazolyl)-3,4-dihydro-6-nitro-3-oxoquinoxaline-2-carboxylic Acid

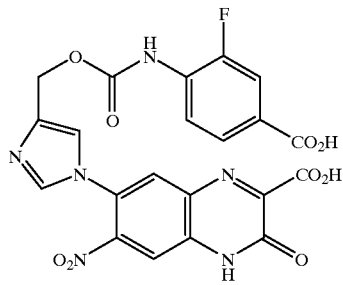

To a suspension of the compound in Example 294 (670 mg, 1.12 mmol) in ethanol (50 ml) were added 1N aqueous solution of sodium hydroxide (3.37 ml, 3.37 mmol) and successively water (1 ml), and the mixture was refluxed for 1 hour under Ar gas. After cooling, 47% hydrobromic acid (16 ml) was added and the mixture was stirred for 24 hours at room temperature. The reaction mixture was concentrated under reduced pressure and, after washed with water, the residue was air-dried to obtain 254 mg of the title compound as brown powder. Yield 44%.

mp 250–252° C. (decomposition).

HR-FAB–:511.0683 (+3.3 mmu).

EXAMPLE 298

7-(4-((N-(5-Carboxy-2-fluorophenyl)carbamoyloxy)methyl)imidazolyl)- 3,4-dihydro-6-nitro-3-oxoquinoxaline-2-caroxylic Acid

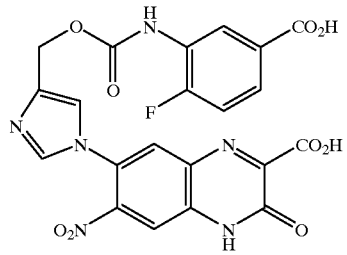

Using the compound in Example 295 (100 mg, 168 μmol), through the same process as in Example 297, 28.0 mg of the title compound were obtained as brown powder. Yield 33%.

mp >300° C.

HR-FAB–:511.0633 (–1.7 mmu).

EXAMPLE 299

7-(4-((N-(2-Carboxyphenyl)carbamoyloxy)methyl)imidazolyl)-3,4-dihydro-6-nitro-3-oxoquinoxaline-2-carboxylic Acid

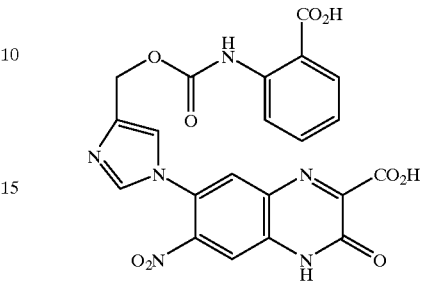

Using the compound in Example 296 (97.0 mg, 197 μmol) and following the same process as in Example 297, 81.0 mg of the title compound were obtained as brown powder. Quantitative yield.

mp 216–218° C. (decomposition).

HR-FAB–:493.0752 (+0.8 mmu).

EXAMPLE 300

3,4-Dihydro-7-(4-((N-2-ethoxycarbonylphenyl)carbamoyloxy)methyl)imidazolyl)-6-nitro-3-oxoquinoxaline-2-carboxylic Acid

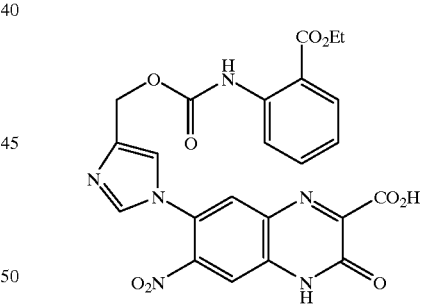

To a solution of the compound in Example 296 (197 mg, 341 μmol) in acetic acid (5 ml) was added concentrated hydrochloric acid (1 ml), and the mixture was stirred for 4 hours at room temperature, then, allowed to stand statically overnight. The reaction mixture was concentrated under reduced pressure and, after washed with water, the residue was air-dried to obtain 17.0 mg of the title compound as brown powder. Yield 10%.

mp 182–184° C. (decomposition).

HR-FAB–:521.1070 (+1.3 mmu).

EXAMPLE 301

Ethyl 3-ethoxy-7-(4-(2-hydroxyethyl)imidazolyl)-6-nitroquinoxaline-2-carboxylate

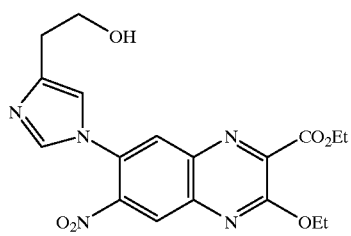

To a solution of the compound in Example 139 (309 mg, 999 μmol) in N,N-dimethylacetamide (10 ml) were added 4-(2-hydroxyethyl)imidazole (270 mg, 2.41 mmol) and triethylamine (1 ml) in sequence, and the mixture was stirred for 15 hours at 120° C. The reaction mixture was concentrated under reduced pressure and purified by means of silica gel column chromatography [methylene chloride→methylene chloride-methanol (10:1)] to obtain 114 mg of the title compound as yellowish brown powder. Yield 28%.

$^1$H-NMR(CDCl$_3$,δ):1.47(3H,t,J=6.8 Hz),1.53(3H,t,J=7.3 Hz), 2,81(1H,d,J=4,4 Hz),2.87–2.92(2H,m),3.97(2H,t,J=5.9 Hz), 4.55(2H,q,J=6.8 Hz),4.66(2H,q,J=7.3 Hz),6.94(1H,d,J=1.0 Hz), 7.66(1H,d,J=1.0 Hz),8.15(1H,s),8.42(1H,s).

EXAMPLE 302

7-(4-(2-(N-(4-Carboxyphenyl)carbamoyloxy)ethyl)imidazolyl)-3,4-dihydro-6-nitro-3-oxoquinoxaline-2-carboxylic Acid

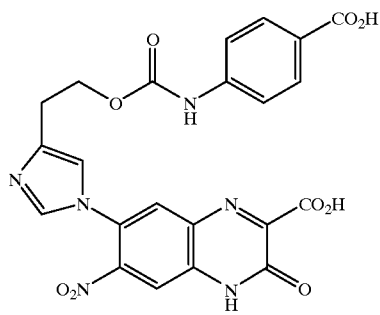

To a solution of the compound in Example 301 (110 mg, 274 μmol) in acetonitrile (5 ml) was added ethyl 4-isocyanatobenzoate (57.0 mg, 298 μmol), andthe mixture was allowed to stand statically overnight. The residue obtained by concentrating the reaction mixture under reduced pressure was purified by means of silica gel column chromatography [methylene chloride→methylene chloride-methanol (50:1)]. This was dissolved into acetic acid-concentrated hydrochloric acid (5:1, 6 ml) and stirred for 20 minutes at 80° C., then allowed to stand statically overnight at room temperature. The residue obtained by concentrating the reaction mixture under reduced pressure was suspended into aqueous (1 ml) solution of lithium hydroxide monohydrate (60.0 mg, 1.43 mmol), then dissolved by adding methanol (5 ml) and the solution was stirred for 2 hours at 50° C. 1N hydrochloric acid was added to the residue obtained by concentrating the reaction mixture under reduced pressure to bring the pH value to 2, which was concentrated again under reduced pressure. Water was added to the residue obtained, the crystals were collected by filtration, these were washed with water and with ethyl acetate in sequence, and then air-dried to obtain 70.5 mg of the title compound as yellowish brown powder. Yield 51%.

mp >300° C.

HR-FAB-:507.0902 (+0.1 mmu).

EXAMPLE 303

7-(4-(Carboxymethyl)imidazolyl)-3,4-dihydro-6-nitro-3-oxoquinoxaline-2-carboxylic Acid

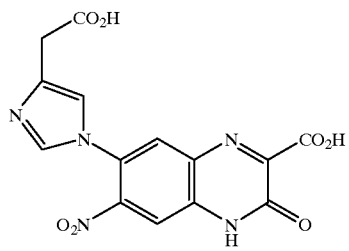

A solution of the compound in Example 139 (450 mg, 1.46 mmol) and methyl imidazole-4-acetate (617 mg, 4.40 mmol) in acetonitrile (5 ml) was stirred for 15 hours at 110° C. in sealed tube. The reaction mixture was concentrated under reduced pressure and purified by means of silica gel column chromatography [methylene chloride]. This was dissolved into acetic acid-concentrated hydrochloric acid (5:1, 3 ml) and allowed to stand statically overnight. The residue obtained by concentrating the reaction mixture under reduced pressure was dissolved into methanol, then aqueous (1 ml) solution of lithium hydroxide monohydrate (119 mg, 2.84 mmol) was added and the solution was allowed to stand statically overnight. 0.5N hydrochloric acid was added to the residue obtained by concentrating the reaction mixture under reduced pressure to make acidic, which was concentrated again under reduced pressure. Water was added to the residue obtained, the crystals were collected by filtration, these were washed with water and with ethyl acetate in sequence, and then air-dried to obtain 149 mg of the title compound as reddish brown powder. Yield 27%.

mp >300° C.

Anal.Calcd. for C$_{14}$H$_9$N$_5$O$_7$.H$_2$O: C,44.57;H,2.94;N, 18.56. Found:C,44.64;H,3.11;N,18.64.

HR-FAB-:358.0425 (+0.2 mmu).

EXAMPLE 304

3,4-Dihydro-7-(4-(hydroxymethyl)imidazolyl)-6-nitro-3-oxoquinoxaline-2-carboxylic Acid

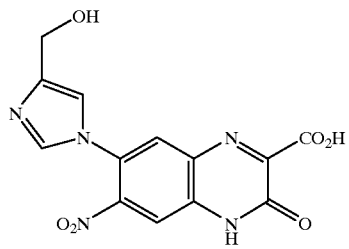

To the compound in Example 115 (200 mg, 405 μmol) was added 1N aqueous solution of lithium hydroxide (5 ml), and the mixture was stirred for 2 hours at 80° C. After cooling, the reaction mixture was made acidic using concentrated hydrochloric acid and, after filtered off the insolubles, it was purified with synthetic adsorbent Sepabeads® SP850 [water-acetonitrile=20:1] to obtain 57.8 mg of the title compound as orange powder. Yield 43%.

mp 240–242° C. (decomposition).

HR-FAB–:330.0458 (–1.7 mmu).

EXAMPLE 305

Ethyl 3-ethoxy-7-(3-((N-(4-ethoxycarbonylphenyl)carbamoyloxy)methyl)-4-pyridone-1-yl)-6-nitroquinoxaline-2-carboxylate

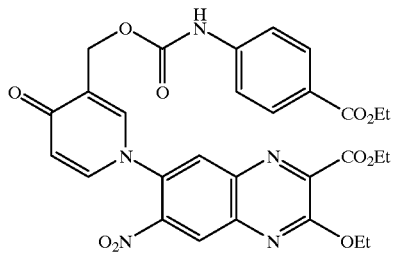

To a solution of the compound in Example 120 (500 mg, 1.21 mol) in benzene (30 ml) was added ethyl 4-isocyanatobenzoate (463 mg, 2.42 mmol), and the mixture was refluxed for 2 hours. After cooling, the precipitate was collected by filtration, washed with benzene and then air-dried to obtain 692 mg of the title compound as yellow powder. Yield 94%.

$^1$H-NMR(CDCl$_3$,δ):1.37(3H,t,J=7.3 Hz),1.47(3H,t,J=7.3 Hz), 1.54(1H,t,J=6.9 Hz),4.34(2H,q,J=7.3 Hz),4.55(2H,q,J=7.3 Hz), 4.68(2H,q,J=6.9 Hz),5.15(2H,s),6.56(1H,d,J=7.8 Hz), 7.39(1H,dd,J=7.8,2.5 Hz),7.43(2H,d,J=8.8 Hz),7.71(1H,d,J=2.5 Hz), 7.97(2H,d,J=8.8 Hz),8.22(1H,s),8.57(1H,s).

EXAMPLE 306

7-(3-((N-(4-Ethoxycarbonylphenyl)carbamoyloxy)methyl)-4-pyridone-1-yl)-3,4-dihydro-6-nitro-3-oxoquinoxaline-2-carboxylic Acid

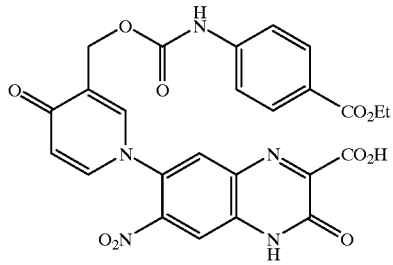

To a solution of the compound in Example 305 (692 mg, 1.14 mmol) in acetic acid (12 ml) was added concentrated hydrochloric acid (3 ml), and the mixture was stirred for 18 hours at room temperature. Water was added to the reaction mixture and the precipitate was collected by filtration, washed with water and then air-dried to obtain 548 mg of the title compound as yellow powder. Yield 86%.

mp 201–203° C. (decomposition).

Anal.Calcd. for C$_{25}$H$_{19}$N$_5$O$_{10}$.1/2H$_2$O: C,53.78;H,3.61;N,12,54. Found:C,53.82;H,3.69;N,12,60.

HR-FAB–:548.1053 (–0.1 mmu).

EXAMPLE 307

7-(3-((N-(4-Carboxyphenyl)carbamoyloxy)methyl)-4-pyridone-1-yl)-3,4-dihydro-6-nitro-3-oxoquinoxaline-2-carboxylic Acid

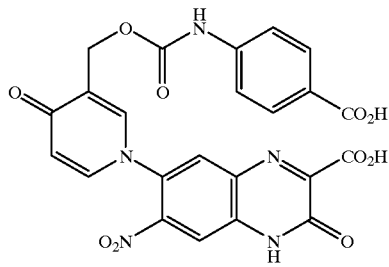

To a suspension of the compound in Example 306 (383 mg, 697 μmol) in water (4 ml) was added 1N aqueous solution of lithium hydroxide (6.97 ml, 6.97 mmol), and the mixture was stirred for 3 hours at room temperature. After the reaction mixture was purified with synthetic adsorbent Sepabeads® SP850 [water:acetonitrile=20:1], water was added and the pH value was brought to 2 with concentrated hydrochloric acid. The precipitate was collected by filtration, washed with water and then air-dried to obtain 253 mg of the title compound as yellow powder. Yield 65%.

mp 231–233° C. (decomposition).

Anal.Calcd. for C$_{23}$H$_{15}$N$_5$O$_{10}$.2H$_2$O: C,49.56;H,3.44;N,12.56. Found:C,49.32;H,3.41;N,12.47.

HR-FAB–:520.0740 (+0.0 mmu).

EXAMPLE 308

Ethyl 3-ethoxy-7-((4-hydroxymethyl)imidazole-1-yl)methyl-6-nitroquinoxaline-2-carboxylate

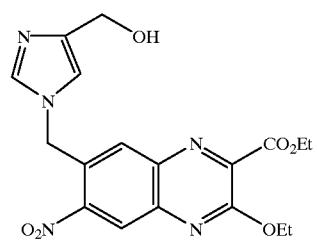

To a solution of ethyl 3-ethoxy-7-methyl-6-nitroquinoxaline-2-carboxylate (2.00 g, 6.55 mmol) in carbon tetrachloride (200 ml) was added N-bromosuccinimide (3.51 g, 19.7 mmol), then the reaction mixture was heated to 80° C. 2,2'-Azobisisobutyronitrile (215 mg, 1.31 mmol) was added to the reaction mixture and the mixture was refluxed for 6 hours. After cooling, the insolubles were filtered off and solvent was distilled off. After dissolved the residue obtained into acetonitrile (50 ml), 4-(hydroxymethyl)imidazole hydrochloride (2.21 g, 16.4 mmol) and triethylamine (2.28 ml, 16.4 mmol) were added and the mixture was refluxed for 6 hours. The reaction mixture was distilled off under reduced pressure and the residue obtained was purified by means of silica gel column chromatography [ethyl acetate] to obtain 293 mg of the title compound as yellowish white powder. Yield 11%.

$^1$H-NMR(CDCl$_3$,δ):1.44(3H,t,J=7.3 Hz),1.50(3H,t,J=7.3 Hz), 4.51(2H,q,J=7.3 Hz),4.55(2H,s),4.63(2H,q,J=7.3 Hz), 5.77(2H,s), 7.11(1H,s),7.41(1H,s),7.58(1H,s),8.63(1H,s).

EXAMPLE 309

Ethyl 3-ethoxy-7-(4-((N-(4-ethoxycrbonylphenyl)carbamoyloxy)methyl)imidazolyl)methyl-6-nitroquinoxaline-2-carboxylate

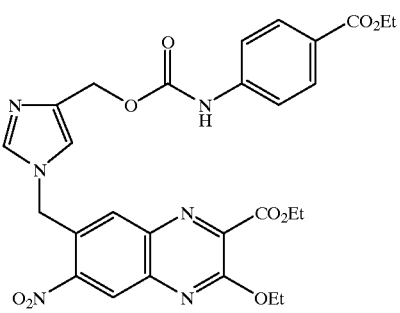

Using the compound in Example 308 (40.1 mg, 100 μmol) and following the same process as in Example 257, 49.2 mg of the title compound were obtained as light brown powder. Yield 83%.

$^1$H-NMR(CDCl$_3$,δ):1.39(3H,t,J=7.3 Hz),1.435(3H,t,J= 6.9 Hz), 1.439(3H,t,J=7.3 Hz),4.35(2H,q,J=7.3 Hz),4.44 (2H,q,J=6.9 Hz), 4.49(2H,q,J=7.3 Hz),5.17(2H,s),5.76(2H, s),6.70–6.90(1H,br), 7.05(2H,d,J=8.3 Hz),7.31(1H,s),7.34 (1H,s),7.70(1H,s), 7.85(2H,d,J=8.8 Hz),8.47(1H,s).

EXAMPLE 310

Ethyl 3-ethoxy-7-(4-((N-(3-ethoxycarbonylphenyl)carbamoyloxy)mewthyl)imidazolyl)methyl-6-nitroquinoxaline-2-carboxylate

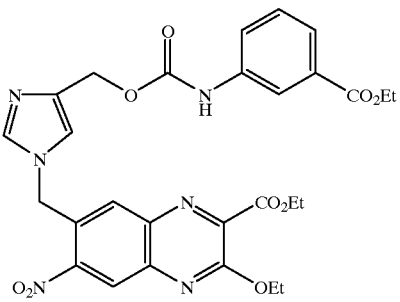

Using the compound in Example 308 (253 mg, 630 μmol) and following the same process as in Example 257, 314 mg of the title compound were obtained as light brown powder. Yield 84%.

$^1$H-NMR(DMSO-d$_6$,δ):1.32(3H,t,J=6.8 Hz),1.33(3H,t,J= 7.3 Hz), 1.35(3H,t,J=6.9 Hz),4.30(2H,q,J=6.8 Hz),4.37(2H, q,J=7.3 Hz), 4.38(2H,q,J=6.9 Hz),5.20(2H,s),5.85(2H,s), 6.88(1H,s), 7.16–7.22(2H,m),7.25(1H,s),7.47(1H,d,J=6.9 Hz),7.57(1H,s), 7.93(1H,s),8.29(1H,s),9.24(1H,s).

EXAMPLE 311

7-(4-((N-(3-Carboxyphenyl)carbamoyloxy)methyl)imidazolyl)methyl-3,4-dihydro-6-nitro-3-oxoquinoxaline-2-carboxylic Acid

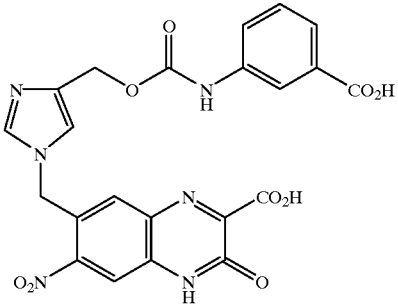

To a solution of the compound in Example 310 (314 mg, 530 μmol) in acetic acid (4 ml) was added concentrated hydrochloric acid (1 ml), and the mixture was allowed to stand statically for 3 days at room temperature. Water was added to the reaction mixture, and the precipitate was collected by filtration, washed with water and then air-dried. 1N aqueous solution of sodium hydroxide (5.30 ml, 5.30 mmol) was added thereto and the mixture was stirred for 6 hours at room temperature. After filtered off the insolubles, the pH value was brought to 2 with concentrated hydrochloric acid. The precipitate was collected by filtration, washed with water and then air-dried to obtain 30.5 mg of the title compound as yellowish brown powder. Yield 11%.

mp 229–231° C. (decomposition).

HR-FAB–:507.0923 (+2.2 mmu).

EXAMPLE 312

Ethyl 3-ethoxy-6-nitro-7-(3-((phenylaminocarbonylamino)methyl)pyrrolidine-1-yl)quinoxaline-2-carboxylate

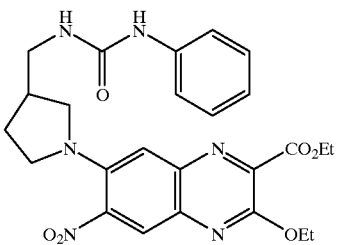

To a solution of the compound in Example 139 (1.00 g, 3.23 mmol) in acetonitrile (16 ml) was added 3-(aminomethyl)pyrrolidine (647 mg, 6.46 mmol), and the mixture was refluxed for 2 hours. The residue obtained by concentrating the reaction mixture under reduced pressure was purified by means of silica gel column chromatography [methylene chloride-methanol=20:1] to obtain dark red amorphous material. This was dissolved into methylene chloride (10 ml) and, after phenyl isocyanate (219 μl, 2.01 mmol) was added, the mixture was stirred for 2 hours at room temperature. The residue obtained by concentrating the reaction mixture was purified by means of silica gel column chromatography [hexane-ethyl acetate=1:1] to obtain 401 mg of the title compound as red powder. Yield 24%.

¹H-NMR(CDCl₃,δ):1.46(3H,t,J=6.9 Hz),1.47(3H,t,J=6.8 Hz), 1.70–1.90(1H,m),2.00–2.20(1H,m),2.50–2.70(1H,m), 3.05–3.15(1H,m),3.20–3.50(5H,m),4.53(2H,q,J=6.9 Hz), 4.54(2H,q,J=6.8 Hz),5.10–5.30(1H,br),6.60–6.70(1H,br), 7.00–7.10(1H,m),7.31(4H,d,J=4.4 Hz),7.38(1H,s),8.09(1H, s).

EXAMPLE 313

3,4-Dihydro-6-nitro-3-oxo-7-(3-((phenylaminocarbonylamino)methyl)pyrrolidine-1-yl)quinoxaline-2-carboxylic Acid

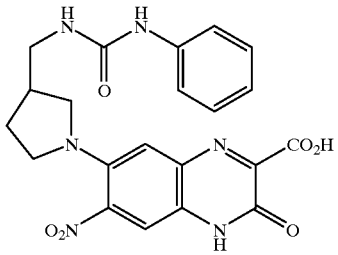

To a solution of the compound in Example 312 (401 mg, 789 μmol) in acetic acid (4 ml) was added concentrated hydrochloric acid (1 ml), and the mixture was stirred for 22 hours at room temperature. After the reaction mixture was concentrated under reduced pressure, water (20 ml) was added and the pH value was brought to 9 using 1N aqueous solution of sodium hydroxide. This was washed with ethyl acetate and then the pH value was brought to 2 with concentrated hydrochloric acid. The precipitate was collected by filtration, washed with water and then air-dried to obtain 42.0 mg of the title compound as dark brown powder. Yield 12%.
mp >300° C.
HR-FAB–:451.1378 (+1.2 mmu).

REFERENTIAL EXAMPLE 1

Ethyl 3-ethoxy-7-nitro-6-trifluoromethylquinoxaline-2-carboxylate

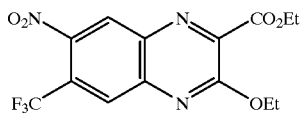

To a solution of ethyl 3,4-dihydro-3-oxo-6-trifluoromethylquinoxaline-2-carboxylate (500 mg, 1.75 mmol) in concentrated sulfuric acid (5 ml) was added potassium nitrate (354 mg, 3.50 mmol) at 40° C., and the mixture was stirred for 3 hours at the same temperature. The reaction mixture was poured into ice water (100 ml), which was extracted with ethyl acetate. After dried over anhydrous sodium sulfate, solvent was distilled off. Silver oxide (I)(811 mg, 3.50 mmol) was added to the residue obtained which was suspended into toluene (10 ml). Then, iodoethane (280 μl, 3.50 mmol) was added dropwise at 100° C. and the mixture was refluxed for 2 hours. After cooling, the insolubles were filtered off using celite and the solvent was distilled off. The residue obtained was submitted to silica gel column chromatography [hexane-ethyl acetate=8:1] to obtain 255 mg of the title compound as yellowish brown oily product. Yield 41%.
¹H-NMR(CDCl₃,δ):1.48(3H,t,J=7.3 Hz),1.53(3H,t,J=7.3 Hz), 4.56(2H,q,J=7.3 Hz),4.68(2H,d,J=7.3 Hz),8.32(1H,s), 8.67(1H,s).

REFERENTIAL EXAMPLE 2

Ethyl 7-amino-1,2-dihydro-3-ethoxy-6-triflubromethylquinoxaline-2-carboxylate

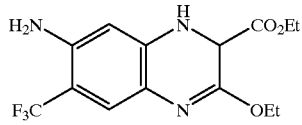

To a solution of the compound in Referential example 1 (4.98 g, 13.9 mmol) in ethanol (100 ml) was added 10% palladium on carbon (500 mg), and the mixture was stirred for 3 hours at room temperature under hydrogen atmosphere. Catalyst was filtered off using celite and then solvent was distilled off to obtain 4.01 g of the title compound as yellow powder. Yield 87%.
¹H-NMR(CDCl₃,δ):1.25(3H,t,J=7.3 Hz),1.36(3H,t,J=7.3 Hz), 3.98(2H,brs),4.18(2H,q,J=7.3 Hz),4.31–4.44(2H,m), 4.49(1H,d,J=1.5 Hz),4.65(1H,brs),6.01(1H,s),7.18(1H,s).

REFERENTIAL EXAMPLE 3

Ethyl 7-amino-3-oxo-1,2,3,4-tetrahydro-6-trifluoromethylquinoxaline-2-carboxylate

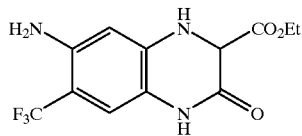

To a solution of the compound in Referential example 2 (3.51 g, 10.6 mmol) in ethanol (35 ml) was added concentrated hydrochloric acid (7 ml), and the mixture was stirred for 20 hours at room temperature. After solvent was distilled off, water was added and the solution was extracted with ethyl acetate. After dried over anhydrous sodium sulfate, solvent was distilled off to obtain 2.69 g of the title compound as light brown powder. Yield 84%.
¹H-NMR(DMSO-d₆,δ):1.16(3H,t,J=7.3 Hz),4.07–4.13 (2H,m), 4.53(1H,d,J=2.0 Hz),5.10(2H,brs),6.18(1H,s),6.70 (1H,s), 7.04(1H,d,J=1.5 Hz),10.36(1H,s).

REFERENTIAL EXAMPLE 4

5-Acetamido-2-((4-hydroxymethyl)imidazole-1-yl)-4-nitrobenzotrifluoride

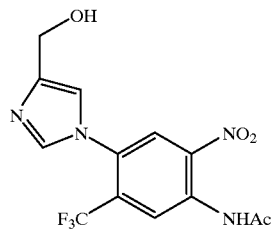

To a solution of 5-acetamido-2-fluoro-4-nitrobenzotrifluoride (2.00 g, 7.51 mmol) in acetonitrile (40 ml) were added (4-hydroxymethyl)imidazole hydrochloride (5.07 g, 37.6 mmol) and triethylamine (10 ml), and the mixture was stirred for 24 hours at 120° C. in sealed tube.

After cooling, ethyl acetate was added to the reaction mixture and washed with brine. Then, this was dried over anhydrous sodium sulfate and solvent was distilled off. The residue obtained was submitted to silica gel column chromatography [methylene chloride-methanol (50:1 20:1)] to obtain 198 mg of the title compound as pale yellow powder. Yield 8%.

$^1$H-NMR(DMSO-d$_6$,δ):2.12(3H,s),4.41(2H,d,J=5.9 Hz), 5.02(1H,t,J=5.9 Hz),7.26(1H,s),7.79(1H,s), 8.13(1H,s),8.14 (1H,s),10.69(1H,s).

REFERENTIAL EXAMPLE 5

5-Amino-2-((4-hydroxymethyl)imidazole-1-yl)-4-nitrobenzotrifluoride

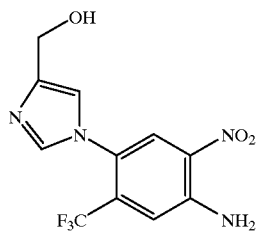

To the compound in Referential example 4 (17.0 mg, 59.2 μmol) was added 4N hydrochloric acid (1 ml), and the mixture was refluxed for 3 hours. The reaction mixture was concentrated under reduced pressure and the residue obtained was washed with water, then air-dried to obtain 12.0 mg of the title compound as yellow powder. Yield 83%.

$^1$H-NMR(DMSO-d$_6$,δ):4.39(2H,d,J=5.4 Hz),4.96(1H,t,J= 5.4 Hz), 7.12(1H,s),7.60(1H,s),7.66(2H,s),7.95(1H,s),8.00 (1H,s).

REFERENTIAL EXAMPLE 6

4,5-Diamino-2-((4-hydroxymethyl)imidazole-1-yl) benzotrifluoride

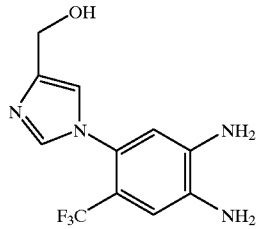

To a solution of the compound in Referential example 5 (220 mg, 728 μmol) in ethanol (5 ml) was added 10% palladium on carbon (20.0 mg), and the mixture was stirred for 3 hours at room temperature under hydrogen atmosphere. Catalyst was filtered off and solvent was distilled off to obtain 200 mg of the title compound as light orange powder. Quantitative yield.

$^1$H-NMR(DMSO-d$_6$,δ):4.37(2H,d,J=5.9 Hz),4.89(1H,t,J= 5.9 Hz), 5.13(2H,s),5.42(2H,s),6.45(1H,s),6.87(1H,s),6.99 (1H,s), 7.52(1H,s).

REFERENTIAL EXAMPLE 7

Ethyl 3-ethoxy-7-fluoro-6-methylthioquinoxaline-2-carboxylate

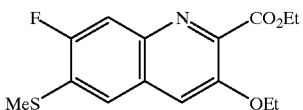

To a solution of the compound in Example 139 (1.00 g, 3.23 mmol) in N,N-dimethylformamide (10 ml) was added sodium thiomethoxide (249 mg, 3.55 mmol) at room temperature, and the mixture was stirred for 8 hours at 50° C. Water was added to the reaction mixture which was extracted with ethyl acetate. After dried over anhydrous sodium sulfate, solvent was distilled off under reduced pressure. The residue obtained was purified by means of silica gel column chromatography [hexane-ethyl acetate= 4:1] to obtain 450 mg of the title compound as yellow powder. Yield 45%.

$^1$H-NMR(CDCl$_3$,δ):1.46(3H,t,J=6.9 Hz),1.49(3H,t,J=6.9 Hz), 2.62(3H,s),4.51(2H,q,J=6.9 Hz),4.57(2H,q,J=6.9 Hz), 7.51(1H,d,J=7.3 Hz),7.68(1H,d,J=10.3 Hz).

BIOLOGICAL ACTIVITY

Binding Experiment to AMPA Receptor

Crude synaptosome membrane preparations prepared from cerebral cortex of rats were added [$^3$H]-AMPA (final concentration: 5 nM) that was bound selectively to AMPA receptor, potassium thiocyanate (final concentration: 100 mM) and testing compound, and the mixtures were incubated for 30 minutes at 0° C. After the reactions were stopped by suction filtration, the radio activity on the filter was measured with liquid scintillation counter. The specific binding of [$^3$H]-AMPA was determined by subtracting nonspecific binding level in the presence of glutamic acid (0.1 mM) from overall binding level. Putting the binding of [$^3$H]-AMPA in the absence of testing compound on 100, the concentration of compound to decrease by 50% (IC$_{50}$ value) was determined and was converted these to Ki values to calculate the binding capacity of each compound to AMPA receptor (Eur. J. Pharmacol., 1993, 246, 195–204).

TABLE 19

Activity table - A

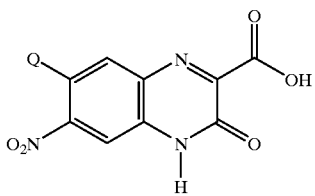

| Testing compound | Q | [$^3$H] -AMPA Ki:nM |
|---|---|---|
| Example 5 | Cl | 1260 |
| Example 6 | F | 2010 |
| Example 7 | Br | 630 |
| Example 8 | CH$_3$ | 330 |

TABLE 19-continued

Activity table - B

| Example | Structure | Value |
|---|---|---|
| Example 35 | N-ethylimidazole | 2040 |
| Example 36 | N-methylimidazole | 450 |
| Example 37 | 1-methyl-4-pyridinone | 330 |
| Example 39 | Me₂N— | 910 |
| Example 62 | PhO— | 860 |
| Example 66 | N-ethylimidazole | 360 |

Activity table - C

| Testing compound | Y | U | W | [³H] -AMPA (Ki:nM) |
|---|---|---|---|---|
| Example 79 | CH | NH | 4-CO2H-Ph | 37.3 |
| Example 80 | CH | NH | 2-F-4-CO2H-Ph | 11.8 |
| Example 83 | N | O | 4-CO2H-Ph | 15.8 |

Activity table - D

| Testing compound | Y | U | W | [³H] -AMPA (Ki:nM) |
|---|---|---|---|---|
| Example 88 | N | O | Ph | 86.2 |
| Example 96 | N | O | 2-F-Ph | 28.2 |
| Example 101 | N | O | 2-CF3-Ph | 32.3 |
| Example 115 | N | O | 4-CO2H-Ph | 21.6 |
| Example 116 | N | O | 3-CO2H-Ph | 27.3 |
| Example 119 | N | NH | 4-CO2H-Ph | 28.2 |

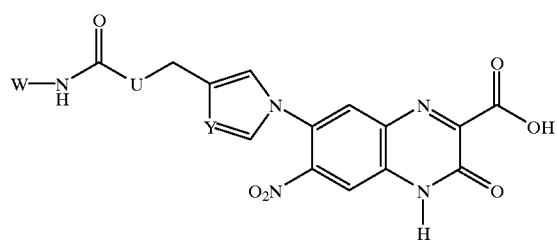

| Testing compound | Y | U | W | [³H] -AMPA (Ki:nM) |
|---|---|---|---|---|
| Example 121 | N | O | Ph | 172 |
| Example 123 | N | O | 3-Br-Ph | 48.1 |

Utilizability in the Industry

From the results above, the inventive 6,7-asymmetrically disubstituted quinoxalinecarboxylic acid derivatives are novel compounds with excellent antagonism against AMPA receptor of excitatory amino acid receptors, in particular, non-NMDA receptor.

Since these inventive compounds inhibit the binding of excitatory amino acid, which causes death of nerve cells, to AMPA receptor, they are effective for the therapy of disorder of cerebral nerve cells etc. due to said excitatory amino acid, and also can be said to be useful compounds not expressing side effects that the drugs with antagonism against NMDA receptor.

What is claimed is:

1. A 6,7-asymmetrically disubstituted quinoxalinecarboxylic acid compound represented by formula (1-a)

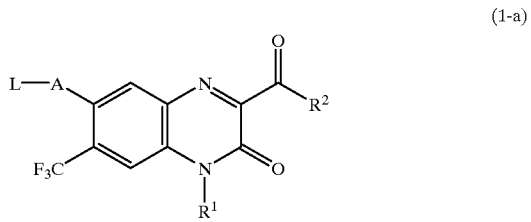

(1-a)

wherein, L denotes formula (4)

(4)

(wherein V denotes a single bond, a lower alkylene group or a lower alkenylene group, T denotes a phenyl group, naphthyl group, 5- or 6-membered heterocycle and its condensed ring (each of which may have one or more substituents on the aromatic ring or heterocycle), a hydroxyl group, a thiol group, a substituted or unsubstituted amino group, a lower alkoxycarbonyl group, a carboxyl group, an aldehyde group, formula (4-a)

(4-a)

or formula (4-b)

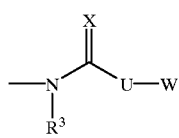

(4-b)

(wherein U denotes an oxygen atom or sulfur atom, X denotes an oxygen atom or sulfur atom, W denotes an aralkyl group, a phenyl group, a naphthyl group, a 5- or 6-membered heterocycle and its condensed ring (each of which may have one or more substituents on the aromatic ring or heterocycle), a lower alkyl group which may be unsubstituted or substituted with at least one halogen atom or a cycloalkyl group, and $R^3$ denotes an aralkyl group, a phenyl group, a naphthyl group, a 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group), or formula (4-c)

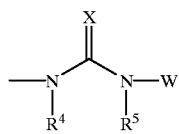

(4-c)

(wherein X denotes an oxygen atom or sulfur atom, W denotes an aralkyl group, a phenyl group, a naphthyl group, a 5- or 6-membered heterocycle and its condensed ring (each of which may have one or more substituents on the aromatic ring or heterocycle), a lower alkyl group which may be unsubstituted or substituted with at least one halogen atom or a cycloalkyl group, and $R^4$ and $R^5$ are identical or different, and each independently denote an aralkyl group, a phenyl group, a naphthyl group, a 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group), ring B denotes a saturated or unsaturated heterocycle and its condensed ring (each of which may have one or more substituents on the heterocycle or its condensed ring) and which may additionally contain one or two oxygen, nitrogen or sulfur atoms, and m denotes 0 or 1);

A denotes a single bond, a lower alkylene group or a lower alkenylene group, $R^1$ denotes an aralkyl group, a phenyl group, a naphthyl group, a 5- or 6-membered heterocycle or its condensed ring (each of which may have one or more substituents on the aromatic ring or heterocycle), a hydrogen atom, a lower alkyl group which may be unsubstituted or substituted with at least one halogen atom or a cycloalkyl group, and $R^2$ denotes a hydroxyl group, a lower alkoxy group, or formula (6)

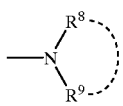

(6)

(wherein $R^8$ and $R^9$ are identical or different and each independently denote an aralkyl group, a phenyl group, a 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group, or $R^8$ and $R^9$ may form a ring (wherein said ring may additionally contain one or two heteroatoms) together with a nitrogen atom, or either of $R^8$ and $R^9$ denotes a hydrogen atom while the other denotes a phenyloxy group or an aralkyloxy group (each of which may have one or more substituents on the aromatic ring), a hydroxyl group or a lower alkoxy group), and their addition salts.

2. A 6,7-asymmetrically disubstituted quinoxalinecarboxylic acid compound represented by formula (1-b)

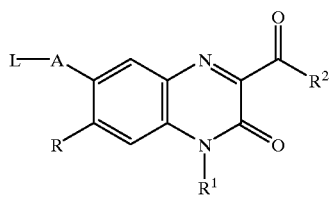

(1-b)

wherein, L denotes formula (4)

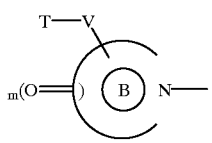

(4)

(wherein V denotes a single bond, a lower alkylene group or a lower alkenylene group, T denotes a phenyl group, a naphthyl group, a 5- or 6-membered heterocycle and its condensed ring (each of which may have one or more substituents on the aromatic ring or heterocycle), a hydroxyl group, a thiol group, a substituted or unsubstituted amino group, a lower alkoxycarbonyl group, a carboxyl group, an aldehyde group, formula (4-a)

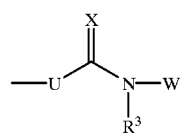

(4-a)

formula (4-b)

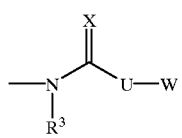

(4-b)

(wherein U denotes an oxygen atom or sulfur atom, X denotes an oxygen atom or sulfur atom, W denotes an aralkyl group, a phenyl group, a naphthyl group, a 5- or 6-membered heterocycle and its condensed ring (each of which may have one or more substituents on the aromatic ring or heterocycle), a lower alkyl group which may be unsubstituted or substituted with at least one halogen atom or a cycloalkyl group, and $R^3$ denotes an aralkyl group, a phenyl group, a naphthyl group, a 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group), or formula (4-c)

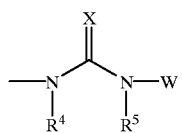

(4-c)

(wherein X denotes an oxygen atom or sulfur atom, W denotes an aralkyl group, a phenyl group, a naphthyl group, a 5- or 6-membered heterocycle and its condensed ring (each of which may have one or more substituents on the aromatic ring or heterocycle), a lower alkyl group which may be unsubstituted or substituted with at least one halogen atom or a cycloalkyl group, and $R^4$ and $R^5$ are identical or different and each independently denote an aralkyl group, a phenyl group, a naphthyl group, a 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group), ring B denotes a saturated or unsaturated heterocycle and its condensed ring (each of which may have one or more substituents on the heterocycle or its condensed ring) which may additionally contain one or two oxygen, nitrogen or sulfur atoms, and m denotes 0 or 1);

A denotes a single bond, a lower alkylene group or a lower alkenylene group,

R denotes a nitro group, a trifluoromethyl group, a substituted or unsubstituted amino group, or formula (7)

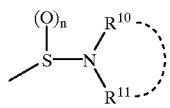

(7)

(wherein $R^{10}$ and $R^{11}$ are identical or different and each independently denote an aralkyl group, a phenyl group, a 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group, or $R^{10}$ and $R^{11}$ may form a ring (wherein said ring may additionally contain one or two heteroatoms) together with a nitrogen atom, and n denotes 1 to 2), $R^1$ denotes an aralkyl group, a phenyl group, a naphthyl group, a 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group, and $R^2$ denotes a hydroxyl group, a lower alkoxy group, formula (6)

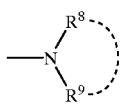

(6)

(wherein $R^8$ and $R^9$ are identical or different and each independently denote an aralkyl group, a phenyl group, a 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group, or $R^8$ and $R^9$ may form a ring (wherein said ring may additionally contain one or two heteroatoms) together with a nitrogen atom, or either of $R^8$ and $R^9$ denotes a hydrogen atom while the other denotes a phenyloxy group or an aralkyloxy group (each of which may have one or more substituents on the aromatic ring), a hydroxyl group or a lower alkoxy group), and their addition salts.

3. A 6,7-asymmetrically disubstituted quinoxalinecarboxylic acid compound represented by formula (8)

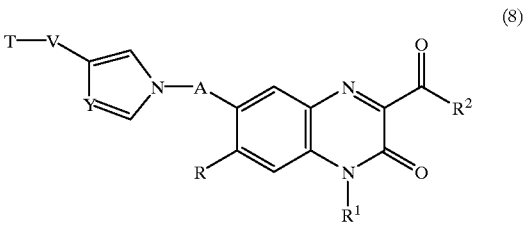

(8)

wherein, V denotes a single bond, a lower alkylene group or a lower alkenylene group, T denotes a phenyl group, a naphthyl group, a 5- or 6-membered heterocycle and its condensed ring (each of which may have one or more substituents on the aromatic ring or heterocycle), a hydroxyl group, a thiol group, a substituted or unsubstituted amino group, a lower alkoxycarbonyl group, a carboxyl group or an aldehyde group, formula (4-a)

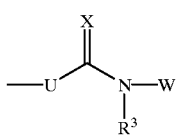

(4-a)

or formula (4-b)

(4-b)

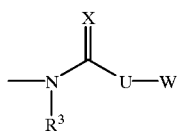

(wherein U denotes an oxygen atom or sulfur atom, X denotes an oxygen atom or sulfur atom, W denotes an aralkyl group, a phenyl group, a naphthyl group, a 5- or 6-membered heterocycle and its condensed ring (each of which may have one or more substituents on the aromatic ring or heterocycle), a lower alkyl group which may be unsubstituted or substituted with at least one halogen atom or a cycloalkyl group, and $R^3$ denotes an aralkyl group, a phenyl group, a naphthyl group, a 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group), or formula (4-c)

(4-c)

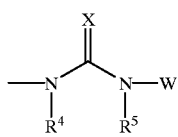

(wherein X denotes an oxygen atom or sulfur atom, W denotes an aralkyl group, a phenyl group, a naphthyl group, a 5- or 6-membered heterocycle and its condensed ring (each of which may have one or more substituents on the aromatic ring or heterocycle), a lower alkyl group which may be unsubstituted or substituted with at least one halogen atom or a cycloalkyl group, and $R^4$ and $R^5$ are identical or different and each independently denote an aralkyl group, a phenyl group, a naphthyl group, a 5- or 6-membered heterocycle and its condensed ring (each of which may have one or more substituents on the aromatic rings or heterocycle), a hydrogen atom, a lower alkyl group which may be unsubstituted or substituted with at least one halogen atom or a cycloalkyl group);

A denotes a single bond, a lower alkylene group or a lower alkenylene group,

R denotes a nitro group, a trifluoromethyl group, a substituted or unsubstituted amino group, or formula (7)

(7)

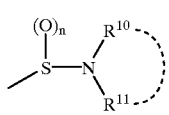

(wherein $R^{10}$ and $R^{11}$ are identical or different and each independently denote an aralkyl group, a phenyl group, a 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group, or $R^{10}$ and $R^{11}$ may form a ring (wherein said ring may additionally contain one or two heteroatoms) together with a nitrogen atom, and n denotes 1 to 2), Y denotes a nitrogen atom or =CH—, $R^1$ denotes an aralkyl group, a phenyl group, a naphthyl group, a 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group, $R^2$ denotes a hydroxyl group, a lower alkoxy group, or formula (6)

(6)

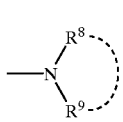

(wherein $R^8$ and $R^9$ are identical or different and each independently denote an aralkyl group, a phenyl group, a 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group, or $R^8$ and $R^9$ may form a ring (wherein said ring may additionally contain one or two heteroatoms) together with a nitrogen atom, or either of $R^8$ and $R^9$ denotes a hydrogen atom while the other denotes a phenyloxy group or an aralkyloxy group (each of which may have one or more substituents on the aromatic ring), a hydroxyl group or a lower alkoxy group), and their addition salts.

4. The 6,7-asymmetrically disubstituted quinoxalinecarboxylic acid compound of claim 3 represented by formula (8)

(8)

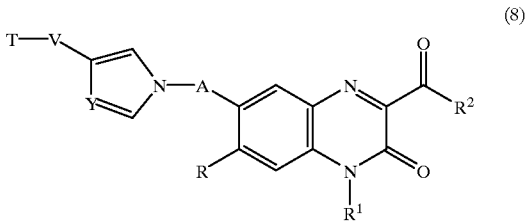

wherein

V denotes a single bond or a lower alkylene group,

A denotes a single bond or a lower alkylene group,

Y denotes a nitrogen atom or =CH—,

R denotes a nitro group, a trifluoromethyl group or a substituted or unsubstituted amino group, $R^1$ denotes a hydrogen atom, and $R^2$ denotes a hydroxyl group or a lower alkoxy group, and their addition salts.

5. The 6,7-asymmetrically disubstituted quinoxalinecarboxylic acid compound of claim 1 represented by formula (9)

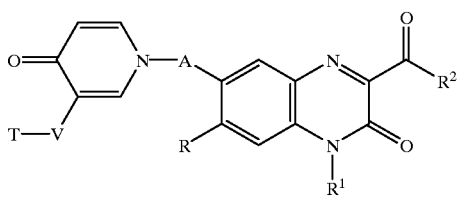

(9)

wherein, V denotes a single bond, a lower alkylene group or a lower alkenylene group, T denotes a phenyl group, a naphthyl group, a 5- or 6-membered heterocycle and its condensed ring (each of which may have one or more substituents on aromatic ring or heterocycle), a hydroxyl group, a thiol group, a substituted or unsubstituted amino group, a lower alkoxycarbonyl group, a carboxyl group or an aldehyde group, formula (4-a),

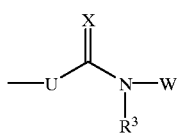

(4-a)

or formula (4-b)

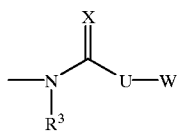

(4-b)

(wherein U denotes an oxygen atom or sulfur atom, X denotes an oxygen atom or sulfur atom, W denotes an aralkyl group, a phenyl group, a naphthyl group, a 5- or 6-membered heterocycle and its condensed ring (each of which may have one or more substituents on the aromatic ring or heterocycle), a lower alkyl group which may be unsubstituted or substituted with at least one halogen atom or a cycloalkyl group, and $R^3$ denotes an aralkyl group, a phenyl group, a naphthyl group, a 5- or 6-membered heterocycle and its condensed ring (each of which may have one or more substituents on aromatic ring or heterocycle), a hydrogen atom, a lower alkyl group which may be unsubstituted or substituted with at least one halogen atom or a cycloalkyl group), or formula (4-c)

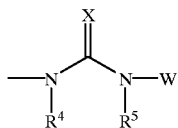

(4-c)

(wherein X denotes an oxygen atom or sulfur atom, W denotes an aralkyl group, a phenyl group, a naphthyl group, a 5- or 6-membered heterocycle and its condensed ring (each of which may have one or more substituents on aromatic ring or heterocycle), a lower alkyl group which may be unsubstituted or substituted with at least one halogen atom or a cycloalkyl group, and $R^4$ and $R^5$ are identical or different and each independently denote an aralkyl group, a phenyl group, a naphthyl group, a 5- or 6-membered heterocycle and its condensed ring (each of which may have one or more substituents on the aromatic ring or heterocycle), a hydrogen atom, a lower alkyl groups which may be unsubstituted or substituted with at least one halogen atom or a cycloalkyl groups);

A denotes a single bond, a lower alkylene group or a lower alkenylene group,

R denotes a nitro group, a trifluoromethyl group, a substituted or unsubstituted amino group, or formula (7)

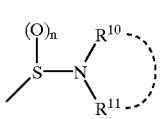

(7)

(wherein $R^{10}$ and $R^{11}$ are identical or different and each independently denote an aralkyl group, a phenyl group, a 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group, or $R^{10}$ and $R^{11}$ may form a ring (wherein said ring may additionally contain one or two heteroatoms) together with a nitrogen atom, and n denotes 1 to 2), $R^1$ denotes an aralkyl group, a phenyl group, a naphthyl group, a 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group, $R^2$ denotes a hydroxyl group, a lower alkoxy group, or formula (6)

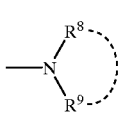

(6)

(wherein $R^8$ and $R^9$ are identical or different and each independently denote an aralkyl group, a phenyl group, a 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group, or $R^8$ and $R^9$ may form a ring (wherein said ring may additionally contain one or two heteroatoms) together with a nitrogen atom, or either of $R^8$ and $R^9$ denotes a hydrogen atom while the other denotes a phenyloxy group or an aralkyloxy group (each of which may have one or more substituents on the aromatic ring), a hydroxyl group or a lower alkoxy group), and their addition salts.

6. The 6,7-asymmetrically disubstituted quinoxalinecarboxylic acid compound of claim 5 represented by formula (9)

(9)

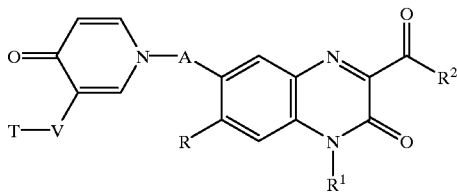

wherein V denotes a single bond or a lower alkylene group,

A denotes a single bond or a lower alkylene group,

R denotes a nitro group, a trifluoromethyl group or a substituted or unsubstituted amino group, $R^1$ denotes a hydrogen atom, and $R^2$ denotes a hydroxyl group or a lower alkoxy group, and their addition salts.

7. The 6,7-asymmetrically disubstituted quinoxalinecarboxylic acid compound of claim 1, wherein the compound is 7-(3-(((4-carboxyphenyl)aminocarbonylamino)methyl) pyrrole-1-yl)-3,4-dihydro-3-oxo-6-trifluoromethylquinoxaline-2-carboxylic acid, and its addition salt.

8. The 6,7-asymmetrically disubstituted quinoxalinecarboxylic acid compound of claim 1, wherein the compound is 7-(4-(((4-carboxyphenyl)aminocarbonylamino)methyl) imidazole-1-yl)-3,4-dihydro-3-oxo-6-trifluoromethylquinoxaline-2-carboxylic acid, and its addition salt.

9. The 6,7-asymmetrically disubstituted quinoxalinecarboxylic acid compound of claim 1, wherein the compound is 7-(4-((N-(4-carboxyphenyl)carbamoyloxy)methyl) imidazole-1-yl)-3,4-dihydro-3-oxo-6-trifluoromethylquinoxaline-2-carboxylic acid, and its addition salt.

10. The 6,7-asymmetrically disubstituted quinoxalinecarboxylic acid compound of claim 1, wherein the compound is 7-(4-((N-(4-carboxyphenyl)carbamoyloxy)methyl) imidazolyl)-3,4-dihydro-6-nitro-3-oxoquinoxaline-2-carboxylic acid, and its addition salt.

11. A composition comprising one or more 6,7-asymmetrically disubstituted quinoxalinecarboxylic acid derivatives represented by formula (1-a)

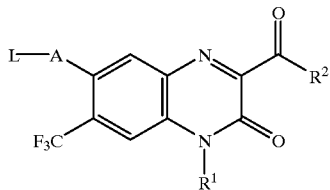

(1-a)

wherein, L denotes a formula (4)

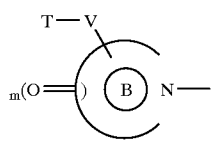

(4)

(wherein V denotes a single bond, a lower alkylene group or a lower alkenylene group, T denotes a phenyl group, a naphthyl group, a 5- or 6-membered heterocycle and its condensed ring (each of which may have one or more substituents on the aromatic ring or heterocycle), a hydroxyl group, a thiol group, a substituted or unsubstituted amino group, a lower alkoxycarbonyl group, a carboxyl group or an aldehyde group, formula (4-a)

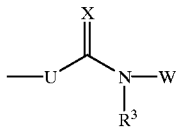

(4-a)

or formula (4-b)

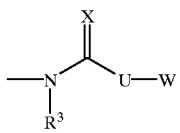

(4-b)

(wherein U denotes an oxygen atom or sulfur atom, X denotes an oxygen atom or sulfur atom, W denotes an aralkyl group, a phenyl group, a naphthyl group, a 5- or 6-membered heterocycle and its condensed ring (each of which may have one or more substituents on the aromatic ring or heterocycle), a lower alkyl group which may be unsubstituted or substituted with at least one halogen atom or a cycloalkyl group, and $R^3$ denotes an aralkyl group, a phenyl group, a naphthyl group, a 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group), or formula (4-c)

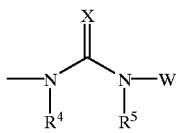

(4-c)

(wherein X denotes an oxygen atom or sulfur atom, W denotes an aralkyl group, a phenyl group, a naphthyl group, a 5- or 6-membered heterocycle and its condensed ring (each of which may have one or more substituents on the aromatic ring or heterocycle), a lower alkyl group which may be unsubstituted or substituted with at least one halogen atom or a cycloalkyl group, and $R^4$ and $R^5$ are identical or different and each independently denote an aralkyl group, a phenyl group, a naphthyl group, a 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group), ring B denotes a saturated or unsaturated heterocycle and its condensed ring (each of which may have one or more substituents on the heterocycle or condensed ring) which may additionally contain one or two oxygen, nitrogen or sulfur atoms, and m denotes 0 or 1);

A denotes a single bond, a lower alkylene group or a lower alkenylene group, $R^1$ denotes an aralkyl group, a phenyl group, a naphthyl group, 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group, and $R^2$ denotes a hydroxyl group, a lower alkoxy group or formula (6)

(6)

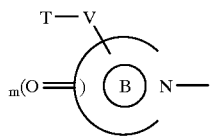

(wherein $R^8$ and $R^9$ are identical or different and each independently denote an aralkyl group, a phenyl group, a 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group, or $R^8$ and $R^9$ may form a ring (wherein said ring may additionally contain one or two heteroatoms) together with a nitrogen atom, or either of $R^8$ and $R^9$ denotes a hydrogen atom while the other denotes a phenyloxy group or an aralkyloxy group (each of which may have one or more substituents on the aromatic ring), a hydroxyl group or a lower alkoxy group), and their addition salts as effective ingredients.

12. A composition comprising one or more 6,7-asymmetrically disubstituted quinoxalinecarboxylic acid derivatives represented by formula (1-b)

(1-b)

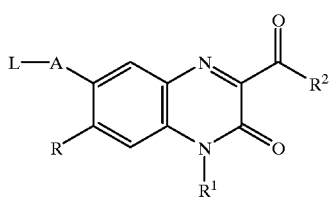

wherein, L denotes a formula (4)

(4)

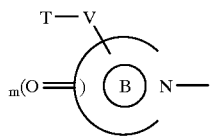

(wherein V denotes a single bond, a lower alkylene group or lower alkenylene group, T denotes a phenyl group, a naphthyl group, a 5- or 6-membered heterocycle and its condensed ring (each of which may have one or more substituents on the aromatic ring or heterocycle), a hydroxyl group, a thiol group, a substituted or unsubstituted amino group, a lower alkoxycarbonyl group, a carboxyl group or an aldehyde group, formula (4-a)

(4-a)

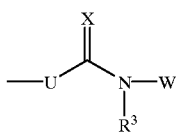

or formula (4-b)

(4-b)

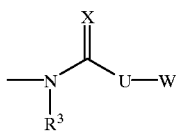

(wherein U denotes an oxygen atom or sulfur atom, X denotes an oxygen atom or sulfur atom, W denotes an aralkyl group, a phenyl group, a naphthyl group, a 5- or 6-membered heterocycle and its condensed ring (each of which may have one or more substituents on the aromatic ring or heterocycle), a lower alkyl group which may be unsubstituted or substituted with at least one halogen atom or a cycloalkyl group, and $R^3$ denotes an aralkyl group, a phenyl group, a naphthyl group, a 5- or 6-membered heterocycle and its condensed ring (each of which may have one or more substituents on aromatic ring or heterocycle), a hydrogen atom, a lower alkyl group which may be unsubstituted or substituted with at least one halogen atom or a cycloalkyl group), or formula (4-c)

(4-c)

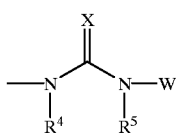

(wherein X denotes an oxygen atom or sulfur atom, W denotes an aralkyl group, a phenyl group, a naphthyl group, a 5- or 6-membered heterocycle and its condensed ring (each of which may have one or more substituents on the aromatic ring or heterocycle), a lower alkyl group which may be unsubstituted or substituted with at least one halogen atom or a cycloalkyl group, and $R^4$ and $R^5$ are identical or different and each independently denote an aralkyl group, a phenyl group, a naphthyl group, a 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group), ring B denotes a saturated or unsaturated heterocycle and its condensed ring (each of which may have one or more substituents on the heterocycle or its condensed ring) which may additionally contain one or two oxygen, nitrogen or sulfur atoms, and m denotes 0 or 1);

A denotes a single bond, a lower alkylene group or a lower alkenylene group,

R denotes a nitro group, a trifluoromethyl group, a substituted or unsubstituted amino group, or formula (7)

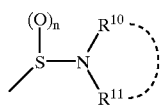

(7)

(wherein $R^{10}$ and $R^{11}$ are identical or different and each independently denote an aralkyl group, a phenyl group, a 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group, or $R^{10}$ and $R^{11}$ may form a ring (wherein said ring may additionally contain one or two heteroatoms) together with a nitrogen atom, and n denotes 1 to 2), $R^1$ denotes an aralkyl group, phenyl group, naphthyl group, 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group, and $R^2$ denotes a hydroxyl group, a lower alkoxy group, or formula (6)

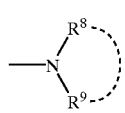

(6)

(wherein $R^8$ and $R^9$ are identical or different and each independently denote an aralkyl group, a phenyl group, a 5- or 6-membered heterocycle and its condensed ring (each of which may have one or more substituents on the aromatic ring or heterocycle), a hydrogen atom, a lower alkyl group which may be unsubstituted or substituted with at least one halogen atom or a cycloalkyl group, or $R^8$ and $R^9$ may form a ring (wherein said ring may additionally contain one or two heteroatoms) together with a nitrogen atom, or either of $R^8$ and $R^9$ denotes a hydrogen atom while the other denotes a phenyloxy group or an aralkyloxy group (each of which may have one or more substituents on the aromatic ring), a hydroxyl group or a lower alkoxy group), and their addition salts as effective ingredients.

\* \* \* \* \*